(12) United States Patent
Dana et al.

(10) Patent No.: US 10,179,160 B2
(45) Date of Patent: *Jan. 15, 2019

(54) THERAPEUTIC COMPOSITIONS FOR THE TREATMENT OF DRY EYE DISEASE

(71) Applicant: SCHEPENS EYE RESEARCH INSTITUTE, Boston, MA (US)

(72) Inventors: Reza Dana, Cambridge, MA (US); Sunil Chauhan, Somerville, MA (US)

(73) Assignee: SCHEPENS EYE RESEARCH INSTITUTE, Boston, MA (US)

( * ) Notice: Subject to any disclaimer, the term of this patent is extended or adjusted under 35 U.S.C. 154(b) by 116 days.

This patent is subject to a terminal disclaimer.

(21) Appl. No.: 15/083,907

(22) Filed: Mar. 29, 2016

(65) Prior Publication Data

US 2016/0256519 A1  Sep. 8, 2016

Related U.S. Application Data

(60) filed as application No. PCT/US2011/026316 on Feb. 25, 2011, now Pat. No. 9,328,162.

(60) Provisional application No. 13/579,170, provisional application No. 61/331,278, filed on May 4, 2010, provisional application No. 61/329,845, filed on Apr. 30, 2010, provisional application No. 61/308,091, filed on Feb. 25, 2010.

(51) Int. Cl.
| | | |
|---|---|---|
| *A61K 38/13* | (2006.01) |
| *C07K 16/22* | (2006.01) |
| *A61K 38/17* | (2006.01) |
| *A61K 9/00* | (2006.01) |
| *A61K 39/395* | (2006.01) |
| *A61K 45/06* | (2006.01) |
| *A61K 31/404* | (2006.01) |
| *A61K 31/44* | (2006.01) |
| *A61K 31/4439* | (2006.01) |
| *A61K 31/444* | (2006.01) |
| *A61K 31/502* | (2006.01) |
| *A61K 31/506* | (2006.01) |
| *A61K 31/517* | (2006.01) |
| *A61K 39/00* | (2006.01) |

(52) U.S. Cl.
CPC ............ *A61K 38/13* (2013.01); *A61K 9/0048* (2013.01); *A61K 31/404* (2013.01); *A61K 31/44* (2013.01); *A61K 31/444* (2013.01); *A61K 31/4439* (2013.01); *A61K 31/502* (2013.01); *A61K 31/506* (2013.01); *A61K 31/517* (2013.01); *A61K 38/179* (2013.01); *A61K 39/3955* (2013.01); *A61K 45/06* (2013.01); *C07K 16/22* (2013.01); *A61K 2039/505* (2013.01); *C07K 2317/76* (2013.01)

(58) Field of Classification Search
CPC ................ A61K 9/0051; A61K 9/0048; A61K 39/3955; A61K 39/395; C07K 16/22; C07K 16/18; A61F 9/0017; A61F 9/0008; A61F 2/142
See application file for complete search history.

(56) References Cited

U.S. PATENT DOCUMENTS

| | | | |
|---|---|---|---|
| 5,225,539 | A | 7/1993 | Winter |
| 5,693,761 | A | 12/1997 | Queen et al. |
| 5,869,619 | A | 2/1999 | Studnicka |
| 5,952,199 | A | 9/1999 | Davis-Smyth et al. |
| 6,107,046 | A | 8/2000 | Alitalo et al. |
| 6,403,088 | B1 | 6/2002 | Alitalo et al. |
| 6,706,487 | B1 | 3/2004 | Abdel-Meguid et al. |
| 6,709,833 | B2 | 3/2004 | Fukui et al. |
| 6,824,777 | B1 | 11/2004 | Alitalo et al. |
| 6,881,557 | B2 | 4/2005 | Foote |
| 7,034,105 | B2 | 4/2006 | Alitalo et al. |
| 7,045,133 | B2 | 5/2006 | Achen et al. |
| 7,109,308 | B1 | 9/2006 | Rosen et al. |
| 7,122,654 | B2 | 10/2006 | Achen et al. |
| 7,208,582 | B2 | 4/2007 | Rosen et al. |
| 7,410,639 | B2 | 8/2008 | Achen et al. |
| 7,422,741 | B2 | 9/2008 | Alitalo et al. |
| 7,423,125 | B2 | 9/2008 | Alitalo et al. |
| 7,611,711 | B2 | 11/2009 | Alitalo et al. |
| 7,759,322 | B2 | 7/2010 | Yerxa et al. |
| 7,825,102 | B2 | 11/2010 | Fishman et al. |
| 7,833,966 | B2 | 11/2010 | Peyman |
| 7,892,081 | B2 | 2/2011 | Glavich et al. |
| 8,444,957 | B2 | 5/2013 | Alitalo et al. |
| 9,011,861 | B2* | 4/2015 | Dana ..................... A61K 38/13 424/130.1 |
| 9,328,162 | B2* | 5/2016 | Dana ..................... A61K 38/13 |
| 2003/0180294 | A1 | 9/2003 | DeVries |

(Continued)

FOREIGN PATENT DOCUMENTS

| | | |
|---|---|---|
| WO | WO-1995/021868 A1 | 8/1995 |
| WO | WO-2000/021560 A1 | 4/2000 |

(Continued)

OTHER PUBLICATIONS

Witmer et al. Vascular endothelial growth factors and angiogenesis in eye disease. Progress in Retinal and Eye Research 22 (2003) 1-29. (Year: 2003).*

(Continued)

*Primary Examiner* — Marcela M Cordero Garcia
*Assistant Examiner* — Jia-Hai Lee
(74) *Attorney, Agent, or Firm* — Marshall, Gerstein & Borun LLP

(57) ABSTRACT

Described herein are materials and methods of treating dry eye disease in a subject.

16 Claims, 11 Drawing Sheets

Specification includes a Sequence Listing.

(56) References Cited

U.S. PATENT DOCUMENTS

| | | | |
|---|---|---|---|
| 2006/0110364 | A1 | 5/2006 | Harding |
| 2006/0177901 | A1 | 8/2006 | Alitalo et al. |
| 2006/0182783 | A1 | 8/2006 | Huges et al. |
| 2007/0078077 | A1 | 4/2007 | Peyman |
| 2007/0155746 | A1* | 7/2007 | Lang .................... C07D 401/04 514/235.5 |
| 2007/0225217 | A1 | 9/2007 | Chappell et al. |
| 2009/0298869 | A1* | 12/2009 | Burnier .............. A61K 31/4709 514/307 |
| 2010/0278736 | A1 | 11/2010 | Alitalo et al. |
| 2011/0200612 | A1 | 8/2011 | Schuster et al. |
| 2011/0206620 | A1 | 8/2011 | Dana et al. |
| 2013/0045927 | A1 | 2/2013 | Dana et al. |

FOREIGN PATENT DOCUMENTS

| | | | | |
|---|---|---|---|---|
| WO | WO-2000/023565 | A2 | 4/2000 | |
| WO | WO-2000/037025 | A2 | 6/2000 | |
| WO | WO-2001/052875 | A1 | 7/2001 | |
| WO | WO-2002/057299 | A2 | 7/2002 | |
| WO | WO-2002/060950 | A2 | 8/2002 | |
| WO | WO-2003/006104 | A2 | 1/2003 | |
| WO | WO-2003/072029 | A2 | 9/2003 | |
| WO | WO-2005/087177 | A2 | 9/2005 | |
| WO | WO-2005/087812 | A1 | 9/2005 | |
| WO | WO-2005/112971 | A1 | 12/2005 | |
| WO | WO-2009/025763 | A2 | 2/2009 | |
| WO | WO-2009/060198 | A1 | 5/2009 | |
| WO | WO-2009/089036 | A2 | 7/2009 | |
| WO | WO-2010/005527 | A1 | 1/2010 | |
| WO | WO2010005527 | A1 * | 1/2010 | .............. C12N 5/00 |
| WO | WO-2010/027743 | A1 | 3/2010 | |
| WO | WO-2010/060768 | A1 | 6/2010 | |

OTHER PUBLICATIONS

NCI Drug Dictionary. https://www.cancer.gov/publications/dictionaries/cancer-drug?cdrid=39201 downloaded Jan. 14, 2018. (Year: 2018).*

Treatment of Dry Eye Syndrome With Cyclosporin A Eye Drops. NCT00001731. Mar. 4, 2008. https://clinicaltrials.gov/ct2/show/NCT00001731 (Year: 2008).*

Alitalo et al., Lymphangiogenesis in development and human disease, *Nature*, 438(7070):946-53 (2005).

Azar, Corneal angiogenic privilege: Angiogenic and antiangiogenic factors in corneal avascularity, vasculogenesis, and wound healing, *Trans. Am. Opthalmol. Soc.*, 104: 264-302 (2006).

Bock et al., Blockade of VEGFR3-signalling specifically inhibits lymphangiogenesis in inflammatory corneal neovascularisation, *Graefes Arch. Clin. Exp. Ophthalmol.*, 246: 115-9 (2007).

Catena et al., VEGF121b and VEGF165b are weakly angiogenic isoforms of VEGF-A, *Molec. Cancer*, 9: 320-34 (2010).

Chauhan et al., A novel pro-lymphangiogenic function for Th17/IL-17, *Blood*, 118(17):4630 (2011).

Chauhan et al., Autoimmunity in dry eye is due to resistance of the Th17 to Treg suppression, *J. Immunol.*, 182:1247-52 (2009).

Chauhan et al., Role of Th17 cells in the immunopathogenesis of dry eye disease, *Mucosal Immunol.* 2(4): 375-6 (2009).

Chen et al., Vascular endothelial growth factor receptor-3 mediates induction of corneal alloimmunity. 2004, *Ocul. Immunol. Inflamm.* 15(3): 275-8 (2007).

Colgan et al., Signaling pathways critical for allergic airway inflammation, *Curr. Opin. Allergy Clin. Immunol.*, 10:42-7 (2010).

Cursiefen et al., Corneal lymphangiogenesis: evidence, mechanisms, and implications for corneal transplant immunology, *Cornea*, 22(3): 273-81 (2003).

Cursiefen et al., Lymphatic vessels in vascularized human corneas: Immunohistochemical investigation using LYVE-1 and podoplanin, *Investig. Opthalmol. Vis. Sci.*, 43(7): 2127-35 (2002).

Cursiefen et al., Time course of angiogenesis and lymphangiogenesis after brief corneal inflammation, *Cornea*, 25(4): 443-7 (2006).

Dana, Corneal Antigen Presentation: Molecular Regulation and Functional Implications, *Oculo Surf.*, S169-72 (2005).

De Paiva et al., IL-17 disrupts corneal barrier following desiccating stress, *Mucosal Immunol.*, 2(3):243 (2006).

De Paiva et al., Rationale for anti-inflammatory therapy in dry eye syndrome, *Arq. Bras. Oftalmol.*, 71:89-95 (2008).

Dugan et al., Review of the classification and assessment of the cutaneous manifestations of the idiopathic inflammatory myopathies, *Dermatology Online Journal*, 15(2) (2009) Retrieved from: http://escholarship.org/uc/item/0f26q4rm.

Ellenberg et al., Novel aspects of corneal angiogenic and lymphangiogenic privilege, *Prog. Retin. Eye Res.*, 29(3): 208-48 (2010).

Enriquez-de-Salamanca et al., Tear cytokine and chemokine analysis and clinical correlations in evaporative-type dry eye disease, *Molecular Vision*, 16:862-873 (2010).

Goyal et al., Blockade of Prolymphangiogenic VEGF-C Suppresses Dry Eye Disease, ARVO Abstract (2010).

Goyal et al., Corneal lymphangiogenesis in murine model of dry eye disease, Abstract, published Feb. 28, 2009.

Goyal et al., Corneal lymphangiogenesis in murine model of dry eye disease, Schepens Eye Research Institute, Department of Ophthalmology, Harvard Medical School, presented May 7, 2009.

Goyal et al., Evidence of corneal lymphangiogenesis in dry eye disease: A potential link to adaptive immunity? *Arch. Opthalmol.*, 128(7): 819-24 (2010).

Grivennikov et al., Inflammation and oncogenesis: a vicious connection, *Curr. Opin. Genet. Dev.*, 20:65-71 (2010).

Hos et al., Age-related changes in murine limbal lymphatic vessels and corneal lymphangiogenesis, *Exp. Eye Res.*, 87(5): 427-32 (2008).

Huggenberger et al., An important role of lymphatic vessel activation in limiting acute inflammation, *Blood*, 117(17):4667-78 (2011).

Huggenberger et al., Stimulation of lymphangiogenesis via VEGFR-3 inhibits chronic skin inflammation, *J. Exper. Med.*, 207(10):2255-69 (2007).

International Preliminary Report on Patentability for International Application No. PCT/US2011/026316, dated Aug. 28, 2012.

International Search Report and Written Opinion of the International Searching Authority for PCT/US2011/026316, dated May 10, 2011.

Jeng et al., Autologous serum 50% eyedrops in the treatment of persistent corneal epithelial defects, *Cornea*, 28(10): 1104-8 (2009).

Jones et al., Replacing the complementarity determining regions in a human antibody with those from a mouse, *Nature*, 321:522-525 (1986).

Kajiya et al., Activation of the VEGFR-3 Pathway by VEGF-C attenuates UVB-induced edema formation and skin inflammation by promoting lymphangiogenesis, *J. Invest. Dermatol.*, 129:1292 (2009).

Kinose et al., Inhibition of retinal and choroidal neovascularization by a novel KDR kinase inhibitor, *Molec. Vision*, 11: 366-73 (2005).

Libby et al., Inflammation in atherosclerosis: Transition from theory to practice, *Circ. J.*, 72:213-20 (2010).

Miller et al., Inflammation and its disconnects; the role of cytokines in the pathophysiology of major depression, *Biol. Psychiatry*, 15:778-88 (2009).

Milmura et al., Expression of vascular endothelial growth factor C and vascular endothelial growth factor receptor 3 in corneal lymphangiogenesis, *Exp. Eye Res.*, 72: 71-8 (2001).

Murdoch et al., Chronic inflammation and asthma, *Mutat. Res.*, 690:24-39 (2010).

Non-Final Office Action issued in connection with U.S. Appl. No. 13/035,695, dated Oct. 30, 2012.

Padlan, E., A Possible Procedure for Reducing the Immunogenicity of Antibody Variable Domains While Preserving Their Ligand-Binding Properties, *Molec. Immunol.* 28(4): 489-498 (1991).

Patel et al., Corneal lymphangiogenesis: Implication in immunity, *Semin. Opthalmol.*, 24(3): 135-8 (2009).

Pegaptanib, New drug. In macular degeneration: Too many risks for too little benefit, Prescre Int. 15(84): 127-9 (2006).

Pullinger et al., Proliferation of lymphatics in inflammation, *J. Pathol*, 157-70 (1937).

(56) References Cited

OTHER PUBLICATIONS

Rashid et al., Topical Omega-3 and Omega-6 Fatty Acids for Treatment of Dry Eye, *Arch Ophthalmol*, 126(2):219-225 (2008).
Steffensmeier et al., Vitreous injections of Pegaptanib sodium triggering allergic reactions, *Am. J. Ophthalmol*. 14(3): 512-3 (2007).
Van de Veire et al., Further pharmacological and genetic evidence for the efficacy of PlGF inhibition in cancer and eye disease, *Cell*, 141: 178-90 (2010).
Watari et al., Role of macrophages in inflammatory lymphangiogenesis: Enhanced production of vascular endothelial growth factor C and D through NF-kappaB activation, *Biochem. Biophys. Res. Commun.*, 377(3): 836-31 (2008).
Witte et al., Monoclonal antibodies targeting the VEGF receptor-2 (Flk1/KDR) as an anti-angiogenic therapeutic strategy, *Cancer Metastasis Rev.* 17: 155-61 (1998).
Woolard et al., VEGF165b, an inhibitory vascular endothelial growth factor splice variant: Mechanism of action, in vivo effect on angiogenesis and endogenous protein expression, *Cancer Res.*, 64: 7822-35 (2004).
Yoshida et al., Inflammatory bowel disease: a paradigm for the link between coagulation and inflammation, *Inflamm. Bowel Dis.*, 15:1245-55 (2009).
Yu et al., Interaction between Bevacizumab and murine VEGF-A: A reassessment, *Invest. Ophthalmol. Vis. Sci.*, 49(2): 522-7 (2008).
Dr. Saban, Declaration Under 37 C.F.R. 1.132 dated Nov. 24, 2014.
Dr. Dana Declaration Under 37 C.F.R. 1.132 dated Feb. 27, 2014.
Dr. Baldwin Declaration Under 37 C.F.R. 1.132 dated Sep. 9, 2013.

\* cited by examiner

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Gly or a conservative substitution
      thereof
<220> FEATURE:
<221> NAME/KEY: MISC_FEATURE
<222> LOCATION: (2)..(2)
<223> OTHER INFORMATION: Xaa is Tyr or a conservative substitution
      thereof
<220> FEATURE:
<221> NAME/KEY: MISC_FEATURE
<222> LOCATION: (3)..(3)
<223> OTHER INFORMATION: Xaa is Trp or a conservative substitution
      thereof
<220> FEATURE:
<221> NAME/KEY: MISC_FEATURE
<222> LOCATION: (4)..(4)
<223> OTHER INFORMATION: Xaa is Leu or a conservative substitution
      thereof
<220> FEATURE:
<221> NAME/KEY: MISC_FEATURE
<222> LOCATION: (5)..(5)
<223> OTHER INFORMATION: Xaa is Thr or a conservative substitution
      thereof
<220> FEATURE:
<221> NAME/KEY: MISC_FEATURE
```

```
<222> LOCATION: (6)..(6)
<223> OTHER INFORMATION: Xaa is Ile or a conservative substitution
      thereof
<220> FEATURE:
<221> NAME/KEY: MISC_FEATURE
<222> LOCATION: (7)..(7)
<223> OTHER INFORMATION: Xaa is Trp or a conservative substitution
      thereof
<220> FEATURE:
<221> NAME/KEY: MISC_FEATURE
<222> LOCATION: (8)..(8)
<223> OTHER INFORMATION: Xaa is Glyor a conservative substitution
      thereof

<400> SEQUENCE: 1

Xaa Xaa Xaa Xaa Xaa Xaa Xaa Xaa
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Gly or a conservative substitution
      thereof
<220> FEATURE:
<221> NAME/KEY: MISC_FEATURE
<222> LOCATION: (3)..(3)
<223> OTHER INFORMATION: Xaa is Tyr or a conservative substitution
      thereof
<220> FEATURE:
<221> NAME/KEY: MISC_FEATURE
<222> LOCATION: (4)..(4)
<223> OTHER INFORMATION: Xaa is Trp or a conservative substitution
      thereof
<220> FEATURE:
<221> NAME/KEY: MISC_FEATURE
<222> LOCATION: (5)..(5)
<223> OTHER INFORMATION: Xaa is Leu or a conservative substitution
      thereof
<220> FEATURE:
<221> NAME/KEY: MISC_FEATURE
<222> LOCATION: (6)..(6)
<223> OTHER INFORMATION: Xaa is Thr or a conservative substitution
      thereof
<220> FEATURE:
<221> NAME/KEY: MISC_FEATURE
<222> LOCATION: (7)..(7)
<223> OTHER INFORMATION: Xaa is Ile or a conservative substitution
      thereof
<220> FEATURE:
<221> NAME/KEY: MISC_FEATURE
<222> LOCATION: (8)..(8)
<223> OTHER INFORMATION: Xaa is Trp or a conservative substitution
      thereof
<220> FEATURE:
<221> NAME/KEY: MISC_FEATURE
<222> LOCATION: (9)..(9)
<223> OTHER INFORMATION: Xaa is Glyor a conservative substitution
      thereof

<400> SEQUENCE: 2

Cys Xaa Xaa Xaa Xaa Xaa Xaa Xaa Xaa Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 3

Xaa Gly Tyr Trp Leu Thr Ile Trp Gly Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(10)
<223> OTHER INFORMATION: Cyclic peptide

<400> SEQUENCE: 4

Cys Gly Tyr Trp Leu Thr Ile Trp Gly Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(13)

<400> SEQUENCE: 5

Cys Ala Ser Glu Leu Gly Lys Ser Thr Asn Thr Phe Cys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(8)

<400> SEQUENCE: 6

Cys Asn Glu Glu Ser Leu Ile Cys
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(11)

<400> SEQUENCE: 7

Cys Ile Ser Val Pro Leu Thr Ser Val Pro Cys
1               5                   10
```

```
<210> SEQ ID NO 8
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(13)

<400> SEQUENCE: 8

Cys Ala Ser Glu Leu Gly Lys Ser Thr Asn Thr Phe Cys Lys Pro Pro
1               5                   10                  15

Cys

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(9)

<400> SEQUENCE: 9

Cys Cys Asn Glu Glu Ser Leu Ile Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(9)

<400> SEQUENCE: 10

Cys Ser Val Pro Leu Thr Ser Val Cys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(7)

<400> SEQUENCE: 11

Cys Val Pro Leu Thr Ser Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(6)

<400> SEQUENCE: 12
```

```
Cys Val Pro Leu Thr Cys
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(10)

<400> SEQUENCE: 13

Cys Ile Ser Val Pro Leu Ser Val Pro Cys
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(9)

<400> SEQUENCE: 14

Cys Ile Ser Val Pro Leu Val Pro Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ser Gly Tyr Trp Trp Asp Thr Trp Phe
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Ser Cys Tyr Trp Arg Asp Thr Trp Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Lys Val Gly Trp Ser Ser Pro Asp Trp
1               5

<210> SEQ ID NO 18
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 18

Phe Val Gly Trp Thr Lys Val Leu Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Tyr Ser Ser Ser Met Arg Trp Arg His
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Arg Trp Arg Gly Asn Ala Tyr Pro Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Ser Ala Val Phe Arg Gly Arg Trp Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Trp Phe Ser Ala Ser Leu Arg Phe Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Trp Gln Leu Gly Arg Asn Trp Ile
1               5

<210> SEQ ID NO 24
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 24

Val Glu Val Gln Ile Thr Gln Glu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Ala Gly Lys Ala Ser Ser Leu Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Arg Ala Leu Asp Ser Ala Leu Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Tyr Gly Phe Glu Ala Ala Trp
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Tyr Gly Phe Leu Trp Gly Met
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Ser Arg Trp Arg Ile Leu Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 30

His Lys Trp Gln Lys Arg Gln
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Met Asp Pro Trp Gly Gly Trp
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Arg Lys Val Trp Asp Ile Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

Val Trp Asp His Gly Val
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Cys Trp Gln Leu Gly Arg Asn Trp Ile Cys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Cys Val Glu Val Gln Ile Thr Gln Glu Cys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 36

Cys Ala Gly Lys Ala Ser Ser Leu Trp Cys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide

<400> SEQUENCE: 37

Cys Arg Ala Leu Asp Ser Ala Leu Ala Cys
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Cys Tyr Gly Phe Glu Ala Ala Trp Cys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Cys Tyr Gly Phe Leu Trp Gly Met Cys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Cys Ser Arg Trp Arg Ile Leu Gly Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Cys His Lys Trp Gln Lys Arg Gln Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42
```

```
Cys Met Asp Pro Trp Gly Gly Trp Cys
1               5
```

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

```
Cys Arg Lys Val Trp Asp Ile Arg Cys
1               5
```

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

```
Cys Val Trp Asp His Gly Val Cys
1               5
```

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide

<400> SEQUENCE: 45

```
Cys Gly Gln Met Cys Thr Val Trp Cys Ser Ser Gly Cys
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 46

```
Gly Tyr Trp Xaa Xaa Xaa Trp
1               5
```

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 47

```
Gly Tyr Trp Xaa Xaa Xaa Trp Xaa
```

<210> SEQ ID NO 48
<211> LENGTH: 448
<212> TYPE: PRT
<213> ORGANISM: Homo sapiens

<400> SEQUENCE: 48

Glu Val Arg Leu Leu Glu Ser Gly Gly Leu Val Gln Pro Gly Gly
1               5                   10                  15

Ser Leu Arg Leu Ser Cys Ala Ala Ser Gly Phe Thr Phe Arg Pro Arg
            20                  25                  30

Ala Met Ala Trp Val Arg Gln Ala Pro Gly Lys Gly Leu Glu Trp Val
        35                  40                  45

Ser Ser Ile Ser Ala Gln Gly Ala Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Val Ser Gly Phe Gly Pro Trp Gly Arg Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 49
<211> LENGTH: 217
<212> TYPE: PRT
<213> ORGANISM: Homo sapiens

<400> SEQUENCE: 49

```
Ser Tyr Glu Leu Thr Gln Pro Pro Ser Ser Gly Thr Pro Gly Gln
1               5                   10                  15
Arg Val Thr Ile Ser Cys Ser Gly Ser Ser Asn Ile Gly Arg His
            20                  25                  30
Thr Val Ser Trp Tyr Gln Gln Val Pro Gly Thr Ala Pro Lys Leu Leu
        35                  40                  45
Ile Tyr Ser Asp Asp His Arg Pro Ser Gly Val Pro Asp Arg Phe Ser
50                  55                  60
Ala Ser Lys Ser Gly Thr Ser Ala Ser Leu Thr Ile Thr Gly Leu Gln
65                  70                  75                  80
Ser Glu Asp Glu Ala Asp Tyr Tyr Cys Ala Ala Trp Asp Asp Ser Leu
                85                  90                  95
Asn Gly Pro Trp Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 50
<211> LENGTH: 2292
<212> TYPE: DNA
<213> ORGANISM: Homo sapiens
<220> FEATURE:
<221> NAME/KEY: CDS
<222> LOCATION: (1)..(2292)

<400> SEQUENCE: 50

```
atg gag agc aag gtg ctg ctg gcc gtc gcc ctg tgg ctc tgc gtg gag     48
Met Glu Ser Lys Val Leu Leu Ala Val Ala Leu Trp Leu Cys Val Glu
1               5                   10                  15
```

-continued

| | | |
|---|---|---|
| acc cgg gcc gcc tct gtg ggt ttg cct agt gtt tct ctt gat ctg ccc<br>Thr Arg Ala Ala Ser Val Gly Leu Pro Ser Val Ser Leu Asp Leu Pro<br>20 25 30 | 96 | |
| agg ctc agc ata caa aaa gac ata ctt aca att aag gct aat aca act<br>Arg Leu Ser Ile Gln Lys Asp Ile Leu Thr Ile Lys Ala Asn Thr Thr<br>35 40 45 | 144 | |
| ctt caa att act tgc agg gga cag agg gac ttg gac tgg ctt tgg ccc<br>Leu Gln Ile Thr Cys Arg Gly Gln Arg Asp Leu Asp Trp Leu Trp Pro<br>50 55 60 | 192 | |
| aat aat cag agt ggc agt gag caa agg gtg gag gtg act gag tgc agc<br>Asn Asn Gln Ser Gly Ser Glu Gln Arg Val Glu Val Thr Glu Cys Ser<br>65 70 75 80 | 240 | |
| gat ggc ctc ttc tgt aag aca ctc aca att cca aaa gtg atc gga aat<br>Asp Gly Leu Phe Cys Lys Thr Leu Thr Ile Pro Lys Val Ile Gly Asn<br>85 90 95 | 288 | |
| gac act gga gcc tac aag tgc ttc tac cgg gaa act gac ttg gcc tcg<br>Asp Thr Gly Ala Tyr Lys Cys Phe Tyr Arg Glu Thr Asp Leu Ala Ser<br>100 105 110 | 336 | |
| gtc att tat gtc tat gtt caa gat tac aga tct cca ttt att gct tct<br>Val Ile Tyr Val Tyr Val Gln Asp Tyr Arg Ser Pro Phe Ile Ala Ser<br>115 120 125 | 384 | |
| gtt agt gac caa cat gga gtc gtg tac att act gag aac aaa aac aaa<br>Val Ser Asp Gln His Gly Val Val Tyr Ile Thr Glu Asn Lys Asn Lys<br>130 135 140 | 432 | |
| act gtg gtg att cca tgt ctc ggg tcc att tca aat ctc aac gtg tca<br>Thr Val Val Ile Pro Cys Leu Gly Ser Ile Ser Asn Leu Asn Val Ser<br>145 150 155 160 | 480 | |
| ctt tgt gca aga tac cca gaa aag aga ttt gtt cct gat ggt aac aga<br>Leu Cys Ala Arg Tyr Pro Glu Lys Arg Phe Val Pro Asp Gly Asn Arg<br>165 170 175 | 528 | |
| att tcc tgg gac agc aag aag ggc ttt act att ccc agc tac atg atc<br>Ile Ser Trp Asp Ser Lys Lys Gly Phe Thr Ile Pro Ser Tyr Met Ile<br>180 185 190 | 576 | |
| agc tat gct ggc atg gtc ttc tgt gaa gca aaa att aat gat gaa agt<br>Ser Tyr Ala Gly Met Val Phe Cys Glu Ala Lys Ile Asn Asp Glu Ser<br>195 200 205 | 624 | |
| tac cag tct att atg tac ata gtt gtc gtt gta ggg tat agg att tat<br>Tyr Gln Ser Ile Met Tyr Ile Val Val Val Gly Tyr Arg Ile Tyr<br>210 215 220 | 672 | |
| gat gtg gtt ctg agt ccg tct cat gga att gaa cta tct gtt gga gaa<br>Asp Val Val Leu Ser Pro Ser His Gly Ile Glu Leu Ser Val Gly Glu<br>225 230 235 240 | 720 | |
| aag ctt gtc tta aat tgt aca gca aga act gaa cta aat gtg ggg att<br>Lys Leu Val Leu Asn Cys Thr Ala Arg Thr Glu Leu Asn Val Gly Ile<br>245 250 255 | 768 | |
| gac ttc aac tgg gaa tac cct tct tcg aag cat cag cat aag aaa ctt<br>Asp Phe Asn Trp Glu Tyr Pro Ser Ser Lys His Gln His Lys Lys Leu<br>260 265 270 | 816 | |
| gta aac cga gac cta aaa acc cag tct ggg agt gag atg aag aaa ttt<br>Val Asn Arg Asp Leu Lys Thr Gln Ser Gly Ser Glu Met Lys Lys Phe<br>275 280 285 | 864 | |
| ttg agc acc tta act ata gat ggt gta acc cgg agt gac caa gga ttg<br>Leu Ser Thr Leu Thr Ile Asp Gly Val Thr Arg Ser Asp Gln Gly Leu<br>290 295 300 | 912 | |
| tac acc tgt gca gca tcc agt ggg ctg atg acc aag aag aac agc aca<br>Tyr Thr Cys Ala Ala Ser Ser Gly Leu Met Thr Lys Lys Asn Ser Thr<br>305 310 315 320 | 960 | |
| ttt gtc agg gtc cat gaa aaa cct ttt gtt gct ttt gga agt ggc atg<br>Phe Val Arg Val His Glu Lys Pro Phe Val Ala Phe Gly Ser Gly Met | 1008 | |

-continued

|  |  |  | 325 |  |  |  | 330 |  |  |  | 335 |  |  |  |  |
|---|---|---|---|---|---|---|---|---|---|---|---|---|---|---|---|
| gaa | tct | ctg | gtg | gaa | gcc | acg | gtg | ggg | gag | cgt | gtc | aga | atc | cct | gcg | 1056 |
| Glu | Ser | Leu | Val | Glu | Ala | Thr | Val | Gly | Glu | Arg | Val | Arg | Ile | Pro | Ala |
|  |  |  | 340 |  |  |  | 345 |  |  |  | 350 |  |  |  |  |

| aag | tac | ctt | ggt | tac | cca | ccc | cca | gaa | ata | aaa | tgg | tat | aaa | aat | gga | 1104 |
| Lys | Tyr | Leu | Gly | Tyr | Pro | Pro | Pro | Glu | Ile | Lys | Trp | Tyr | Lys | Asn | Gly |
|  |  |  | 355 |  |  |  | 360 |  |  |  | 365 |  |  |  |  |

| ata | ccc | ctt | gag | tcc | aat | cac | aca | att | aaa | gcg | ggg | cat | gta | ctg | acg | 1152 |
| Ile | Pro | Leu | Glu | Ser | Asn | His | Thr | Ile | Lys | Ala | Gly | His | Val | Leu | Thr |
|  | 370 |  |  |  |  | 375 |  |  |  |  | 380 |  |  |  |  |

| att | atg | gaa | gtg | agt | gaa | aga | gac | aca | gga | aat | tac | act | gtc | atc | ctt | 1200 |
| Ile | Met | Glu | Val | Ser | Glu | Arg | Asp | Thr | Gly | Asn | Tyr | Thr | Val | Ile | Leu |
| 385 |  |  |  |  | 390 |  |  |  |  | 395 |  |  |  |  | 400 |

| acc | aat | ccc | att | tca | aag | gag | aag | cag | agc | cat | gtg | gtc | tct | ctg | gtt | 1248 |
| Thr | Asn | Pro | Ile | Ser | Lys | Glu | Lys | Gln | Ser | His | Val | Val | Ser | Leu | Val |
|  |  |  |  | 405 |  |  |  |  | 410 |  |  |  |  | 415 |  |

| gtg | tat | gtc | cca | ccc | cag | att | ggt | gag | aaa | tct | cta | atc | tct | cct | gtg | 1296 |
| Val | Tyr | Val | Pro | Pro | Gln | Ile | Gly | Glu | Lys | Ser | Leu | Ile | Ser | Pro | Val |
|  |  |  | 420 |  |  |  |  | 425 |  |  |  |  | 430 |  |  |

| gat | tcc | tac | cag | tac | ggc | acc | act | caa | acg | ctg | aca | tgt | acg | gtc | tat | 1344 |
| Asp | Ser | Tyr | Gln | Tyr | Gly | Thr | Thr | Gln | Thr | Leu | Thr | Cys | Thr | Val | Tyr |
|  |  | 435 |  |  |  |  | 440 |  |  |  |  | 445 |  |  |  |

| gcc | att | cct | ccc | ccg | cat | cac | atc | cac | tgg | tat | tgg | cag | ttg | gag | gaa | 1392 |
| Ala | Ile | Pro | Pro | Pro | His | His | Ile | His | Trp | Tyr | Trp | Gln | Leu | Glu | Glu |
| 450 |  |  |  |  | 455 |  |  |  |  | 460 |  |  |  |  |  |

| gag | tgc | gcc | aac | gag | ccc | agc | caa | gct | gtc | tca | gtg | aca | aac | cca | tac | 1440 |
| Glu | Cys | Ala | Asn | Glu | Pro | Ser | Gln | Ala | Val | Ser | Val | Thr | Asn | Pro | Tyr |
| 465 |  |  |  |  | 470 |  |  |  |  | 475 |  |  |  |  | 480 |

| cct | tgt | gaa | gaa | tgg | aga | agt | gtg | gag | gac | ttc | cag | gga | gga | aat | aaa | 1488 |
| Pro | Cys | Glu | Glu | Trp | Arg | Ser | Val | Glu | Asp | Phe | Gln | Gly | Gly | Asn | Lys |
|  |  |  |  | 485 |  |  |  |  | 490 |  |  |  |  | 495 |  |

| att | gaa | gtt | aat | aaa | aat | caa | ttt | gct | cta | att | gaa | gga | aaa | aac | aaa | 1536 |
| Ile | Glu | Val | Asn | Lys | Asn | Gln | Phe | Ala | Leu | Ile | Glu | Gly | Lys | Asn | Lys |
|  |  |  | 500 |  |  |  |  | 505 |  |  |  |  | 510 |  |  |

| act | gta | agt | acc | ctt | gtt | atc | caa | gcg | gca | aat | gtg | tca | gct | ttg | tac | 1584 |
| Thr | Val | Ser | Thr | Leu | Val | Ile | Gln | Ala | Ala | Asn | Val | Ser | Ala | Leu | Tyr |
|  |  | 515 |  |  |  |  | 520 |  |  |  |  | 525 |  |  |  |

| aaa | tgt | gaa | gcg | gtc | aac | aaa | gtc | ggg | aga | gga | gag | agg | gtg | atc | tcc | 1632 |
| Lys | Cys | Glu | Ala | Val | Asn | Lys | Val | Gly | Arg | Gly | Glu | Arg | Val | Ile | Ser |
| 530 |  |  |  |  | 535 |  |  |  |  | 540 |  |  |  |  |  |

| ttc | cac | gtg | acc | agg | ggt | cct | gaa | att | act | ttg | caa | cct | gac | atg | cag | 1680 |
| Phe | His | Val | Thr | Arg | Gly | Pro | Glu | Ile | Thr | Leu | Gln | Pro | Asp | Met | Gln |
| 545 |  |  |  |  | 550 |  |  |  |  | 555 |  |  |  |  | 560 |

| ccc | act | gag | cag | gag | agc | gtg | tct | ttg | tgg | tgc | act | gca | gac | aga | tct | 1728 |
| Pro | Thr | Glu | Gln | Glu | Ser | Val | Ser | Leu | Trp | Cys | Thr | Ala | Asp | Arg | Ser |
|  |  |  |  | 565 |  |  |  |  | 570 |  |  |  |  | 575 |  |

| acg | ttt | gag | aac | ctc | aca | tgg | tac | aag | ctt | ggc | cca | cag | cct | ctg | cca | 1776 |
| Thr | Phe | Glu | Asn | Leu | Thr | Trp | Tyr | Lys | Leu | Gly | Pro | Gln | Pro | Leu | Pro |
|  |  |  | 580 |  |  |  |  | 585 |  |  |  |  | 590 |  |  |

| atc | cat | gtg | gga | gag | ttg | ccc | aca | cct | gtt | tgc | aag | aac | ttg | gat | act | 1824 |
| Ile | His | Val | Gly | Glu | Leu | Pro | Thr | Pro | Val | Cys | Lys | Asn | Leu | Asp | Thr |
|  |  | 595 |  |  |  |  | 600 |  |  |  |  | 605 |  |  |  |

| ctt | tgg | aaa | ttg | aat | gcc | acc | atg | ttc | tct | aat | agc | aca | aat | gac | att | 1872 |
| Leu | Trp | Lys | Leu | Asn | Ala | Thr | Met | Phe | Ser | Asn | Ser | Thr | Asn | Asp | Ile |
| 610 |  |  |  |  | 615 |  |  |  |  | 620 |  |  |  |  |  |

| ttg | atc | atg | gag | ctt | aag | aat | gca | tcc | ttg | cag | gac | caa | gga | gac | tat | 1920 |
| Leu | Ile | Met | Glu | Leu | Lys | Asn | Ala | Ser | Leu | Gln | Asp | Gln | Gly | Asp | Tyr |
| 625 |  |  |  |  | 630 |  |  |  |  | 635 |  |  |  |  | 640 |

| gtc | tgc | ctt | gct | caa | gac | agg | aag | acc | aag | aaa | aga | cat | tgc | gtg | gtc | 1968 |

-continued

```
Val Cys Leu Ala Gln Asp Arg Lys Thr Lys Lys Arg His Cys Val Val
                    645                 650                 655 agg cag ctc aca gtc cta gag cgt gtg gca ccc acg atc aca gga aac    2016
Arg Gln Leu Thr Val Leu Glu Arg Val Ala Pro Thr Ile Thr Gly Asn
            660                 665                 670 ctg gag aat cag acg aca agt att ggg gaa agc atc gaa gtc tca tgc    2064
Leu Glu Asn Gln Thr Thr Ser Ile Gly Glu Ser Ile Glu Val Ser Cys
        675                 680                 685 acg gca tct ggg aat ccc cct cca cag atc atg tgg ttt aaa gat aat    2112
Thr Ala Ser Gly Asn Pro Pro Pro Gln Ile Met Trp Phe Lys Asp Asn
    690                 695                 700 gag acc ctt gta gaa gac tca ggc att gta ttg aag gat ggg aac cgg    2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc    2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc    2256
Cys Gln Ala Cys Ser Val Leu Gly Cys Ala Lys Val Glu Ala Phe Phe
            740                 745                 750 ata ata gaa ggt gcc cag gaa aag acg aac ttg gaa                    2292
Ile Ile Glu Gly Ala Gln Glu Lys Thr Asn Leu Glu
        755                 760

<210> SEQ ID NO 51
<211> LENGTH: 764
<212> TYPE: PRT
<213> ORGANISM: Homo sapiens

<400> SEQUENCE: 51

Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
```

```
            210                 215                 220
Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640
```

```
Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu
        755                 760

<210> SEQ ID NO 52
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 52
ccacgcgcag cggccggag atg cag cgg ggc gcc gcg ctg tgc ctg cga ctg        52
                    Met Gln Arg Gly Ala Ala Leu Cys Leu Arg Leu
                     1               5                  10 tgg ctc tgc ctg gga ctc ctg gac ggc ctg gtg agt ggc tac tcc atg       100
Trp Leu Cys Leu Gly Leu Leu Asp Gly Leu Val Ser Gly Tyr Ser Met
         15                  20                  25 acc ccc ccg acc ttg aac atc acg gag gag tca cac gtc atc gac acc       148
Thr Pro Pro Thr Leu Asn Ile Thr Glu Glu Ser His Val Ile Asp Thr
     30                  35                  40 ggt gac agc ctg tcc atc tcc tgc agg gga cag cac ccc ctc gag tgg       196
Gly Asp Ser Leu Ser Ile Ser Cys Arg Gly Gln His Pro Leu Glu Trp
 45                  50                  55 gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                 80                  85                  90 tac tgc aag gtg ttg ctg ctg cac gag gta cat gcc aac gac aca ggc       340
Tyr Cys Lys Val Leu Leu Leu His Glu Val His Ala Asn Asp Thr Gly
             95                 100                 105 agc tac gtc tgc tac tac aag tac atc aag gca cgc atc gag ggc acc       388
Ser Tyr Val Cys Tyr Tyr Lys Tyr Ile Lys Ala Arg Ile Glu Gly Thr
         110                 115                 120 acg gcc gcc agc tcc tac gtg ttc gtg aga gac ttt gag cag cca ttc       436
Thr Ala Ala Ser Ser Tyr Val Phe Val Arg Asp Phe Glu Gln Pro Phe
     125                 130                 135 atc aac aag cct gac acg ctc ttg gtc aac agg aag gac gcc atg tgg       484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg       532
Val Pro Cys Leu Val Ser Ile Pro Gly Leu Asn Val Thr Leu Arg Ser
                160                 165                 170
```

-continued

| | | |
|---|---|---|
| caa agc tcg gtg ctg tgg cca gac ggg cag gag gtg gtg tgg gat gac<br>Gln Ser Ser Val Leu Trp Pro Asp Gly Gln Glu Val Val Trp Asp Asp<br>               175                       180                         185 | 580 |
| cgg cgg ggc atg ctc gtg tcc acg cca ctg ctg cac gat gcc ctg tac<br>Arg Arg Gly Met Leu Val Ser Thr Pro Leu Leu His Asp Ala Leu Tyr<br>         190                         195                         200 | 628 |
| ctg cag tgc gag acc acc tgg gga gac cag gac ttc ctt tcc aac ccc<br>Leu Gln Cys Glu Thr Thr Trp Gly Asp Gln Asp Phe Leu Ser Asn Pro<br>205                         210                         215 | 676 |
| ttc ctg gtg cac atc aca ggc aac gag ctc tat gac atc cag ctg ttg<br>Phe Leu Val His Ile Thr Gly Asn Glu Leu Tyr Asp Ile Gln Leu Leu<br>220                       225                       230                   235 | 724 |
| ccc agg aag tcg ctg gag ctg ctg gta ggg gag aag ctg gtc ctg aac<br>Pro Arg Lys Ser Leu Glu Leu Leu Val Gly Glu Lys Leu Val Leu Asn<br>               240                       245                       250 | 772 |
| tgc acc gtg tgg gct gag ttt aac tca ggt gtc acc ttt gac tgg gac<br>Cys Thr Val Trp Ala Glu Phe Asn Ser Gly Val Thr Phe Asp Trp Asp<br>                   255                       260                       265 | 820 |
| tac cca ggg aag cag gca gag cgg ggt aag tgg gtg ccc gag cga cgc<br>Tyr Pro Gly Lys Gln Ala Glu Arg Gly Lys Trp Val Pro Glu Arg Arg<br>         270                         275                         280 | 868 |
| tcc cag cag acc cac aca gaa ctc tcc agc atc ctg acc atc cac aac<br>Ser Gln Gln Thr His Thr Glu Leu Ser Ser Ile Leu Thr Ile His Asn<br>285                         290                         295 | 916 |
| gtc agc cag cac gac ctg ggc tcg tat gtg tgc aag gcc aac aac ggc<br>Val Ser Gln His Asp Leu Gly Ser Tyr Val Cys Lys Ala Asn Asn Gly<br>300                       305                       310                   315 | 964 |
| atc cag cga ttt cgg gag agc acc gag gtc att gtg cat gaa aat ccc<br>Ile Gln Arg Phe Arg Glu Ser Thr Glu Val Ile Val His Glu Asn Pro<br>               320                       325                       330 | 1012 |
| ttc atc agc gtc gag tgg ctc aaa gga ccc atc ctg gag gcc acg gca<br>Phe Ile Ser Val Glu Trp Leu Lys Gly Pro Ile Leu Glu Ala Thr Ala<br>                   335                       340                       345 | 1060 |
| gga gac gag ctg gtg aag ctg ccc gtg aag ctg gca gcg tac ccc ccg<br>Gly Asp Glu Leu Val Lys Leu Pro Val Lys Leu Ala Ala Tyr Pro Pro<br>         350                         355                         360 | 1108 |
| ccc gag ttc cag tgg tac aag gat gga aag gca ctg tcc ggg cgc cac<br>Pro Glu Phe Gln Trp Tyr Lys Asp Gly Lys Ala Leu Ser Gly Arg His<br>365                         370                         375 | 1156 |
| agt cca cat gcc ctg gtg ctc aag gag gtg aca gag gcc agc aca ggc<br>Ser Pro His Ala Leu Val Leu Lys Glu Val Thr Glu Ala Ser Thr Gly<br>380                         385                         390                   395 | 1204 |
| acc tac acc ctc gcc ctg tgg aac tcc gct gct ggc ctg agg cgc aac<br>Thr Tyr Thr Leu Ala Leu Trp Asn Ser Ala Ala Gly Leu Arg Arg Asn<br>               400                       405                       410 | 1252 |
| atc agc ctg gag ctg gtg gtg aat gtg ccc ccc cag ata cat gag aag<br>Ile Ser Leu Glu Leu Val Val Asn Val Pro Pro Gln Ile His Glu Lys<br>         415                         420                         425 | 1300 |
| gag gcc tcc tcc ccc agc atc tac tcg cgt cac agc cgc cag gcc ctc<br>Glu Ala Ser Ser Pro Ser Ile Tyr Ser Arg His Ser Arg Gln Ala Leu<br>               430                       435                       440 | 1348 |
| acc tgc acg gcc tac ggg gtg ccc ctg cct ctc agc atc cag tgg cac<br>Thr Cys Thr Ala Tyr Gly Val Pro Leu Pro Leu Ser Ile Gln Trp His<br>445                         450                         455 | 1396 |
| tgg cgg ccc tgg aca ccc tgc aag atg ttt gcc cag cgt agt ctc cgg<br>Trp Arg Pro Trp Thr Pro Cys Lys Met Phe Ala Gln Arg Ser Leu Arg<br>460                         465                         470                   475 | 1444 |
| cgg cgg cag cag caa gac ctc atg cca cag tgc cgt gac tgg agg gcg<br>Arg Arg Gln Gln Gln Asp Leu Met Pro Gln Cys Arg Asp Trp Arg Ala | 1492 |

```
                        480                 485                 490
gtg acc acg cag gat gcc gtg aac ccc atc gag agc ctg gac acc tgg         1540
Val Thr Thr Gln Asp Ala Val Asn Pro Ile Glu Ser Leu Asp Thr Trp
            495                 500                 505 acc gag ttt gtg gag gga aag aat aag act gtg agc aag ctg gtg atc         1588
Thr Glu Phe Val Glu Gly Lys Asn Lys Thr Val Ser Lys Leu Val Ile
        510                 515                 520 cag aat gcc aac gtg tct gcc atg tac aag tgt gtg gtc tcc aac aag         1636
Gln Asn Ala Asn Val Ser Ala Met Tyr Lys Cys Val Val Ser Asn Lys
    525                 530                 535 gtg ggc cag gat gag cgg ctc atc tac ttc tat gtg acc acc atc ccc         1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc         1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat         1780
Gln Pro Val Leu Leu Ser Cys Gln Ala Asp Ser Tyr Lys Tyr Glu His
            575                 580                 585 ctg cgc tgg tac cgc ctc aac ctg tcc acg ctg cac gat gcg cac ggg         1828
Leu Arg Trp Tyr Arg Leu Asn Leu Ser Thr Leu His Asp Ala His Gly
        590                 595                 600 aac ccg ctt ctg ctc gac tgc aag aac gtg cat ctg ttc gcc acc cct         1876
Asn Pro Leu Leu Leu Asp Cys Lys Asn Val His Leu Phe Ala Thr Pro
    605                 610                 615 ctg gcc gcc agc ctg gag gag gtg gca cct ggg gcg cgc cac gcc acg         1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat         1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag         2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac         2068
Lys Tyr Leu Ser Val Gln Ala Leu Glu Ala Pro Arg Leu Thr Gln Asn
        670                 675                 680 ttg acc gac ctc ctg gtg aac gtg agc gac tcg ctg gag atg cag tgc         2116
Leu Thr Asp Leu Leu Val Asn Val Ser Asp Ser Leu Glu Met Gln Cys
    685                 690                 695 ttg gtg gcc gga gcg cac gcg ccc agc atc gtg tgg tac aaa gac gag         2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag         2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg         2260
Lys Leu Ser Ile Gln Arg Val Arg Glu Glu Asp Ala Gly Arg Tyr Leu
            735                 740                 745 tgc agc gtg tgc aac gcc aag ggc tgc gtc aac tcc tcc gcc agc gtg         2308
Cys Ser Val Cys Asn Ala Lys Gly Cys Val Asn Ser Ser Ala Ser Val
        750                 755                 760 gcc gtg gaa ggc tcc gag gat aag ggc agc atg gag atc gtg atc ctt         2356
Ala Val Glu Gly Ser Glu Asp Lys Gly Ser Met Glu Ile Val Ile Leu
    765                 770                 775 gtc ggt acc ggc gtc atc gct gtc ttc ttc tgg gtc ctc ctc ctc ctc         2404
Val Gly Thr Gly Val Ile Ala Val Phe Phe Trp Val Leu Leu Leu Leu
780                 785                 790                 795 atc ttc tgt aac atg agg agg ccg gcc cac gca gac atc aag acg ggc         2452
```

|   |   |
|---|---|
| Ile Phe Cys Asn Met Arg Arg Pro Ala His Ala Asp Ile Lys Thr Gly<br>              800                        805                810 |   |
| tac ctg tcc atc atc atg gac ccc ggg gag gtg cct ctg gag gag caa<br>Tyr Leu Ser Ile Ile Met Asp Pro Gly Glu Val Pro Leu Glu Glu Gln<br>          815                        820                      825 | 2500 |
| tgc gaa tac ctg tcc tac gat gcc agc cag tgg gaa ttc ccc cga gag<br>Cys Glu Tyr Leu Ser Tyr Asp Ala Ser Gln Trp Glu Phe Pro Arg Glu<br>          830                        835                      840 | 2548 |
| cgg ctg cac ctg ggg aga gtg ctc ggc tac ggc gcc ttc ggg aag gtg<br>Arg Leu His Leu Gly Arg Val Leu Gly Tyr Gly Ala Phe Gly Lys Val<br>845                       850                       855 | 2596 |
| gtg gaa gcc tcc gct ttc ggc atc cac aag ggc agc agc tgt gac acc<br>Val Glu Ala Ser Ala Phe Gly Ile His Lys Gly Ser Ser Cys Asp Thr<br>860                       865                       870                   875 | 2644 |
| gtg gcc gtg aaa atg ctg aaa gag ggc gcc acg gcc agc gag cac cgc<br>Val Ala Val Lys Met Leu Lys Glu Gly Ala Thr Ala Ser Glu His Arg<br>                      880                       885                      890 | 2692 |
| gcg ctg atg tcg gag ctc aag atc ctc att cac atc ggc aac cac ctc<br>Ala Leu Met Ser Glu Leu Lys Ile Leu Ile His Ile Gly Asn His Leu<br>          895                        900                      905 | 2740 |
| aac gtg gtc aac ctc ctc ggg gcg tgc acc aag ccg cag ggc ccc ctc<br>Asn Val Val Asn Leu Leu Gly Ala Cys Thr Lys Pro Gln Gly Pro Leu<br>              910                       915                      920 | 2788 |
| atg gtg atc gtg gag ttc tgc aag tac ggc aac ctc tcc aac ttc ctg<br>Met Val Ile Val Glu Phe Cys Lys Tyr Gly Asn Leu Ser Asn Phe Leu<br>925                       930                       935 | 2836 |
| cgc gcc aag cgg gac gcc ttc agc ccc tgc gcg gag aag tct ccc gag<br>Arg Ala Lys Arg Asp Ala Phe Ser Pro Cys Ala Glu Lys Ser Pro Glu<br>940                       945                       950                   955 | 2884 |
| cag cgc gga cgc ttc cgc gcc atg gtg gag ctc gcc agg ctg gat cgg<br>Gln Arg Gly Arg Phe Arg Ala Met Val Glu Leu Ala Arg Leu Asp Arg<br>              960                       965                      970 | 2932 |
| agg cgg ccg ggg agc agc gac agg gtc ctc ttc gcg cgg ttc tcg aag<br>Arg Arg Pro Gly Ser Ser Asp Arg Val Leu Phe Ala Arg Phe Ser Lys<br>          975                        980                      985 | 2980 |
| acc gag ggc gga gcg agg cgg gct tct cca gac caa gaa gct gag gac<br>Thr Glu Gly Gly Ala Arg Arg Ala Ser Pro Asp Gln Glu Ala Glu Asp<br>          990                        995                     1000 | 3028 |
| ctg tgg ctg agc ccg ctg acc atg gaa gat ctt gtc tgc tac agc<br>Leu Trp Leu Ser Pro Leu Thr Met Glu Asp Leu Val Cys Tyr Ser<br>1005                      1010                   1015 | 3073 |
| ttc cag gtg gcc aga ggg atg gag ttc ctg gct tcc cga aag tgc<br>Phe Gln Val Ala Arg Gly Met Glu Phe Leu Ala Ser Arg Lys Cys<br>1020                      1025                   1030 | 3118 |
| atc cac aga gac ctg gct gct cgg aac att ctg ctg tcg gaa agc<br>Ile His Arg Asp Leu Ala Ala Arg Asn Ile Leu Leu Ser Glu Ser<br>1035                      1040                   1045 | 3163 |
| gac gtg gtg aag atc tgt gac ttt ggc ctt gcc cgg gac atc tac<br>Asp Val Val Lys Ile Cys Asp Phe Gly Leu Ala Arg Asp Ile Tyr<br>1050                      1055                   1060 | 3208 |
| aaa gac cct gac tac gtc cgc aag ggc agt gcc cgg ctg ccc ctg<br>Lys Asp Pro Asp Tyr Val Arg Lys Gly Ser Ala Arg Leu Pro Leu<br>1065                      1070                   1075 | 3253 |
| aag tgg atg gcc cct gaa agc atc ttc gac aag gtg tac acc acg<br>Lys Trp Met Ala Pro Glu Ser Ile Phe Asp Lys Val Tyr Thr Thr<br>1080                      1085                   1090 | 3298 |
| cag agt gac gtg tgg tcc ttt ggg gtg ctt ctc tgg gag atc ttc<br>Gln Ser Asp Val Trp Ser Phe Gly Val Leu Leu Trp Glu Ile Phe<br>1095                      1100                   1105 | 3343 |

| | | | | | | | | | | |
|---|---|---|---|---|---|---|---|---|---|---|
| tct | ctg | ggg | gcc | tcc | ccg | tac | cct | ggg | gtg | cag | atc | aat | gag | gag | 3388 |
| Ser | Leu | Gly | Ala | Ser | Pro | Tyr | Pro | Gly | Val | Gln | Ile | Asn | Glu | Glu |
| | 1110 | | | | 1115 | | | | 1120 | | | | | |

| ttc | tgc | cag | cgg | ctg | aga | gac | ggc | aca | agg | atg | agg | gcc | ccg | gag | 3433 |
|---|---|---|---|---|---|---|---|---|---|---|---|---|---|---|---|
| Phe | Cys | Gln | Arg | Leu | Arg | Asp | Gly | Thr | Arg | Met | Arg | Ala | Pro | Glu |
| 1125 | | | | | 1130 | | | | | 1135 | | | | |

| ctg | gcc | act | ccc | gcc | ata | cgc | cgc | atc | atg | ctg | aac | tgc | tgg | tcc | 3478 |
|---|---|---|---|---|---|---|---|---|---|---|---|---|---|---|---|
| Leu | Ala | Thr | Pro | Ala | Ile | Arg | Arg | Ile | Met | Leu | Asn | Cys | Trp | Ser |
| 1140 | | | | | 1145 | | | | | 1150 | | | | |

| gga | gac | ccc | aag | gcg | aga | cct | gca | ttc | tcg | gag | ctg | gtg | gag | atc | 3523 |
|---|---|---|---|---|---|---|---|---|---|---|---|---|---|---|---|
| Gly | Asp | Pro | Lys | Ala | Arg | Pro | Ala | Phe | Ser | Glu | Leu | Val | Glu | Ile |
| 1155 | | | | | 1160 | | | | | 1165 | | | | |

| ctg | ggg | gac | ctg | ctc | cag | ggc | agg | ggc | ctg | caa | gag | gaa | gag | gag | 3568 |
|---|---|---|---|---|---|---|---|---|---|---|---|---|---|---|---|
| Leu | Gly | Asp | Leu | Leu | Gln | Gly | Arg | Gly | Leu | Gln | Glu | Glu | Glu | Glu |
| 1170 | | | | | 1175 | | | | | 1180 | | | | |

| gtc | tgc | atg | gcc | ccg | cgc | agc | tct | cag | agc | tca | gaa | gag | ggc | agc | 3613 |
|---|---|---|---|---|---|---|---|---|---|---|---|---|---|---|---|
| Val | Cys | Met | Ala | Pro | Arg | Ser | Ser | Gln | Ser | Ser | Glu | Glu | Gly | Ser |
| 1185 | | | | | 1190 | | | | | 1195 | | | | |

| ttc | tcg | cag | gtg | tcc | acc | atg | gcc | cta | cac | atc | gcc | cag | gct | gac | 3658 |
|---|---|---|---|---|---|---|---|---|---|---|---|---|---|---|---|
| Phe | Ser | Gln | Val | Ser | Thr | Met | Ala | Leu | His | Ile | Ala | Gln | Ala | Asp |
| 1200 | | | | | 1205 | | | | | 1210 | | | | |

| gct | gag | gac | agc | ccg | cca | agc | ctg | cag | cgc | cac | agc | ctg | gcc | gcc | 3703 |
|---|---|---|---|---|---|---|---|---|---|---|---|---|---|---|---|
| Ala | Glu | Asp | Ser | Pro | Pro | Ser | Leu | Gln | Arg | His | Ser | Leu | Ala | Ala |
| 1215 | | | | | 1220 | | | | | 1225 | | | | |

| agg | tat | tac | aac | tgg | gtg | tcc | ttt | ccc | ggg | tgc | ctg | gcc | aga | ggg | 3748 |
|---|---|---|---|---|---|---|---|---|---|---|---|---|---|---|---|
| Arg | Tyr | Tyr | Asn | Trp | Val | Ser | Phe | Pro | Gly | Cys | Leu | Ala | Arg | Gly |
| 1230 | | | | | 1235 | | | | | 1240 | | | | |

| gct | gag | acc | cgt | ggt | tcc | tcc | agg | atg | aag | aca | ttt | gag | gaa | ttc | 3793 |
|---|---|---|---|---|---|---|---|---|---|---|---|---|---|---|---|
| Ala | Glu | Thr | Arg | Gly | Ser | Ser | Arg | Met | Lys | Thr | Phe | Glu | Glu | Phe |
| 1245 | | | | | 1250 | | | | | 1255 | | | | |

| ccc | atg | acc | cca | acg | acc | tac | aaa | ggc | tct | gtg | gac | aac | cag | aca | 3838 |
|---|---|---|---|---|---|---|---|---|---|---|---|---|---|---|---|
| Pro | Met | Thr | Pro | Thr | Thr | Tyr | Lys | Gly | Ser | Val | Asp | Asn | Gln | Thr |
| 1260 | | | | | 1265 | | | | | 1270 | | | | |

| gac | agt | ggg | atg | gtg | ctg | gcc | tcg | gag | gag | ttt | gag | cag | ata | gag | 3883 |
|---|---|---|---|---|---|---|---|---|---|---|---|---|---|---|---|
| Asp | Ser | Gly | Met | Val | Leu | Ala | Ser | Glu | Glu | Phe | Glu | Gln | Ile | Glu |
| 1275 | | | | | 1280 | | | | | 1285 | | | | |

| agc | agg | cat | aga | caa | gaa | agc | ggc | ttc | agg | tagctgaagc agagagagag | 3933 |
|---|---|---|---|---|---|---|---|---|---|---|---|
| Ser | Arg | His | Arg | Gln | Glu | Ser | Gly | Phe | Arg | | |
| 1290 | | | | | 1295 | | | | | | | aaggcagcat acgtcagcat tttcttctct gcacttataa gaaagatcaa agactttaag  3993 actttcgcta tttcttctac tgctatctac tacaaacttc aaagaggaac caggaggaca  4053 agaggagcat gaaagtggac aaggagtgtg accactgaag caccacaggg aaggggttag  4113 gcctccggat gactgcgggc aggcctggat aatatccagc ctcccacaag aagctggtgg  4173 agcagagtgt tccctgactc ct  4195

<210> SEQ ID NO 53
<211> LENGTH: 1298
<212> TYPE: PRT
<213> ORGANISM: Homo sapiens

<400> SEQUENCE: 53

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
50                   55                  60

Gln Glu Ala Pro Ala Thr Gly Asp Lys Asp Ser Glu Asp Thr Gly Val
65              70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Tyr Pro Pro Pro Glu Phe Gln Trp
        355                 360                 365

Tyr Lys Asp Gly Lys Ala Leu Ser Gly Arg His Ser Pro His Ala Leu
370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
450                 455                 460

Pro Cys Lys Met Phe Ala Gln Arg Ser Leu Arg Arg Arg Gln Gln Gln

```
            465                 470                 475                 480
        Asp Leu Met Pro Gln Cys Arg Asp Trp Arg Ala Val Thr Thr Gln Asp
                        485                 490                 495
        Ala Val Asn Pro Ile Glu Ser Leu Asp Thr Trp Thr Glu Phe Val Glu
                        500                 505                 510
        Gly Lys Asn Lys Thr Val Ser Lys Leu Val Ile Gln Asn Ala Asn Val
                        515                 520                 525
        Ser Ala Met Tyr Lys Cys Val Val Ser Asn Lys Val Gly Gln Asp Glu
                        530                 535                 540
        Arg Leu Ile Tyr Phe Tyr Val Thr Thr Ile Pro Asp Gly Phe Thr Ile
        545                 550                 555                 560
        Glu Ser Lys Pro Ser Glu Glu Leu Leu Glu Gly Gln Pro Val Leu Leu
                        565                 570                 575
        Ser Cys Gln Ala Asp Ser Tyr Lys Tyr Glu His Leu Arg Trp Tyr Arg
                        580                 585                 590
        Leu Asn Leu Ser Thr Leu His Asp Ala His Gly Asn Pro Leu Leu Leu
                        595                 600                 605
        Asp Cys Lys Asn Val His Leu Phe Ala Thr Pro Leu Ala Ala Ser Leu
                        610                 615                 620
        Glu Glu Val Ala Pro Gly Ala Arg His Ala Thr Leu Ser Leu Ser Ile
        625                 630                 635                 640
        Pro Arg Val Ala Pro Glu His Glu Gly His Tyr Val Cys Glu Val Gln
                        645                 650                 655
        Asp Arg Arg Ser His Asp Lys His Cys His Lys Lys Tyr Leu Ser Val
                        660                 665                 670
        Gln Ala Leu Glu Ala Pro Arg Leu Thr Gln Asn Leu Thr Asp Leu Leu
                        675                 680                 685
        Val Asn Val Ser Asp Ser Leu Glu Met Gln Cys Leu Val Ala Gly Ala
                        690                 695                 700
        His Ala Pro Ser Ile Val Trp Tyr Lys Asp Glu Arg Leu Leu Glu Glu
        705                 710                 715                 720
        Lys Ser Gly Val Asp Leu Ala Asp Ser Asn Gln Lys Leu Ser Ile Gln
                        725                 730                 735
        Arg Val Arg Glu Glu Asp Ala Gly Arg Tyr Leu Cys Ser Val Cys Asn
                        740                 745                 750
        Ala Lys Gly Cys Val Asn Ser Ser Ala Ser Val Ala Val Glu Gly Ser
                        755                 760                 765
        Glu Asp Lys Gly Ser Met Glu Ile Val Ile Leu Val Gly Thr Gly Val
                        770                 775                 780
        Ile Ala Val Phe Phe Trp Val Leu Leu Leu Leu Ile Phe Cys Asn Met
        785                 790                 795                 800
        Arg Arg Pro Ala His Ala Asp Ile Lys Thr Gly Tyr Leu Ser Ile Ile
                        805                 810                 815
        Met Asp Pro Gly Glu Val Pro Leu Glu Glu Gln Cys Glu Tyr Leu Ser
                        820                 825                 830
        Tyr Asp Ala Ser Gln Trp Glu Phe Pro Arg Glu Arg Leu His Leu Gly
                        835                 840                 845
        Arg Val Leu Gly Tyr Gly Ala Phe Gly Lys Val Val Glu Ala Ser Ala
                        850                 855                 860
        Phe Gly Ile His Lys Gly Ser Ser Cys Asp Thr Val Ala Val Lys Met
        865                 870                 875                 880
        Leu Lys Glu Gly Ala Thr Ala Ser Glu His Arg Ala Leu Met Ser Glu
                        885                 890                 895
```

```
Leu Lys Ile Leu Ile His Ile Gly Asn His Leu Asn Val Val Asn Leu
        900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
        930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                965                 970                 975

Ser Asp Arg Val Leu Phe Ala Arg Phe Ser Lys Thr Glu Gly Gly Ala
        980                 985                 990

Arg Arg Ala Ser Pro Asp Gln Glu Ala Glu Asp Leu Trp Leu Ser Pro
        995                 1000                1005

Leu Thr Met Glu Asp Leu Val Cys Tyr Ser Phe Gln Val Ala Arg
   1010                 1015                1020

Gly Met Glu Phe Leu Ala Ser Arg Lys Cys Ile His Arg Asp Leu
   1025                 1030                1035

Ala Ala Arg Asn Ile Leu Leu Ser Glu Ser Asp Val Val Lys Ile
   1040                 1045                1050

Cys Asp Phe Gly Leu Ala Arg Asp Ile Tyr Lys Asp Pro Asp Tyr
   1055                 1060                1065

Val Arg Lys Gly Ser Ala Arg Leu Pro Leu Lys Trp Met Ala Pro
   1070                 1075                1080

Glu Ser Ile Phe Asp Lys Val Tyr Thr Thr Gln Ser Asp Val Trp
   1085                 1090                1095

Ser Phe Gly Val Leu Leu Trp Glu Ile Phe Ser Leu Gly Ala Ser
   1100                 1105                1110

Pro Tyr Pro Gly Val Gln Ile Asn Glu Glu Phe Cys Gln Arg Leu
   1115                 1120                1125

Arg Asp Gly Thr Arg Met Arg Ala Pro Glu Leu Ala Thr Pro Ala
   1130                 1135                1140

Ile Arg Arg Ile Met Leu Asn Cys Trp Ser Gly Asp Pro Lys Ala
   1145                 1150                1155

Arg Pro Ala Phe Ser Glu Leu Val Glu Ile Leu Gly Asp Leu Leu
   1160                 1165                1170

Gln Gly Arg Gly Leu Gln Glu Glu Glu Val Cys Met Ala Pro
   1175                 1180                1185

Arg Ser Ser Gln Ser Ser Glu Glu Gly Ser Phe Ser Gln Val Ser
   1190                 1195                1200

Thr Met Ala Leu His Ile Ala Gln Ala Asp Ala Glu Asp Ser Pro
   1205                 1210                1215

Pro Ser Leu Gln Arg His Ser Leu Ala Ala Arg Tyr Tyr Asn Trp
   1220                 1225                1230

Val Ser Phe Pro Gly Cys Leu Ala Arg Gly Ala Glu Thr Arg Gly
   1235                 1240                1245

Ser Ser Arg Met Lys Thr Phe Glu Glu Phe Pro Met Thr Pro Thr
   1250                 1255                1260

Thr Tyr Lys Gly Ser Val Asp Asn Gln Thr Asp Ser Gly Met Val
   1265                 1270                1275

Leu Ala Ser Glu Glu Phe Glu Gln Ile Glu Ser Arg His Arg Gln
   1280                 1285                1290
```

```
Glu Ser Gly Phe Arg
    1295

<210> SEQ ID NO 54
<211> LENGTH: 4795
<212> TYPE: DNA
<213> ORGANISM: Homo sapiens
<220> FEATURE:
<221> NAME/KEY: CDS
<222> LOCATION: (20)..(4111)

<400> SEQUENCE: 54
ccacgcgcag cggccggag atg cag cgg ggc gcc gcg ctg tgc ctg cga ctg        52
                    Met Gln Arg Gly Ala Ala Leu Cys Leu Arg Leu
                     1               5                      10 tgg ctc tgc ctg gga ctc ctg gac ggc ctg gtg agt ggc tac tcc atg        100
Trp Leu Cys Leu Gly Leu Leu Asp Gly Leu Val Ser Gly Tyr Ser Met
            15                  20                  25 acc ccc ccg acc ttg aac atc acg gag gag tca cac gtc atc gac acc        148
Thr Pro Pro Thr Leu Asn Ile Thr Glu Glu Ser His Val Ile Asp Thr
        30                  35                  40 ggt gac agc ctg tcc atc tcc tgc agg gga cag cac ccc ctc gag tgg        196
Gly Asp Ser Leu Ser Ile Ser Cys Arg Gly Gln His Pro Leu Glu Trp
    45                  50                  55 gct tgg cca gga gct cag gag gcg cca gcc acc gga gac aag gac agc        244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc        292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc        340
Tyr Cys Lys Val Leu Leu Leu His Glu Val His Ala Asn Asp Thr Gly
            95                  100                 105 agc tac gtc tgc tac tac aag tac atc aag gca cgc atc gag ggc acc        388
Ser Tyr Val Cys Tyr Tyr Lys Tyr Ile Lys Ala Arg Ile Glu Gly Thr
        110                 115                 120 acg gcc gcc agc tcc tac gtg ttc gtg aga gac ttt gag cag cca ttc        436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg        484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg        532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac        580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac        628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc        676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg        724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac        772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac        820
```

|  |  |  |  |  |  |  |  |  |  |  |  |  |
|---|---|---|---|---|---|---|---|---|---|---|---|---|
| Cys | Thr | Val | Trp | Ala | Glu | Phe | Asn | Ser | Gly | Val | Thr | Phe | Asp | Trp | Asp |
|  |  |  | 255 |  |  |  | 260 |  |  |  | 265 |  |

```
tac cca ggg aag cag gca gag cgg ggt aag tgg gtg ccc gag cga cgc    868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac    916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc    964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc    1012
Ile Gln Arg Phe Arg Glu Ser Thr Glu Val Ile Val His Glu Asn Pro
            320                 325                 330 ttc atc agc gtc gag tgg ctc aaa gga ccc atc ctg gag gcc acg gca    1060
Phe Ile Ser Val Glu Trp Leu Lys Gly Pro Ile Leu Glu Ala Thr Ala
        335                 340                 345 gga gac gag ctg gtg aag ctg ccc gtg aag ctg gca gcg tac ccc ccg    1108
Gly Asp Glu Leu Val Lys Leu Pro Val Lys Leu Ala Ala Tyr Pro Pro
    350                 355                 360 ccc gag ttc cag tgg tac aag gat gga aag gca ctg tcc ggg cgc cac    1156
Pro Glu Phe Gln Trp Tyr Lys Asp Gly Lys Ala Leu Ser Gly Arg His
365                 370                 375 agt cca cat gcc ctg gtg ctc aag gag gtg aca gag gcc agc aca ggc    1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac    1252
Thr Tyr Thr Leu Ala Leu Trp Asn Ser Ala Ala Gly Leu Arg Arg Asn
            400                 405                 410 atc agc ctg gag ctg gtg gtg aat gtg ccc ccc cag ata cat gag aag    1300
Ile Ser Leu Glu Leu Val Val Asn Val Pro Pro Gln Ile His Glu Lys
        415                 420                 425 gag gcc tcc tcc ccc agc atc tac tcg cgt cac agc cgc cag gcc ctc    1348
Glu Ala Ser Ser Pro Ser Ile Tyr Ser Arg His Ser Arg Gln Ala Leu
    430                 435                 440 acc tgc acg gcc tac ggg gtg ccc ctg cct ctc agc atc cag tgg cac    1396
Thr Cys Thr Ala Tyr Gly Val Pro Leu Pro Leu Ser Ile Gln Trp His
445                 450                 455 tgg cgg ccc tgg aca ccc tgc aag atg ttt gcc cag cgt agt ctc cgg    1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg    1492
Arg Arg Gln Gln Gln Asp Leu Met Pro Gln Cys Arg Asp Trp Arg Ala
            480                 485                 490 gtg acc acg cag gat gcc gtg aac ccc atc gag agc ctg gac acc tgg    1540
Val Thr Thr Gln Asp Ala Val Asn Pro Ile Glu Ser Leu Asp Thr Trp
        495                 500                 505 acc gag ttt gtg gag gga aag aat aag act gtg agc aag ctg gtg atc    1588
Thr Glu Phe Val Glu Gly Lys Asn Lys Thr Val Ser Lys Leu Val Ile
    510                 515                 520 cag aat gcc aac gtg tct gcc atg tac aag tgt gtg gtc tcc aac aag    1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc    1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc    1732
Asp Gly Phe Thr Ile Glu Ser Lys Pro Ser Glu Glu Leu Leu Glu Gly
            560                 565                 570
```

-continued

| | |
|---|---|
| cag ccg gtg ctc ctg agc tgc caa gcc gac agc tac aag tac gag cat<br>Gln Pro Val Leu Leu Ser Cys Gln Ala Asp Ser Tyr Lys Tyr Glu His<br>575 580 585 | 1780 |
| ctg cgc tgg tac cgc ctc aac ctg tcc acg ctg cac gat gcg cac ggg<br>Leu Arg Trp Tyr Arg Leu Asn Leu Ser Thr Leu His Asp Ala His Gly<br>590 595 600 | 1828 |
| aac ccg ctt ctg ctc gac tgc aag aac gtg cat ctg ttc gcc acc cct<br>Asn Pro Leu Leu Leu Asp Cys Lys Asn Val His Leu Phe Ala Thr Pro<br>605 610 615 | 1876 |
| ctg gcc gcc agc ctg gag gag gtg gca cct ggg gcg cgc cac gcc acg<br>Leu Ala Ala Ser Leu Glu Glu Val Ala Pro Gly Ala Arg His Ala Thr<br>620 625 630 635 | 1924 |
| ctc agc ctg agt atc ccc cgc gtc gcg ccc gag cac gag ggc cac tat<br>Leu Ser Leu Ser Ile Pro Arg Val Ala Pro Glu His Glu Gly His Tyr<br>640 645 650 | 1972 |
| gtg tgc gaa gtg caa gac cgg cgc agc cat gac aag cac tgc cac aag<br>Val Cys Glu Val Gln Asp Arg Arg Ser His Asp Lys His Cys His Lys<br>655 660 665 | 2020 |
| aag tac ctg tcg gtg cag gcc ctg gaa gcc cct cgg ctc acg cag aac<br>Lys Tyr Leu Ser Val Gln Ala Leu Glu Ala Pro Arg Leu Thr Gln Asn<br>670 675 680 | 2068 |
| ttg acc gac ctc ctg gtg aac gtg agc gac tcg ctg gag atg cag tgc<br>Leu Thr Asp Leu Leu Val Asn Val Ser Asp Ser Leu Glu Met Gln Cys<br>685 690 695 | 2116 |
| ttg gtg gcc gga gcg cac gcg ccc agc atc gtg tgg tac aaa gac gag<br>Leu Val Ala Gly Ala His Ala Pro Ser Ile Val Trp Tyr Lys Asp Glu<br>700 705 710 715 | 2164 |
| agg ctg ctg gag gaa aag tct gga gtc gac ttg gcg gac tcc aac cag<br>Arg Leu Leu Glu Glu Lys Ser Gly Val Asp Leu Ala Asp Ser Asn Gln<br>720 725 730 | 2212 |
| aag ctg agc atc cag cgc gtg cgc gag gag gat gcg gga cgc tat ctg<br>Lys Leu Ser Ile Gln Arg Val Arg Glu Glu Asp Ala Gly Arg Tyr Leu<br>735 740 745 | 2260 |
| tgc agc gtg tgc aac gcc aag ggc tgc gtc aac tcc tcc gcc agc gtg<br>Cys Ser Val Cys Asn Ala Lys Gly Cys Val Asn Ser Ser Ala Ser Val<br>750 755 760 | 2308 |
| gcc gtg gaa ggc tcc gag gat aag ggc agc atg gag atc gtg atc ctt<br>Ala Val Glu Gly Ser Glu Asp Lys Gly Ser Met Glu Ile Val Ile Leu<br>765 770 775 | 2356 |
| gtc ggt acc ggc gtc atc gct gtc ttc ttc tgg gtc ctc ctc ctc<br>Val Gly Thr Gly Val Ile Ala Val Phe Phe Trp Val Leu Leu Leu Leu<br>780 785 790 795 | 2404 |
| atc ttc tgt aac atg agg agg ccg gcc cac gca gac atc aag acg ggc<br>Ile Phe Cys Asn Met Arg Arg Pro Ala His Ala Asp Ile Lys Thr Gly<br>800 805 810 | 2452 |
| tac ctg tcc atc atc atg gac ccc ggg gag gtg cct ctg gag gag caa<br>Tyr Leu Ser Ile Ile Met Asp Pro Gly Glu Val Pro Leu Glu Glu Gln<br>815 820 825 | 2500 |
| tgc gaa tac ctg tcc tac gat gcc agc cag tgg gaa ttc ccc cga gag<br>Cys Glu Tyr Leu Ser Tyr Asp Ala Ser Gln Trp Glu Phe Pro Arg Glu<br>830 835 840 | 2548 |
| cgg ctg cac ctg ggg aga gtc ctc ggc tac ggc gcc ttc ggg aag gtg<br>Arg Leu His Leu Gly Arg Val Leu Gly Tyr Gly Ala Phe Gly Lys Val<br>845 850 855 | 2596 |
| gtg gaa gcc tcc gct ttc ggc atc cac aag ggc agc agc tgt gac acc<br>Val Glu Ala Ser Ala Phe Gly Ile His Lys Gly Ser Ser Cys Asp Thr<br>860 865 870 875 | 2644 |
| gtg gcc gtg aaa atg ctg aaa gag ggc gcc acg gcc agc gag cac cgc<br>Val Ala Val Lys Met Leu Lys Glu Gly Ala Thr Ala Ser Glu His Arg<br>880 885 890 | 2692 |

-continued

| | |
|---|---|
| gcg ctg atg tcg gag ctc aag atc ctc att cac atc ggc aac cac ctc<br>Ala Leu Met Ser Glu Leu Lys Ile Leu Ile His Ile Gly Asn His Leu<br>              895                      900                    905 | 2740 |
| aac gtg gtc aac ctc ctc ggg gcg tgc acc aag ccg cag ggc ccc ctc<br>Asn Val Val Asn Leu Leu Gly Ala Cys Thr Lys Pro Gln Gly Pro Leu<br>910                      915                      920 | 2788 |
| atg gtg atc gtg gag ttc tgc aag tac ggc aac ctc tcc aac ttc ctg<br>Met Val Ile Val Glu Phe Cys Lys Tyr Gly Asn Leu Ser Asn Phe Leu<br>925                      930                      935 | 2836 |
| cgc gcc aag cgg gac gcc ttc agc ccc tgc gcg gag aag tct ccc gag<br>Arg Ala Lys Arg Asp Ala Phe Ser Pro Cys Ala Glu Lys Ser Pro Glu<br>940                      945                      950                    955 | 2884 |
| cag cgc gga cgc ttc cgc gcc atg gtg gag ctc gcc agg ctg gat cgg<br>Gln Arg Gly Arg Phe Arg Ala Met Val Glu Leu Ala Arg Leu Asp Arg<br>              960                      965                    970 | 2932 |
| agg cgg ccg ggg agc agc gac agg gtc ctc ttc gcg cgg ttc tcg aag<br>Arg Arg Pro Gly Ser Ser Asp Arg Val Leu Phe Ala Arg Phe Ser Lys<br>975                      980                      985 | 2980 |
| acc gag ggc gga gcg agg cgg gct tct cca gac caa gaa gct gag gac<br>Thr Glu Gly Gly Ala Arg Arg Ala Ser Pro Asp Gln Glu Ala Glu Asp<br>              990                      995                    1000 | 3028 |
| ctg tgg ctg agc ccg ctg acc atg gaa gat ctt gtc tgc tac agc<br>Leu Trp Leu Ser Pro Leu Thr Met Glu Asp Leu Val Cys Tyr Ser<br>1005                    1010                    1015 | 3073 |
| ttc cag gtg gcc aga ggg atg gag ttc ctg gct tcc cga aag tgc<br>Phe Gln Val Ala Arg Gly Met Glu Phe Leu Ala Ser Arg Lys Cys<br>1020                    1025                    1030 | 3118 |
| atc cac aga gac ctg gct gct cgg aac att ctg ctg tcg gaa agc<br>Ile His Arg Asp Leu Ala Ala Arg Asn Ile Leu Leu Ser Glu Ser<br>1035                    1040                    1045 | 3163 |
| gac gtg gtg aag atc tgt gac ttt ggc ctt gcc cgg gac atc tac<br>Asp Val Val Lys Ile Cys Asp Phe Gly Leu Ala Arg Asp Ile Tyr<br>1050                    1055                    1060 | 3208 |
| aaa gac cct gac tac gtc cgc aag ggc agt gcc cgg ctg ccc ctg<br>Lys Asp Pro Asp Tyr Val Arg Lys Gly Ser Ala Arg Leu Pro Leu<br>1065                    1070                    1075 | 3253 |
| aag tgg atg gcc cct gaa agc atc ttc gac aag gtg tac acc acg<br>Lys Trp Met Ala Pro Glu Ser Ile Phe Asp Lys Val Tyr Thr Thr<br>1080                    1085                    1090 | 3298 |
| cag agt gac gtg tgg tcc ttt ggg gtg ctt ctc tgg gag atc ttc<br>Gln Ser Asp Val Trp Ser Phe Gly Val Leu Leu Trp Glu Ile Phe<br>1095                    1100                    1105 | 3343 |
| tct ctg ggg gcc tcc ccg tac cct ggg gtg cag atc aat gag gag<br>Ser Leu Gly Ala Ser Pro Tyr Pro Gly Val Gln Ile Asn Glu Glu<br>1110                    1115                    1120 | 3388 |
| ttc tgc cag cgg ctg aga gac ggc aca agg atg agg gcc ccg gag<br>Phe Cys Gln Arg Leu Arg Asp Gly Thr Arg Met Arg Ala Pro Glu<br>1125                    1130                    1135 | 3433 |
| ctg gcc act ccc gcc ata cgc cgc atc atg ctg aac tgc tgg tcc<br>Leu Ala Thr Pro Ala Ile Arg Arg Ile Met Leu Asn Cys Trp Ser<br>1140                    1145                    1150 | 3478 |
| gga gac ccc aag gcg aga cct gca ttc tcg gag ctg gtg gag atc<br>Gly Asp Pro Lys Ala Arg Pro Ala Phe Ser Glu Leu Val Glu Ile<br>1155                    1160                    1165 | 3523 |
| ctg ggg gac ctg ctc cag ggc agg ggc ctg caa gag gaa gag gag<br>Leu Gly Asp Leu Leu Gln Gly Arg Gly Leu Gln Glu Glu Glu Glu<br>1170                    1175                    1180 | 3568 |
| gtc tgc atg gcc ccg cgc agc tct cag agc tca gaa gag ggc agc<br>Val Cys Met Ala Pro Arg Ser Ser Gln Ser Ser Glu Glu Gly Ser | 3613 |

-continued

```
              1185                1190                1195
ttc  tcg  cag  gtg  tcc  acc  atg  gcc  cta  cac  atc  gcc  cag  gct  gac       3658
Phe  Ser  Gln  Val  Ser  Thr  Met  Ala  Leu  His  Ile  Ala  Gln  Ala  Asp
     1200                1205                1210 gct  gag  gac  agc  ccg  cca  agc  ctg  cag  cgc  cac  agc  ctg  gcc  gcc       3703
Ala  Glu  Asp  Ser  Pro  Pro  Ser  Leu  Gln  Arg  His  Ser  Leu  Ala  Ala
     1215                1220                1225 agg  tat  tac  aac  tgg  gtg  tcc  ttt  ccc  ggg  tgc  ctg  gcc  aga  ggg       3748
Arg  Tyr  Tyr  Asn  Trp  Val  Ser  Phe  Pro  Gly  Cys  Leu  Ala  Arg  Gly
     1230                1235                1240 gct  gag  acc  cgt  ggt  tcc  tcc  agg  atg  aag  aca  ttt  gag  gaa  ttc       3793
Ala  Glu  Thr  Arg  Gly  Ser  Ser  Arg  Met  Lys  Thr  Phe  Glu  Glu  Phe
     1245                1250                1255 ccc  atg  acc  cca  acg  acc  tac  aaa  ggc  tct  gtg  gac  aac  cag  aca       3838
Pro  Met  Thr  Pro  Thr  Thr  Tyr  Lys  Gly  Ser  Val  Asp  Asn  Gln  Thr
     1260                1265                1270 gac  agt  ggg  atg  gtg  ctg  gcc  tcg  gag  gag  ttt  gag  cag  ata  gag       3883
Asp  Ser  Gly  Met  Val  Leu  Ala  Ser  Glu  Glu  Phe  Glu  Gln  Ile  Glu
     1275                1280                1285 agc  agg  cat  aga  caa  gaa  agc  ggc  ttc  agc  tgt  aaa  gga  cct  ggc       3928
Ser  Arg  His  Arg  Gln  Glu  Ser  Gly  Phe  Ser  Cys  Lys  Gly  Pro  Gly
     1290                1295                1300 cag  aat  gtg  gct  gtg  acc  agg  gca  cac  cct  gac  tcc  caa  ggg  agg       3973
Gln  Asn  Val  Ala  Val  Thr  Arg  Ala  His  Pro  Asp  Ser  Gln  Gly  Arg
     1305                1310                1315 cgg  cgg  cgg  cct  gag  cgg  ggg  gcc  cga  gga  ggc  cag  gtg  ttt  tac       4018
Arg  Arg  Arg  Pro  Glu  Arg  Gly  Ala  Arg  Gly  Gly  Gln  Val  Phe  Tyr
     1320                1325                1330 aac  agc  gag  tat  ggg  gag  ctg  tcg  gag  cca  agc  gag  gag  gac  cac       4063
Asn  Ser  Glu  Tyr  Gly  Glu  Leu  Ser  Glu  Pro  Ser  Glu  Glu  Asp  His
     1335                1340                1345 tgc  tcc  ccg  tct  gcc  cgc  gtg  act  ttc  ttc  aca  gac  aac  agc  tac       4108
Cys  Ser  Pro  Ser  Ala  Arg  Val  Thr  Phe  Phe  Thr  Asp  Asn  Ser  Tyr
     1350                1355                1360 taa gcagcatcgg acaagacccc cagcacttgg gggttcaggc ccggcagggc                      4161
gggcagaggg ctgaggcccc aggctgggaa ctcatctggt tgaactctgg tggcacagga              4221
gtgtcctctt ccctctctgc agacttccca gctaggaaga gcaggactcc aggcccaagg              4281
ctcccggaat tccgtcacca cgactggcca gggcacgctc cagctgcccc ggcccctccc              4341
cctgagattc agatgtcatt tagttcagca tccgcaggtg ctggtcccgg ggccagcact              4401
tccatgggaa tgtctctttg gcgacctcct ttcatcacac tgggtggtgg cctggtccct              4461
gttttcccac gaggaatctg tgggtctggg agtcacacag tgttggaggt taaggcatac              4521
gagagcagag gtctcccaaa cgcccttttcc tcctcaggca cacagctact ctccccacga             4581
gggctggctg gcctcaccca cccctgcaca gttgaaggga ggggctgtgt tccatctca               4641 aagaaggcat ttgcagggtc ctcttctggg cctgaccaaa cagccaacta gcccctgggg              4701
tggccaccag tatgacagta ttatacgctg gcaacacaga ggcagcccgc acacctgcgc              4761
ctgggtgttg agagccatcc tgcaagtctt tttc                                          4795
```

<210> SEQ ID NO 55
<211> LENGTH: 1363
<212> TYPE: PRT
<213> ORGANISM: Homo sapiens

<400> SEQUENCE: 55

Met Gln Arg Gly Ala Ala Leu Cys Leu Arg Leu Trp Leu Cys Leu Gly

```
             1               5                   10                  15
Leu Leu Asp Gly Leu Val Ser Gly Tyr Ser Met Thr Pro Pro Thr Leu
                    20                  25                  30

Asn Ile Thr Glu Glu Ser His Val Ile Asp Thr Gly Asp Ser Leu Ser
                    35                  40                  45

Ile Ser Cys Arg Gly Gln His Pro Leu Glu Trp Ala Trp Pro Gly Ala
                50                  55                  60

Gln Glu Ala Pro Ala Thr Gly Asp Lys Asp Ser Glu Asp Thr Gly Val
65                      70                  75                  80

Val Arg Asp Cys Glu Gly Thr Asp Ala Arg Pro Tyr Cys Lys Val Leu
                    85                  90                  95

Leu Leu His Glu Val His Ala Asn Asp Thr Gly Ser Tyr Val Cys Tyr
                    100                 105                 110

Tyr Lys Tyr Ile Lys Ala Arg Ile Glu Gly Thr Thr Ala Ala Ser Ser
                115                 120                 125

Tyr Val Phe Val Arg Asp Phe Glu Gln Pro Phe Ile Asn Lys Pro Asp
            130                 135                 140

Thr Leu Leu Val Asn Arg Lys Asp Ala Met Trp Val Pro Cys Leu Val
145                     150                 155                 160

Ser Ile Pro Gly Leu Asn Val Thr Leu Arg Ser Gln Ser Ser Val Leu
                    165                 170                 175

Trp Pro Asp Gly Gln Glu Val Val Trp Asp Asp Arg Arg Gly Met Leu
                    180                 185                 190

Val Ser Thr Pro Leu Leu His Asp Ala Leu Tyr Leu Gln Cys Glu Thr
                    195                 200                 205

Thr Trp Gly Asp Gln Asp Phe Leu Ser Asn Pro Phe Leu Val His Ile
                210                 215                 220

Thr Gly Asn Glu Leu Tyr Asp Ile Gln Leu Leu Pro Arg Lys Ser Leu
225                     230                 235                 240

Glu Leu Leu Val Gly Glu Lys Leu Val Leu Asn Cys Thr Val Trp Ala
                    245                 250                 255

Glu Phe Asn Ser Gly Val Thr Phe Asp Trp Asp Tyr Pro Gly Lys Gln
                260                 265                 270

Ala Glu Arg Gly Lys Trp Val Pro Glu Arg Arg Ser Gln Gln Thr His
                275                 280                 285

Thr Glu Leu Ser Ser Ile Leu Thr Ile His Asn Val Ser Gln His Asp
                290                 295                 300

Leu Gly Ser Tyr Val Cys Lys Ala Asn Asn Gly Ile Gln Arg Phe Arg
305                     310                 315                 320

Glu Ser Thr Glu Val Ile Val His Glu Asn Pro Phe Ile Ser Val Glu
                    325                 330                 335

Trp Leu Lys Gly Pro Ile Leu Glu Ala Thr Ala Gly Asp Glu Leu Val
                    340                 345                 350

Lys Leu Pro Val Lys Leu Ala Ala Tyr Pro Pro Pro Glu Phe Gln Trp
                    355                 360                 365

Tyr Lys Asp Gly Lys Ala Leu Ser Gly Arg His Ser Pro His Ala Leu
                    370                 375                 380

Val Leu Lys Glu Val Thr Glu Ala Ser Thr Gly Thr Tyr Thr Leu Ala
385                     390                 395                 400

Leu Trp Asn Ser Ala Ala Gly Leu Arg Arg Asn Ile Ser Leu Glu Leu
                    405                 410                 415

Val Val Asn Val Pro Pro Gln Ile His Glu Lys Glu Ala Ser Ser Pro
                    420                 425                 430
```

-continued

```
Ser Ile Tyr Ser Arg His Ser Arg Gln Ala Leu Thr Cys Thr Ala Tyr
            435                 440                 445
Gly Val Pro Leu Pro Leu Ser Ile Gln Trp His Trp Arg Pro Trp Thr
    450                 455                 460
Pro Cys Lys Met Phe Ala Gln Arg Ser Leu Arg Arg Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
            500                 505                 510
Gly Lys Asn Lys Thr Val Ser Lys Leu Val Ile Gln Asn Ala Asn Val
            515                 520                 525
Ser Ala Met Tyr Lys Cys Val Val Ser Asn Lys Val Gly Gln Asp Glu
        530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
            660                 665                 670
Gln Ala Leu Glu Ala Pro Arg Leu Thr Gln Asn Leu Thr Asp Leu Leu
        675                 680                 685
Val Asn Val Ser Asp Ser Leu Glu Met Gln Cys Leu Val Ala Gly Ala
690                 695                 700
His Ala Pro Ser Ile Val Trp Tyr Lys Asp Glu Arg Leu Leu Glu Glu
705                 710                 715                 720
Lys Ser Gly Val Asp Leu Ala Asp Ser Asn Gln Lys Leu Ser Ile Gln
                725                 730                 735
Arg Val Arg Glu Glu Asp Ala Gly Arg Tyr Leu Cys Ser Val Cys Asn
            740                 745                 750
Ala Lys Gly Cys Val Asn Ser Ser Ala Ser Val Ala Val Glu Gly Ser
        755                 760                 765
Glu Asp Lys Gly Ser Met Glu Ile Val Ile Leu Val Gly Thr Gly Val
    770                 775                 780
Ile Ala Val Phe Phe Trp Val Leu Leu Leu Ile Phe Cys Asn Met
785                 790                 795                 800
Arg Arg Pro Ala His Ala Asp Ile Lys Thr Gly Tyr Leu Ser Ile Ile
                805                 810                 815
Met Asp Pro Gly Glu Val Pro Leu Glu Glu Gln Cys Glu Tyr Leu Ser
            820                 825                 830
Tyr Asp Ala Ser Gln Trp Glu Phe Pro Arg Glu Arg Leu His Leu Gly
        835                 840                 845
```

Arg Val Leu Gly Tyr Gly Ala Phe Gly Lys Val Val Glu Ala Ser Ala
    850             855             860

Phe Gly Ile His Lys Gly Ser Ser Cys Asp Thr Val Ala Val Lys Met
865             870             875             880

Leu Lys Glu Gly Ala Thr Ala Ser Glu His Arg Ala Leu Met Ser Glu
            885             890             895

Leu Lys Ile Leu Ile His Ile Gly Asn His Leu Asn Val Val Asn Leu
            900             905             910

Leu Gly Ala Cys Thr Lys Pro Gln Gly Pro Leu Met Val Ile Val Glu
            915             920             925

Phe Cys Lys Tyr Gly Asn Leu Ser Asn Phe Leu Arg Ala Lys Arg Asp
930             935             940

Ala Phe Ser Pro Cys Ala Glu Lys Ser Pro Glu Gln Arg Gly Arg Phe
945             950             955             960

Arg Ala Met Val Glu Leu Ala Arg Leu Asp Arg Arg Pro Gly Ser
            965             970             975

Ser Asp Arg Val Leu Phe Ala Arg Phe Ser Lys Thr Glu Gly Gly Ala
            980             985             990

Arg Arg Ala Ser Pro Asp Gln Glu Ala Glu Asp Leu Trp Leu Ser Pro
            995             1000            1005

Leu Thr Met Glu Asp Leu Val Cys Tyr Ser Phe Gln Val Ala Arg
    1010            1015            1020

Gly Met Glu Phe Leu Ala Ser Arg Lys Cys Ile His Arg Asp Leu
    1025            1030            1035

Ala Ala Arg Asn Ile Leu Leu Ser Glu Ser Asp Val Val Lys Ile
    1040            1045            1050

Cys Asp Phe Gly Leu Ala Arg Asp Ile Tyr Lys Asp Pro Asp Tyr
    1055            1060            1065

Val Arg Lys Gly Ser Ala Arg Leu Pro Leu Lys Trp Met Ala Pro
    1070            1075            1080

Glu Ser Ile Phe Asp Lys Val Tyr Thr Thr Gln Ser Asp Val Trp
    1085            1090            1095

Ser Phe Gly Val Leu Leu Trp Glu Ile Phe Ser Leu Gly Ala Ser
    1100            1105            1110

Pro Tyr Pro Gly Val Gln Ile Asn Glu Glu Phe Cys Gln Arg Leu
    1115            1120            1125

Arg Asp Gly Thr Arg Met Arg Ala Pro Glu Leu Ala Thr Pro Ala
    1130            1135            1140

Ile Arg Arg Ile Met Leu Asn Cys Trp Ser Gly Asp Pro Lys Ala
    1145            1150            1155

Arg Pro Ala Phe Ser Glu Leu Val Glu Ile Leu Gly Asp Leu Leu
    1160            1165            1170

Gln Gly Arg Gly Leu Gln Glu Glu Glu Val Cys Met Ala Pro
    1175            1180            1185

Arg Ser Ser Gln Ser Ser Glu Glu Gly Ser Phe Ser Gln Val Ser
    1190            1195            1200

Thr Met Ala Leu His Ile Ala Gln Ala Asp Ala Glu Asp Ser Pro
    1205            1210            1215

Pro Ser Leu Gln Arg His Ser Leu Ala Ala Arg Tyr Tyr Asn Trp
    1220            1225            1230

Val Ser Phe Pro Gly Cys Leu Ala Arg Gly Ala Glu Thr Arg Gly
    1235            1240            1245

Ser Ser Arg Met Lys Thr Phe Glu Glu Phe Pro Met Thr Pro Thr

```
                    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Glu Asp His Cys Ser Pro Ser Ala
    1340                1345                1350

Arg Val Thr Phe Phe Thr Asp Asn Ser Tyr
    1355                1360
```

<210> SEQ ID NO 56
<211> LENGTH: 132
<212> TYPE: PRT
<213> ORGANISM: Artificial Sequence
<220> FEATURE:
<223> OTHER INFORMATION: Synthetic peptide

<400> SEQUENCE: 56

```
Met Lys Leu Pro Val Arg Leu Leu Val Leu Met Phe Trp Ile Pro Ala
1               5                   10                  15

Ser Ser Ser Asp Phe Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Arg Thr Phe Gly Gly Gly Thr Lys Leu
        115                 120                 125

Glu Ile Lys Arg
    130
```

<210> SEQ ID NO 57
<211> LENGTH: 137
<212> TYPE: PRT
<213> ORGANISM: Artificial Sequence
<220> FEATURE:
<223> OTHER INFORMATION: Synthetic peptide

<400> SEQUENCE: 57

```
Met Gly Trp Ser Gly Val Phe Leu Phe Leu Leu Ser Gly Ser Thr Gly
1               5                   10                  15

Val His Ser Glu Ile Gln Leu Gln Gln Ser Gly Pro Asp Leu Val Lys
            20                  25                  30

Pro Gly Ala Ser Val Lys Val Ser Cys Arg Ala Ser Gly Tyr Ser Phe
        35                  40                  45
```

-continued

Thr Gly Tyr Asn Met Tyr Trp Val Lys Gln Ser His Gly Lys Ser Leu
 50                  55                  60

Glu Trp Ile Gly Tyr Ile Asp Pro Tyr Asn Gly Asp Thr Thr Tyr Asn
 65                  70                  75                  80

Gln Lys Phe Lys Gly Lys Ala Thr Leu Thr Val Asp Lys Ser Ser Ser
                 85                  90                  95

Thr Ala Phe Met His Leu Asn Ser Leu Thr Ser Glu Asp Ser Ala Val
             100                 105                 110

Tyr Tyr Cys Ala Arg Thr Ser Tyr Tyr Gly Gly Met Asp Tyr Trp Gly
         115                 120                 125

Gln Gly Thr Ser Val Thr Val Ser Ser
    130                 135

<210> SEQ ID NO 58
<211> LENGTH: 16
<212> TYPE: PRT
<213> ORGANISM: Artificial Sequence
<220> FEATURE:
<223> OTHER INFORMATION: Synthetic peptide

<400> SEQUENCE: 58

Arg Ser Ser Gln Ser Leu Val His Ser Asn Gly Asn Thr Tyr Leu His
 1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Lys Val Ser Asn Arg Phe Ser
 1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Ser Gln Ser Thr His Val Pro Arg Thr
 1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Gly Tyr Ser Phe Thr Gly Tyr Asn Met Tyr
 1               5                   10

<210> SEQ ID NO 62
<211> LENGTH: 17
<212> TYPE: PRT
<213> ORGANISM: Artificial Sequence
<220> FEATURE:
<223> OTHER INFORMATION: Synthetic peptide

<400> SEQUENCE: 62

```
Tyr Ile Asp Pro Tyr Asn Gly Asp Thr Thr Tyr Asn Gln Lys Phe Lys
1               5                   10                  15

Gly

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Thr Ser Tyr Tyr Gly Gly Met Asp Tyr
1               5
```

THERAPEUTIC COMPOSITIONS FOR THE TREATMENT OF DRY EYE DISEASE

FEDERALLY SPONSORED RESEARCH OR DEVELOPMENT

This invention was made with Government support under Grant No EY-12963 awarded by the National Institute of Health. The Government has certain rights in the invention.

FIELD OF THE INVENTION

This invention relates generally to the field of ophthalmology.

BACKGROUND OF THE INVENTION

Dry Eye Disease (DED) is a relatively common condition characterized by inadequate tear film protection of the cornea. Dry eye symptoms have traditionally been managed with eyelid hygiene, topical antibiotics (erythromycin or bacitracin ointments), oral tetracyclines (tetracycline, doxycycline, or minocycline), anti-inflammatory compounds (cyclosporine) and corticosteroids which are often time consuming, frustrating, and frequently ineffective or variably effective treatments.

Tens of millions of people (mostly women) are affected worldwide by dry eye. 10 million people in US are affected with severe dry eyes and more than 3.2 million women and 1.6 million men above the age of 50 years being affected by dry eye in the US. DED is a potentially disabling disease adversely impacting the vision-related quality of life. It leads to ocular discomfort, a degradation in visual performance (reading speed, contrast sensitivity), and a loss of productivity. Current therapeutic options are limited and costly. Topical cyclosporine-A (Restasis®) is the only approved treatment for DED in US (only). Despite the high incidence of DED, there is currently no consistently effective treatment for this condition and it still remains a therapeutic challenge. As such, there is a need for new therapeutic modalities to treat DED.

SUMMARY OF THE INVENTION

The present invention discloses a novel method for the treatment of dry eye disease in humans comprising administration of an anti-lymphangiogenic agent to the human subject. In particular, the present invention discloses a novel method for the treatment of dry eye disease in humans. In some embodiments, the method comprises locally administering an anti-lymphangiogenic agent to the ocular surface of the human. Preferably, the amount of the anti-lymphangiogenic agent employed is effective to inhibit the binding of VEGF-C and/or VEGF-D ligand to VEGFR-3 or the stimulatory effect of VEGF-C and/or VEGF-D on VEGFR-3.

The present invention is based on novel evidence for the selective growth of lymphatic vessels in DED cornea. Additionally, significant increase in both caliber and extent of lymphatics in DED corneas is accompanied by over expression of lymphangiogenic receptor VEGFR-3, further correlating DED with lymphangiogenesis.

An anti-lymphangiogenic agent of the invention is selected from the group consisting of: a nucleic acid molecule, an aptamer, an antisense molecule, an RNAi molecule, a protein, a peptide, a cyclic peptide, an antibody or antibody fragment, a polysaccharide, and a small molecule. The anti-lymphangiogenic agent described herein can be administered purely as a prophylactic treatment to prevent dry eye disease in subjects at risk for developing dry eye disease, or as a therapeutic treatment to subjects afflicted with dry eye disease, for the purpose of inhibiting lymphangiogenesis in the eye of a subject in need thereof.

In one preferred embodiment of the invention, the anti-lymphangiogenic agent is an inhibitor of VEGF-C or VEGF-D mediated signal transduction by VEGFR-2 or VEGFR-3. In a particularly preferred embodiment, the anti-lymphangiogenic agent is an inhibitor of VEGF-C or VEGF-D mediated signal transduction by VEGFR-3.

In one aspect of the invention, the inhibitor of VEGF-C or VEGF-D mediated signal transduction by VEGFR-2 or VEGFR-3 is a molecule such as but not restricted to an antibody, a small molecule or a peptide that prevents binding of VEGF-C or VEGF-D to the receptors VEGFR-2 or VEGFR-3.

In another aspect of the invention, the inhibitor of VEGF-C or VEGF-D mediated signal transduction is a VEGFR-2 or VEGFR-3 soluble receptor. Soluble receptors of VEGFR-2 or VEGFR-3 can be administered directly. Alternatively, increase in the secretion of VEGFR-2 or VEGFR-3 is accomplished by inserting the VEGFR-2 or VEGFR-3 soluble receptors genes into the genome of corneal cells. This could be epithelial cells, keratocytes, fibroblasts, endothelial cells, or bone marrow-derived cells. Methods to introduce genes into a genome of a cell are well-known in the art. Genes are introduced in the genome of corneal cells using viral or non-viral vectors. Viral vectors include for example adenoviruses, retroviruses or lentiviruses. Non-viral vectors include, for example, liposomes such as cationic lipids, nanoparticles, lipoplexes and polyplexes (complexes of polymers with DNA).

In one embodiment of the invention, the anti-lymphangiogenic agent is administered in combination with an anti-inflammatory agent such as, but not limited to, a composition inhibiting the activity of an inflammatory cytokine selected from the group comprising IL-1, IL-17, TNF-α and IL-6.

Exemplary functional blockers of IL-1 are described in WO/2009/025763. Exemplary functional blockers of TNF-α include, but are not limited to, recombinant and/or soluble TNF-α receptors, monoclonal antibodies, and small molecule antagonists and/or inverse agonists. One or more commercially-available TNF-α blocking agents are reformulated for topical administration in this embodiment. Exemplary commercial TNF-α blocking agents used for reformulation include, but are not limited to, etanerept/Ernbrel, infliximab/Remicade, and adalimumab/Humira.

In one embodiment of the invention, the anti-lymphangiogenic agent is administered in combination with an antiobiotic. Exemplary antibiotic compositions used for combination-therapy with antagonists of IL-mediated inflammation include but are not limited to, amikacin, gentamicin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, clozacillin, dicloxacillin, flucoxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline.

In one embodiment, the composition of the invention is locally applied to the ocular tissue, alternatively the composition of the invention is applied to the eyelids, the ocular surface, the meibomian glands or the lacrimal glands.

The composition can be in the form of a solid, a paste, an ointment, a gel, a liquid, an aerosol, a mist, a polymer, a film, an emulsion, or a suspension.

Optionally, the composition further contains a compound selected from the group consisting of a physiological acceptable salt, poloxamer analogs with carbopol, carbopol/hydroxypropyl methyl cellulose (RP MC), carbopol-methyl cellulose, carboxymethylcellulose (CMC), hyaluronic acid, cyclodextrin, and petroleum.

In one embodiment, described herein is a method of inhibiting dry eye disease in a subject at risk for developing dry eye disease comprising identifying a subject as being at risk for developing dry eye disease and administering an anti-lymphangiogenic agent to the subject. The amount of the anti-lymphangiogenic agent administered to the subject is preferably in an amount effective to inhibit the development of dry eye disease in the subject.

In another embodiment, described herein is a method of selecting a therapeutic regimen for a subject in need thereof comprising screening a subject for one or more symptoms of dry eye disease and prescribing for the subject administration of a composition comprising an anti-lymphangiogenic agent described herein. In another embodiment, described herein is a method of treating a subject affected with dry eye disease comprising identifying a subject as having one or more symptoms of dry eye disease and administering a composition comprising an anti-lymphangiogenic agent to the subject.

In some embodiments, the methods described herein further comprise prescribing (or administering) a standard of care regimen for the treatment of dry eye disease. In the context of methods described herein, "standard of care" refers to a treatment that is generally accepted by clinicians for a certain type of patient diagnosed with a type of illness. For dry eye disease, for example, an aspect of the invention is to improve standard of care therapy with co-therapy with anti-lymphangiogenic agents described herein that inhibit lymphangiogenesis.

Another aspect described herein is a method of treating a human subject with dry eye disease that has been hypo-responsive to a standard of care treatment for dry eye disease comprising administering an anti-lymphangiogenic agent described herein. For example, such a method comprises administering to such a subject a therapeutically effective amount of a composition that comprises an anti-lymphangiogenic agent described herein. Such a method optionally includes a step, prior to the administering step, of selecting for treatment a subject with dry eye disease that is hypo-responsive to a standard of care regimen for the treatment of the dry eye disease. The term "hypo-responsive" embraces subjects that failed to respond adequately to a standard of care treatment and subjects that initially responded, but for whom the standard of care treatment has become less effective over time.

In one embodiment, methods described herein optionally comprise administering a VEGFR-2 inhibitor product to the subject. The "VEGFR-2 inhibitor product" can be any molecule that acts with specificity to reduce VEGF-C/VEGFR-2, VEGF-D/VEGFR-2 or VEGF/VEGFR-2 interactions, e.g., by blocking VEGF-C or VEGF-D binding to VEGFR-2, by blocking VEGF binding to VEGFR-2 or by reducing expression of VEGFR-2. In one embodiment, the VEGFR-2 inhibitor inhibits VEGF-C and VEGF-D binding to VEGFR-2. In another embodiment, the VEGFR-2 inhibitor inhibits binding of VEGF to VEGFR-2. The VEGFR-2 inhibitor can be a polypeptide comprising a soluble VEGFR-2 extracellular domain fragment (amino acids 20-764 of SEQ ID NO: 51) that binds VEGF or VEGF-C or VEGF-D; VEGFR-2 anti-sense polynucleotides or short-interfering RNA (siRNA); anti-VEGFR-2 antibodies; a VEGFR-2 inhibitor polypeptide comprising an antigen-binding fragment of an anti-VEGFR-2 antibody that inhibits binding between VEGFR-2 and VEGF or VEGF-C or VEGF-D; an aptamer that inhibits binding between VEGFR-2 and VEGF; an aptamer that inhibits binding between VEGFR-2 and VEGF-C; an aptamer that inhibits binding between VEGFR-2 and VEGF-D; or a fusion protein comprising the soluble VEGFR-2 polypeptide fragment fused to an immunoglobulin constant region fragment (Fc). In some embodiments, a VEGFR-2 polypeptide fragment is fused to alkaline phosphatase (AP).

In another embodiment, the methods described herein optionally comprise administering one or more anti-inflammatory agents to the subject. In another embodiments, the methods described herein optionally further comprise administering a tyrosine kinase inhibitor that inhibits VEGFR-2 and/or VEGFR-3 activity.

Dry eye disease may be attributable to a number of factors, and treatment of subjects who have developed dry eye disease due to a variety of specific factors is contemplated. In some variations, the DED to be treated is DED caused by any condition other than an alloimmune response. Alloimmune responses may result, for example, in some corneal transplant patients. More specifically, in some variations, the DED to be treated is an autoimmune DED or a DED associated with Sjogren's syndrome. In some variations, the DED is due to excessively fast tear evaporation (evaporative dry eyes) or inadequate tear production. In some variations, the dry eye disease is attributable to one or more causes selected from: aging, contact lens usage and medication usage. In some variations, the dry eye disease is a complication of LASIK refractive surgery. In other variations, the DED arises in a subject who has not had eye surgery of any kind, e.g., treatment of subjects in whom the DED is caused by LASIK surgery, corneal transplant surgery, or other ocular surgeries.

In some variations, the invention is directed to prophylaxis, to prevent DED disease or its symptoms from developing. Prophylaxis may be appropriate, for example, in the context of subjects who have suffered an eye trauma such as infection, injury, chemical exposure, inflammation, or other situations that have been shown to cause or predispose individuals to DED. In some variations, the prophylaxis is continued until the trauma or the observable effects of the trauma have resolved, or for a limited duration, e.g., 1, 2, 3, or 4 weeks thereafter.

In a preferred embodiment, the mammalian subject is a human subject. Practice of methods of the invention in other mammalian subjects, especially mammals that are conventionally used as models for demonstrating therapeutic efficacy in humans (e.g., primate, porcine, canine, or rabbit animals), is also contemplated.

In addition to the foregoing, the following paragraphs are also considered aspects of the invention:

1. A method of treating dry eye disease (DED) in a human comprising:

administering a composition comprising at least one anti-lymphangiogenic agent and a pharmaceutically acceptable carrier the human, in an amount effective to treat dry eye disease.

2. The method of claim 1, wherein the anti-lymphangiogenic agent is administered to the eye of the human.

3. The method of paragraph 1, wherein the anti-lymphangiogenic agent is an inhibitor of VEGF-C or VEGF-D mediated signal transduction by VEGFR-2 or VEGFR-3.

4. An anti-lymphangiogenic agent for use in the treatment of dry eye disease.

5. Use of at least one anti-lymphangiogenic agent in a composition comprising a pharmaceutically acceptable carrier for administering the eye of a human, for the treatment of dry eye disease.

6. The method or use of paragraph 1 or 5, wherein the DED is an autoimmune DED or a DED associated with Sjogren's syndrome.

7. The method or use of any one of paragraphs 1-3 and 5, wherein the DED is DED due to excessively fast tear evaporation (evaporative dry eyes) or inadequate tear production.

8. The method or use of any one of paragraphs 1-3 and 5, wherein the dry eye disease is attributable to one or more causes selected from: aging, contact lens usage and medication usage.

9. The method or use of any one of paragraphs 1-3 and 5, wherein the dry eye disease is a complication of LASIK refractive surgery.

10. The method or use of any one of paragraphs 1-3 and 5, wherein the at least one anti-lymphangiogenic agent is purified or isolated.

11. The method or use of any one of paragraphs 1-3 and 5, wherein said at least one anti-lymphangiogenic agent comprises a member selected from the group consisting of: a nucleic acid molecule, an aptamer, an antisense molecule, an RNAi molecule, a protein, a peptide, a cyclic peptide, an antibody or antibody fragment, a polysaccharide, or a small molecule.

12. The method or use of any one of paragraphs 1-3 and 5-11, wherein said at least one anti-lymphangiogenic agent comprises a member selected from the group consisting of a VEGFR-3 inhibitor, a VEGF-D inhibitor and a VEGF-C inhibitor.

13. The method or use of any one of paragraphs 1-3 and 5-11, wherein the at least one anti-lymphangiogenic agent comprises a member selected from the group consisting of a VEGF-C antibody, a VEGF-D antibody, a VEGF-R3 antibody, and a polypeptide comprising a soluble VEGFR-3 fragment that binds VEGF-C or VEGF-D.

14. The method or use of paragraph 13, wherein the at least one anti-lymphangiogenic agent comprises a VEGF-C antibody.

15. The method or use of paragraph 14, wherein the antibody comprises a heavy chain variable region set forth in amino acids 1-118 of SEQ ID NO: 48.

16. The method or use of paragraph 14, wherein antibody comprises a heavy chain comprising the amino acid sequence of SEQ ID NO: 48.

17. The method or use of paragraph 14, wherein the VEGF-C antibody is selected from the group consisting of antibodies 69D09, 103, MM0006-2E65 and 193208.

18. The method or use of any one of paragraphs 1-3 and 5-11, wherein the at least one anti-lymphangiogenic agent comprises an antibody that competitively inhibits the binding of antibody 69D09 to VEGF-C.

19. The method or use of any one of paragraphs 1-3 and 5-11, wherein the at least one anti-lymphangiogenic agent comprises a VEGF-D antibody.

20. The method or use of paragraph 19, wherein the VEGF-D antibody is selected from the group consisting of antibodies 2F8, 4A5(VD1), 4E10, 5F12, 4H4, 3C10 28AT743.288.48, MM0001-7E79, RM0007-8C35, 78902, 78939 and 90409.

21. The method or use of any one of paragraphs 1-3 and 5-11, wherein the at least one anti-lymphangiogenic agent comprises a soluble VEGFR-3 fragment that binds VEGF-C or VEGF-D.

22. The method or use of any one of paragraphs 1-3 and 5-11, wherein the at least one anti-lymphangiogenic agent comprises a human or humanized antibody.

23. The method or use of any one of paragraphs 1-3 and 5-11, wherein the at least one anti-lymphangiogenic agent comprises a VEGFR-2 inhibitor.

24. The method or use of any one of paragraphs 1-3 and 5-11 wherein the at least one anti-lympnahgiogenic agent comprises a tyorine kinase inhibitor that inhibits the activity of VEGFR-3.

25. The method or use of any one of paragraphs 1-3 and 5-24, further comprising administering an anti-inflammatory agent to the subject.

26. The method or use of paragraph 25, further comprising administering cyclosporine to the subject.

27. The method or use of any one of paragraphs 1-3 and 5-26, wherein said composition further comprises a molecule that inhibits an activity of an inflammatory cytokine selected from the group consisting of IL-1, IL-7, IL23, IL-6 and TNF-$\alpha$.

28. The method or use of any one of paragraphs 1-3 and 5-27, wherein the method further comprises administering an antibiotic to the human.

29. The use of any one of paragraphs 5-27 further including the use of an antibiotic for the treatment of the dry eye disease.

30. The method or use of paragraph 28 or 29, wherein the antibiotic is selected from the group consisting of amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline.

31. The method or use of any one of paragraphs 1-3 and 5-27, wherein the eye comprises a tissue or gland in or around the eye selected from the group consisting of ocular tissue, eyelids of the subject, ocular surface, meibomian gland and or lacrimal gland of the human.

32. The method of any one of paragraphs 1-3 and 5-27, wherein said composition is administered topically to the eye.

33. The use according to any one of paragraphs 5-27, wherein the composition is formulated for topical administration.

34. The method or use of any one of paragraphs 1-3 and 5-33, wherein said composition is in the form of a solid, a paste, an ointment, a gel, a liquid, an aerosol, a mist, a polymer, a film, an emulsion, or a suspension.

35. The method or use of any one of paragraphs 1-3 and 5-34, wherein the composition further comprises a compound selected from the group consisting of physiological acceptable salt, poloxamer analogs with carbopol, carbopol/ hydroxypropyl methyl cellulose (RP MC), carbopol-methyl cellulose, carboxymethylcellulose (CMC), hyaluronic acid, cyclodextrin, and petroleum.

Additional aspects, features and variations of the invention will be apparent from the entirety of this application, including the detailed description, and all such features are intended as aspects of the invention. It should be understood, however, that the detailed description and the specific examples are given by way of illustration, and that the many various changes and modifications that will be apparent to those familiar with the field of the invention are also part of the invention.

Aspects of the invention described with the term "comprising" should be understood to include the elements explicitly listed, and optionally, additional elements. Aspects of the invention described with "a" or "an" should be understood to include "one or more" unless the context clearly requires a narrower meaning.

Moreover, features of the invention described herein can be re-combined into additional embodiments that also are intended as aspects of the invention, irrespective of whether the combination of features is specifically mentioned above as an aspect or embodiment of the invention. Also, only those limitations that are described herein as critical to the invention should be viewed as such; variations of the invention lacking features that have not been described herein as critical are intended as aspects of the invention.

With respect to aspects of the invention that have been described as a set or genus, every individual member of the set or genus is intended, individually, as an aspect of the invention, even if, for brevity, every individual member has not been specifically mentioned herein. When aspects of the invention that are described herein as being selected from a genus, it should be understood that the selection can include mixtures of two or more members of the genus. Similarly, with respect to aspects of the invention that have been described as a range, such as a range of values, every sub-range within the range is considered an aspect of the invention.

In addition to the foregoing, the invention includes, as an additional aspect, all embodiments of the invention narrower in scope in any way than the variations specifically described herein. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

Dry Eye Disease

Figure 1:
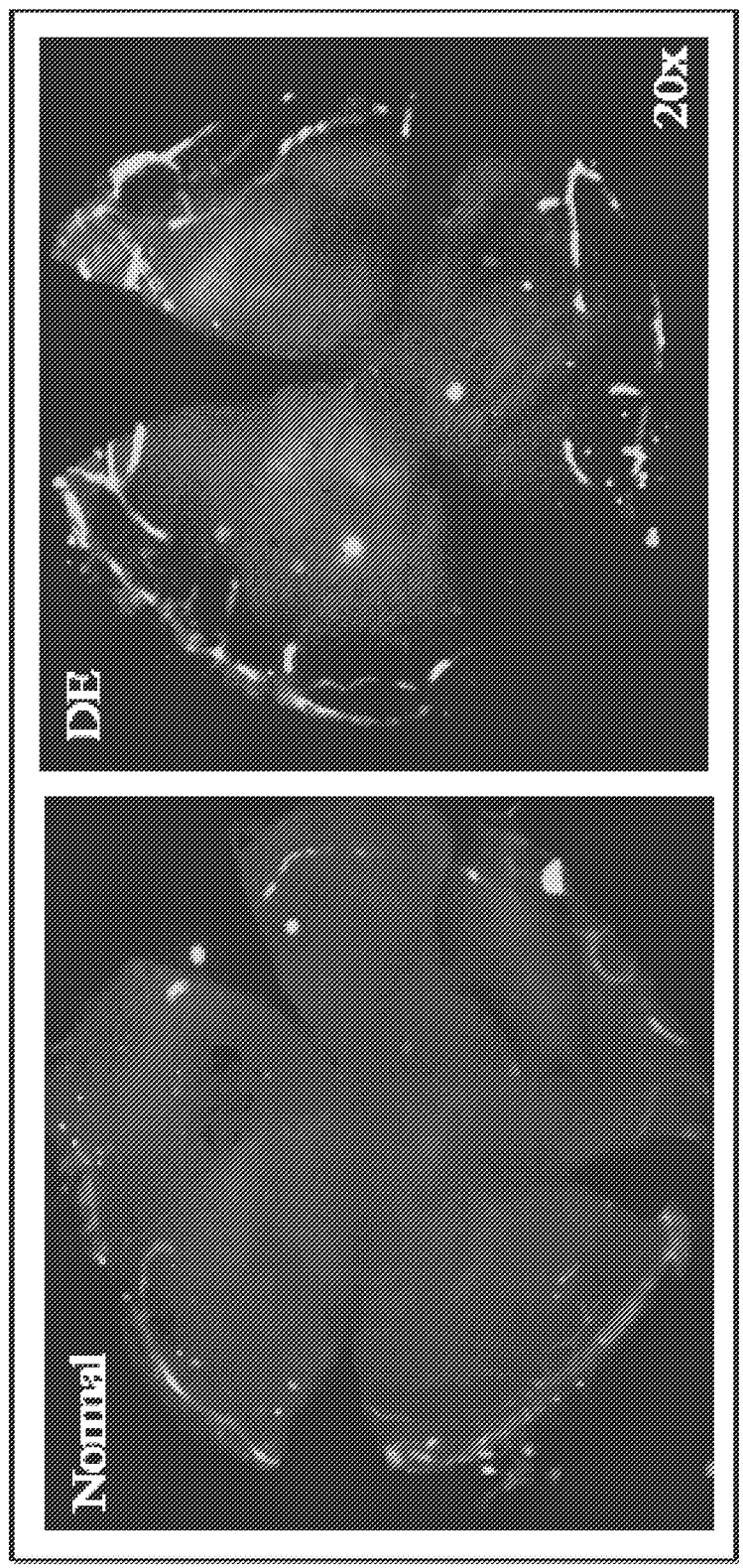
FIG. 1: Representative whole mount corneal immunofluorescence micrographs showing lymphatics (CD31$^{lo}$/LYVE-1$^{hi}$) in normal and dry eye (DE) at day 14 (20× magnification).

Keratoconjunctivitis sicca (KCS), also called keratitis sicca, sicca syndrome, xerophthalmia, dry eye syndrome (DES), dry eye disease (DED), or simply dry eyes, is an eye disease caused by decreased tear production or increased tear film evaporation commonly found in humans and some animals. Typical symptoms of keratoconjunctivitis are dryness, burning and a sandygritty eye irritation that gets worse as the day goes on.

In the context of the present invention the term "dry eye condition" denotes any condition or syndrome which results in the manifestation of dry eye symptoms. It includes an already existing condition as well as pseudo dry eye conditions, i.e. conditions high predisposition of developing dry eye syndromes. Dry eye disease may be as a result of another underlying condition causing dry eye, for example, Sjogren's syndrome, menopause or rheumatoid arthritis. Dry eye may also be a complication of inflammation, e.g. Blepharitis or of a foreign body in the eye. Dry eye may also be the result of infection, or a side effect of medications, or exposure to toxins, chemicals, or other substances may cause a symptom or condition of dry eye. Dry eye conditions may be manifested by one or more ophthalmologic clinical symptoms as known in the art. Examples of dry eye symptoms include, but are not limited to, foreign body sensation, burning, itching, irritation, redness, eye pain, blurred vision and/or degraded vision.

Keratoconjunctivitis sicca is characterized by inadequate tear film protection of the cornea because of either inadequate tear production or abnormal tear film constitution, which results in excessively fast evaporation or premature destruction of the tear film. The tear film is constituted by 3 layers: (1) a lipid layer, produced by the Meibomian glands; (2) an aqueous layer, produced by the main and accessory lacrimal glands; and (3) a hydrophilic mucin layer, produced by the conjunctival goblet cells. Any abnormality of 1 of the 3 layers produces an unstable tear film and symptoms of keratitis sicca.

Sjogren's syndrome and autoimmune diseases associated with Sjogren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine can cause or worsen this condition. Infiltration of the lacrimal glands by sarcoidosis or tumors, or postradiation fibrosis of the lacrimal glands can also cause this condition.

Keratoconjunctivitis sicca can also be caused by abnormal tear composition resulting in rapid evaporation or premature destruction of the tears. When caused by rapid evaporation, it is termed evaporative dry eyes. In this, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

Aging is one of the most common causes of dry eyes. About half of all people who wear contact lenses complain of dry eyes. There are two potential connections between contact lens usage and dry eye. Traditionally, it has been believed that soft contact lenses, which float on the tear film that covers the cornea, absorb the tears in the eyes. However, it is also now known that contact lens usage damages corneal nerve sensitivity, which may lead to decreased lacrimal gland tear production and dry eye. The effect of contact lenses on corneal nerve sensitivity is well established for hard contact lenses as well as soft and rigid gas permeable contact lenses. The connection between this loss in nerve sensitivity and tear production is the subject of current research. Dry eyes also occur or get worse after LASIK and other refractive surgeries. The corneal nerves stimulate tear secretion. Dry eyes caused by these procedures usually resolves after several months. Persons who are thinking about refractive surgery should consider this.

A variety of approaches can be taken to treat dry eyes. These can be summarized as: avoidance of exacerbating factors, tear stimulation and supplementation, increasing tear retention, eyelid cleansing and treatment of eye inflammation. Application of artificial tears every few hours can provide temporary relief. Inflammation occurring in response to tears film hypertonicity can be suppressed by mild topical steroids or with topical immunosuppressants such as cyclosporine. Consumption of dark-fleshed fish containing dietary omega-3 fatty acids is associated with a decreased incidence of dry eyes syndrome in women. Early experimental work on omega-3 has shown promising results when used in a topical application (Rashid S et al (2008). Arch Ophthalmol 126 (2): 219-225).

DED is increasingly recognized as an immune-mediated disorder. Desiccating stress in DED initiates an immune-based inflammation response that is sustained by the ongoing interplay between the ocular surface and various pathogenic immune cells, primarily the CD4+ cells in the conjunctivia and the CD11b+ monocytic cells in the corneal. Dessiccating stress induces secretion of inflammatory cytokines, especially IL-1, TNF-α and IL-6 by ocular tissues, which facilitates the activation and migration of resident antigen presenting cells (APCs) toward the regional draining lymph nodes (LNs). In the LNs, these APCs stimulate naive T-cells, leading to the expansion of IL-17 secreting Th17 cells and interferon (IFN)-γ-secreting Th1 cells. Once these effectors are generated in the LNs, they migrate to the ocular surface and secrete effector cytokines.

VEGF Family of Growth Factors

VEGF (Vascular Endothelial Growth Factor) is a sub-family of growth factors, specifically the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature). Members of the platelet-derived growth factor family include the Placenta growth factor (PlGF), VEGF-A (also known as VEGF), VEGF-B, VEGF-C, VEGF-D and VEGF-E.

VEGF-A, VEGF-C and VEGF-D exert their effects by variously binding to and activating two structurally related membrane receptor tyrosine kinases, VEGF receptor-1 (VEGFR-1 or Flt-I), VEGF receptor-2 (flk-1 or KDR), and VEGFR-3 (Flt-4). Members of the VEGF family may also interact with the structurally distinct receptor neuropilin-1. Binding of a VEGF to these receptors initiates a signaling cascade, resulting in effects on gene expression and cell survival, proliferation, and migration.

VEGF-A binds to VEGFR-1 (Flt-1) and to VEGFR-2 (KDR/Flk-1). VEGFR-2 appears to mediate almost all of the known cellular responses to VEGF-A. The function of VEGFR-1 is less well-defined, although it is thought to modulate VEGFR-2 signaling. VEGF-A is believed to play a central role in the development of new blood vessels (angiogenesis) and the survival of immature blood vessels (vascular maintenance). VEGF-C and VEGF-D are ligands for VEGFR-2 and VEGFR-3 and are involved in the mediation of lymphangiogenesis.

Lymphangiogenesis

Lymphangiogenesis refers to formation of lymphatic vessels, particularly from pre-existing lymphatic vessels, but as used herein, the term applies to formation of lymph vessels under any condition. It also applies to the enlargement of lymphatic vessels, commonly known as lymphatic hyperplasia. Lymphangiogenesis plays an important physiological role in homeostasis, metabolism and immunity. Lymphatic vessel formation has also been implicated in a number of pathological conditions including neoplasm metastasis, oedema, rheumatoid arthritis, psoriasis and impaired wound healing.

The normal human cornea is avascular, thus suppressing the afferent lymphatic and efferent vascular arms or the immune cycle Inflammation however negates this immune and angiogenic privileged state of the cornea and giving the corneal and ocular surface the potential to mount an immune response. Our results show that corneal lymphatics play an important role in mediating the corneal inflammation in dry eyes. Inhibition of corneal lymphangiogenesis decreases ocular surface inflammation in a well characterized mouse model of DED.

Lymphangiogenesis is regulated to a large extent by VEGF-C and VEGF-D. Lymphangiogenesis appears to be regulated by signaling mediated by VEGFR-3, particularly upon specifically binding its ligands, VEGF-C and VEGF-D.

During embryogenesis, lymphatic endothelial cell sprouting, proliferation and survival is promoted by VEGF-C. Lymphatic vessels fail to develop in mice in which VEGF-C is absent (Vegfc knockout mice), and such mice develop severe edema. Indeed, absence of VEGF-C is embryonic lethal. Lymphatic vessel hypoplasia and lymphedema is exhibited in the skin of mice hemizygous for Vegfc (i.e. mice possessing one functional allele).

Embryonic lymphangiogenesis is also partly regulated by VEGF-D, similar to VEGF-C. However, lymphangiogenesis during embryonic development is not dependent upon VEGF-D, as demonstrated by Vegfd knockout mice. The lymphatic system in Vegfd knockout mice is relatively normal and Vegfd knockout mice are viable and fertile. The absolute abundance of lymphatic vessels in the lung is, however, reduced by approximately 30% compared to wild-type mice.

Lymphatic vessels express VEGFR-3, the receptor for VEGF-C and VEGF-D, and both VEGF-C and VEGF-D signal predominantly through VEGFR-3. It is also becoming apparent that lymphatic vessels variously express VEGFR-2. VEGF-C and VEGF-D are synthesized as prepro-polypeptides and are proteolytically processed by proprotein convertases. In humans, mature proteolytically processed forms of VEGF-C and VEGF-D bind to VEGFR-2 and VEGFR-3. In mice, mature VEGF-D binding is restricted to VEGFR-3.

VEGF-C and VEGF-D exist as homodimers, and it has been suggested that they may exist as VEGF-C-VEGF-D heterodimers. In addition to lymphatic vessels, VEGFR-3 is also expressed on blood vessel endothelial cells during development, thereby accounting for the severe vasculogenic and angiogenic defects observed during early embryogenesis in models comprising inactive VEGFR-3 signaling. The lymphatic system possesses almost exclusive expression of VEGFR-3 in healthy tissues in adulthood, because VEGFR-3 expression in blood vessels declines following birth and during adolescence. Thus, only lymphangiogenesis is inhibited in adults by inhibition of the VEGF-C-VEGF-D-VEGFR-3 signaling axis.

Lymphatic vessels express neuropilin-2 (NRP-2), which can bind VEGF-C or VEGF-D. In lymphangiogenesis, NRP-2 is thought to act as a co-receptor to increase the binding affinity of VEGF-C or VEGF-D to VEGFR-3. NRP-2 is required for lymphangiogenesis. Proliferation of lymphatic vessel endothelial cells was reduced and lymphatic vessels and capillaries failed to develop in Nrp2 knockout mice in which NRP-2 is absent. Similarly, NRP-1 is capable of binding VEGF-C and VEGF-D.

Defective lymphatic capillaries are the underlying cause of Milroy disease and other rare hereditary forms of lymphedema in humans. Tyrosine kinase-inactivating point mutations of the VEGFR-3 gene have been identified as a major cause of Milroy disease, and VEGF-C and VEGF-D therapy has shown promising efficacy in preclinical animal models. However, previous work has only demonstrated lymphatic capillary reconstitution, whereas effects on the collecting lymphatic vessels that are more commonly damaged in lymphedema have not been addressed.

Lymphatic vessel growth in adult tissues can be induced by Angiopoietin-1 (ANG-1) through its binding to the tunica interna endothelial cell kinase receptor 2 (TIE-2 or TEK). Lymphatic vessel sprouting that was induced by ANG-1 was inhibited by an inhibitor of VEGFR-3. Furthermore, VEGFR-3 was up-regulated by ANG-1 binding to TIE-2. TIE-2 expressed on lymphatic vascular endothelial cells may also be agonized by ANG-2 and ANG-3.

VEGF-C and VEGF-D may act as ligands for integrins. Specifically, VEGF-C and VEGF-D have been shown to act as ligands for integrin $\alpha9\beta1$. Cell adherence and cell migration were promoted by each of VEGF-C and VEGF-D in cells expressing integrin $\alpha9\beta1$. The effect could be blocked by an anti-integrin $\alpha9\beta1$ antibody or siRNA directed to integrin $\alpha9\beta1$.

Thus, in lymphangiogenesis, VEGFR-3 appears to be central. VEGFR-3 specifically binds and is activated by ligands VEGF-C and VEGF-D. VEGF-C and VEGF-D are synthesized as prepro-polypeptides and are activated by proteolytic processing by proprotein convertases. VEGF-C and VEGF-D also bind specifically to NRP-2, which is thought to be a co-receptor for VEGFR-3. Both lymphangiogenesis and VEGFR-3 are up-regulated when ANG-1 specifically binds to TIE-2. It is thought that binding of VEGF-C or VEGF-D to integrins, particularly integrin $\alpha9\beta1$, also performs a role in lymphangiogenesis.

Lymphangiogenesis is mediated primarily by the interaction of growth factors VEGF-C and VEGF-D on VEGFR-2 and VEGFR-3, and in particular on VEGFR-3. VEGF-A also contributes, albeit indirectly, to lymphangiogenesis by recruiting VEGF-C and VEGF-D secreting macrophages. Inhibition of VEGF-C and VEGF-D signaling pathways would thus constitute a new approach to the treatment of DED. The invention is however not restricted to the inhibition of VEGF-C and VEGF-D signaling pathways and according to the present invention, other anti-lymphangiogenic agents can be used to reduce the signs and symptoms of DED.

Anti-Lymphangiogenic Agents

Persons skilled in the art will appreciate from the foregoing that inhibition of lymphangiogenesis can occur at a variety of biological points comprising any one or more of the interactions described. For example, inhibition may occur by targeting VEGF-D, VEGF-C or VEGFR-3.

An "anti-lymphangiogenic agent" as described herein refers to any substance that partially or fully blocks, neutralizes, reduces, inhibits or antagonizes a biological activity of a molecular component of signaling mediated by VEGFR-3 or lymphangiogenesis. Alternatively, an anti-lymphangiogenic agent is any substance that partially or fully blocks, neutralizes, reduces, inhibits or antagonizes a VEGF-C or VEGF-D biological activity. Thus, "inhibition" is the corresponding state elicited by an inhibitor. A molecular component of signaling mediated by VEGFR-3 or lymphangiogenesis includes VEGFR-3, VEGFR-2, VEGF-C, VEGF-D, proprotein convertases, neuropilin-1 (NRP-1), neuropilin-2 (NRP-2), angiopoietin-1 (ANG-1), tunica interna endothelial cell kinase receptor (TIE-2) or integrin $\alpha9\beta1$.

It is envisaged that practice of the invention extends to any inhibitor known now or in the future.

Suitable classes of inhibitor molecules that target VEGF-C or VEGF-D or signaling mediated by VEGFR-3, or lymphangiogenesis include antibodies, polypeptides, peptides, peptide mimetics, nucleic acid molecules, and small molecules. Such classes of inhibitor molecules are suitable also for inhibiting binding of ligands, for example VEGF-C or VEGF-D, to integrins, particularly integrin $\alpha9\beta1$.

Suitable VEGF-C, VEGF-D, VEGFR-3-mediated signaling or lymphangiogenesis antibody inhibitors include antagonist and neutralizing antibodies or antibody fragments.

Polypeptide, peptide, or peptide mimetic VEGF-C or VEGF-D inhibitors, VEGFR-3-mediated signaling inhibitors or lymphangiogenesis inhibitors include fragments or amino acid sequence variants of native polypeptide or peptide components of VEGF-C, VEGF-D, VEGFR-3-mediated signaling or lymphangiogenesis.

Nucleic acid molecule inhibitors of VEGF-C or VEGF-D activity, VEGFR-3-mediated signaling or lymphangiogenesis include antisense molecules, nucleic acids in triple-helix formation, small interfering RNA (siRNA), and ribozymes.

Small molecule inhibitors of VEGF-C or VEGF-D, VEGFR-3-mediated signaling or lymphangiogenesis include organic and inorganic molecules.

Inhibitors of VEGF-C or VEGF-D activity, VEGFR-3-mediated signaling or lymphangiogenesis according to the present invention may exert their effects by interacting with any one or more of VEGFR-3, VEGFR-2, VEGF-C, VEGF-D, proprotein convertases, NRP-1, NRP-2, ANG-1, TIE-2 or integrins, particularly integrin $\alpha9\beta1$, in their DNA, RNA or polypeptide forms.

Inhibition of VEGF-C or VEGF-D activity, VEGFR-3-mediated signaling or lymphangiogenesis according to the present invention may occur via inhibition of ligand availability for receptor binding, inhibition of receptor availability for ligand binding, inhibition of receptor tyrosine kinase activity, or inhibition of co-receptor interaction.

As used herein, "availability" refers to the potential or actual amount of a molecule that performs some function in VEGF-C or VEGF-D activity, VEGFR-3-mediated signaling or lymphangiogenesis and is present in a biological system. Availability may be relative or absolute. For example, if all copies of a gene encoding a polypeptide involved in lymphangiogenesis were rendered non-functional by genetic mutation and no functioning polypeptide was synthesized, then there would be no availability of the polypeptide in an absolute sense. Alternatively, if the same gene was present with one functioning copy and 50% of the polypeptide was synthesized, there would be reduced or inhibited availability in a relative sense. Similarly, other mechanisms may be envisaged where availability is affected. Receptors may be transcribed or translated to a lesser degree when compared with a control, or the receptor may be targeted by an antibody that binds specifically to the ligand binding site, thereby reducing or inhibiting receptor availability for ligand binding. Analogously, if ligand synthesis is targeted by an antisense inhibitor, or if an antibody inhibitor or soluble receptor inhibitor specifically binds to the ligand, then there will be reduction or inhibition of ligand availability for receptor binding.

The term "specific binding" or "specifically binds" or "specific for" refers to binding where a molecule binds to a particular polypeptide or epitope on a particular polypeptide without substantially binding to any other polypeptide or polypeptide epitope. Such binding is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, specific binding is used in relation to the interaction between the molecular components of VEGF-C or VEGF-D activity, VEGFR-3-mediated signaling or lymphangiogenesis. Specific binding is also used in relation to the interaction between the molecular components of VEGF-C or VEGF-D activity, VEGFR-3-mediated signaling or lymphangiogenesis and agents that partially or fully block, neutralize, reduce or antagonize a biological activity of a molecule that facilitates VEGFR-3-mediated signaling or lymphangiogenesis. Specific binding also applies to the interaction between the molecular components of VEGF-C or VEGF-D activity and agents that partially or fully block, neutralize, reduce or antagonize VEGF-C or VEGF-D biological activity.

In particular, specific binding refers to a molecule having a $K_d$ at least 2-fold less for the particular polypeptide or epitope on a particular polypeptide than it does for a non-specific target. Preferably, specific binding refers to a molecule having a Kd at least 4-fold, 6-fold, 8-fold or 10-foldless for the particular polypeptide or epitope on a particular polypeptide than it does for a non-specific target. Alternatively, specific binding can be expressed as a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or less.

The person skilled in the art will appreciate that there exist many mechanisms for inhibiting VEGF-C or VEGF-D activity, VEGFR-3-mediated signaling or lymphangiogenesis. The principal aim is to reduce receptor signaling. Some examples will be described below, but such a list is not intended to be limiting.

Antibody Inhibitors

The term "antibody" is used in the broadest sense and specifically covers, for example, polyclonal antibodies, monoclonal antibodies (including antagonist and neutralizing antibodies), antibody compositions with polyepitopic specificity, single chain antibodies, and fragments of antibodies, provided that they exhibit the desired biological or immunological activity.

An "antibody inhibitor" will specifically bind to a particular polypeptide or epitope on a particular polypeptide without substantially binding to any other polypeptide or polypeptide epitope. Such binding will partially or fully block, neutralize, reduce or antagonize VEGF-C or VEGF-D activity or a biological activity of a molecule that facilitates VEGFR-3-mediated signaling or lymphangiogenesis. Such target molecules include VEGFR-3, VEGFR-2, VEGF-C and VEGF-D, for example.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. Generally, the antibody will be purified (1) to greater than 95% by weight of antibody as determined by the Lowry method, and most preferably more than 99% by weight, (2) to a degree sufficient to obtain at least 15 residues of N terminal or internal amino acid sequence by use of a spinning cup sequenator, or (3) to homogeneity by SDS PAGE under reducing or non-reducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

Where antibody fragments are used, the smallest inhibitory fragment that specifically binds to the binding domain of the target protein is preferred.

Polyclonal Antibodies

Polyclonal antibodies are preferably raised in animals by multiple subcutaneous (s.c.) or intraperitoneal (i.p.) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

In one protocol for generating polyclonal antibodies, animals are immunized against the antigen, immunogenic conjugate, or derivative, by combining the antigen, conjugate or derivative with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

Monoclonal Antibodies

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method.

Monoclonal antibodies may be made using the hybridoma method in which a mouse or other appropriate host animal, such as a hamster, is immunized to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell.

The hybridoma cells thus prepared are seeded and grown in a suitable culture medium, which preferably contains one or more substances that inhibit the growth or survival of the unfused, parental myeloma cells (also referred to as fusion partner).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

Once hybridoma cells that produce antibodies of the desired specificity, affinity, and/or activity are identified, the clones may be subcloned by limiting dilution procedures and grown by standard methods. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxyapatite chromatography, gel electrophoresis, or dialysis.

DNA encoding the monoclonal antibodies is readily isolated and sequenced using conventional procedures. The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells.

Monoclonal antibodies or antibody fragments can be isolated from antibody phage libraries. High affinity (nM range) human antibodies can be generated by chain shuffling, as well as combinatorial infection and in vivo recombination as a strategy for constructing very large phage libraries. Thus, these techniques are viable alternatives to traditional monoclonal antibody hybridoma techniques for isolation of monoclonal antibodies.

The DNA that encodes the antibody may be modified to produce chimeric or fusion antibody polypeptides. The monoclonal antibodies used herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Human and Humanized Antibodies

The anti-VEGF-C, anti-VEGF-D, anti-VEGFR-3-mediated signaling or anti-lymphangiogenesis antibodies used in the invention may comprise humanized antibodies or human antibodies. Generally, a "humanized antibody" is an antibody of non-human origin that has been modified using recombinant DNA techniques to circumvent the problem of a human's immune system reacting to an antibody as a foreign antigen. The standard procedure of producing monoclonal antibodies produces mouse antibodies. Although murine antibodies are very similar to human ones, there are differences. Consequently, the human immune system recognizes mouse antibodies as foreign, rapidly removing them from circulation and causing systemic inflammatory effects. "Humanized" forms of non-human (e.g., rodent) antibodies are chimeric antibodies that contain a reduced percentage of sequence derived from the non-human antibody. Various forms of humanized anti-VEGF-C, anti-VEGF-D, anti-VEGFR-3-mediated signaling or anti-lymphangiogenesis antibodies are contemplated. Humanized antibodies may be intact antibodies, such as intact $IgG_1$ antibodies, antibody chains or fragments thereof (such as Fv, Fab, Fab', $F(ab')_2$, or other antigen-binding subsequences of antibodies). Humanized antibodies include human antibodies (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human antibody are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human antibody and all or substantially all of the FR regions are those of a human antibody consensus sequence. The humanized antibody optimally also will comprise at least a portion of an antibody constant region (Fc), typically that of a human antibody.

Various humanization strategies have been described in the prior art and it is envisaged that practice of the invention extends to the use of both known humanization strategies and any new strategies to be developed in the future. Examples of known humanization strategies include those described by Studnicka (U.S. Pat. No. 5,869,619) and Padlan (1991, Molec. Immunol., 28, 489-498), Winter (U.S. Pat. No. 5,225,539) and Jones et al (1986, Nature, 321, 522-525), Queen et al. (U.S. Pat. No. 5,693,761) and Foote (U.S. Pat. No. 6,881,557).

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. Alternatively, phage display technology can be used to produce human antibodies and antibody fragments in vitro, from immunoglobulin variable (V) domain gene repertoires from unimmunized donors. Phage display can be performed in a variety of formats. Several sources of V-gene segments can be used for phage display.

Antibody Fragments

"Antibody fragments" comprise a portion of an antibody, preferably the antigen binding or variable region of the intact antibody. Examples of antibody fragments include Fab, Fab', $F(ab')_2$, and Fv fragments; diabodies; linear antibodies; single chain antibody molecules; and multispecific antibodies formed from antibody fragments. Antibody fragments of particular interest are fragments that retain antigen-binding properties of the whole antibody, and are useful as inhibitors for practicing the invention.

Papain digestion of antibodies produces two identical antigen binding fragments, called "Fab" fragments, and a residual "Fc" fragment, a designation reflecting the ability to crystallize readily. Each Fab fragment is monovalent with respect to antigen binding, i.e., it has a single antigen binding site. Pepsin treatment of an antibody yields a single large $F(ab')_2$ fragment which roughly corresponds to two disulfide linked Fab fragments having divalent antigen binding activity and is still capable of cross linking antigen. Fab' fragments differ from Fab fragments by having additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" is the minimum antibody fragment which contains a complete antigen recognition binding site. This fragment consists of a dimer of one heavy and one light chain variable region domain in tight, non covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single chain Fv" abbreviated as "scFv" are antibody fragments that comprise the VH and VL antibody domains connected into a single polypeptide chain. Preferably, the scFv polypeptide further comprises a polypeptide linker between the VH and VL domains which enables the scFv to form the desired structure for antigen binding.

In certain circumstances there are advantages of using antibody fragments, rather than whole antibodies. The smaller size of the fragments allows for rapid clearance from the circulation.

Various techniques have been developed for the production of antibody fragments. Traditionally, these fragments were derived via proteolytic digestion of intact antibodies. However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries. Alternatively, Fab'-SH fragments can be directly recovered from E. coli and chemically coupled to form $F(ab')_2$ fragments. According to another approach, F(ab')₂ fragments can be isolated directly from recombinant host cell culture. Fab and F(ab')₂ fragment with increased in vivo half-life comprising a salvage receptor binding epitope residues also may be used.

Other techniques for the production of antibody fragments will be apparent to the skilled practitioner. The antibody of choice is a single chain Fv fragment (scFv). Fv and scFv are the only species with intact combining sites that are devoid of constant regions; thus, they are suitable for reduced nonspecific binding during in vivo use. The antibody fragment may also be a "linear antibody", which may be monospecific or bispecific. The inhibitor also may be a polypeptide or protein comprising an antibody or antibody fragment linked to another entity to form a fusion protein.

Bispecific Antibodies

Bispecific antibodies are antibodies that have binding specificities for at least two different epitopes. Bispecific antibodies can be prepared as full length antibodies or antibody fragments (e.g., F(ab')₂ bispecific antibodies).

Methods for making bispecific antibodies are known in the art. Traditional production of full length bispecific antibodies is based on the co-expression of two immunoglobulin heavy chain-light chain pairs, where the two chains have different specificities.

According to a different approach, antibody variable domains with the desired binding specificity (antibody-antigen combining sites) are fused to immunoglobulin constant domain sequences.

Bispecific antibodies include cross-linked or "heteroconjugate" antibodies. Heteroconjugate antibodies are composed of two covalently joined antibodies. It is contemplated that the antibodies may be prepared in vitro using known methods in synthetic protein chemistry, including those involving crosslinking agents. For example, one of the antibodies in the heteroconjugate can be coupled to avidin, the other to biotin. Heteroconjugate antibodies may be made using any convenient cross-linking methods. Suitable cross-linking agents and cross-linking techniques are well known in the art.

Techniques for generating bispecific antibodies from antibody fragments have also been described in the literature. For example, bispecific antibodies can be prepared using chemical linkage.

Recent progress has facilitated the direct recovery of Fab'-SH fragments from E. coli, which can be chemically coupled to form bispecific antibodies. Various techniques for making and isolating bispecific antibody fragments directly from recombinant cell culture have also been described.

The term "diabodies" refers to small antibody fragments prepared by constructing scFv fragments with short linkers (about 5 to 10 residues) between the VH and VL domains such that inter chain but not intra chain pairing of the V domains is achieved, resulting in a bivalent fragment, i.e., fragment having two antigen binding sites. Bispecific diabodies are heterodimers of two "crossover" scFv fragments in which the VH and VL domains of the two antibodies are present on different polypeptide chains.

According to an alternative "diabody" technology for making bispecific antibody fragments, the fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported.

Antibodies with more than two valencies are contemplated for use in the invention. For example, trispecific antibodies can be prepared.

Exemplary multivalent antibodies and binding constructs that are suitable inhibitors for practicing the invention include those described in International Patent Application No. PCT/US2005/007742 (published as WO 2005/087812 on 22 Sep. 2005) or US Patent Publication No. 2005/0282233, filed Mar. 7, 2005, published Dec. 22, 2005, both incorporated herein by reference in their entirety. These documents describe, for example, an antibody substance that specifically binds to first and second growth factors selected from the group consisting of human vascular endothelial growth factor-A (VEGF-A), human vascular endothelial growth factor-B (VEGF-B), human vascular endothelial growth factor-C (VEGF-C), human vascular endothelial growth factor-D (VEGF-D), human vascular endothelial growth factor-E (VEGF-E), human placental growth factor (PlGF), human platelet-derived growth factor-A (PDGF-A), human platelet-derived growth factor-B (PDGF-B), human platelet-derived growth factor-C (PDGF-C), and human platelet-derived growth factor-D (PDGF-D), wherein each of said growth factors binds and stimulates phosphorylation of at least one receptor tyrosine kinase, and wherein the antibody substance inhibits the first and second growth factors to which it binds from stimulating phosphorylation of said receptor tyrosine kinases. Of particular interest for the present invention are bi-specific antibody substances that bind two of VEGF-C, VEGF-D, and VEGF-A, for example. These documents also describe an antibody substance produced by a process comprising: (a) screening a library of antibody molecules to identify at least one antibody molecule that binds to a first growth factor selected from the group consisting of human vascular endothelial growth factor-A (VEGF-A), human vascular endothelial growth factor-B (VEGF-B), human vascular endothelial growth factor-C (VEGF-C), human vascular endothelial growth factor-D (VEGF-D), human vascular endothelial growth factor-E (VEGF-E), human placental growth factor (PlGF), human platelet-derived growth factor-A (PDGF-A), human platelet-derived growth factor-B (PDGF-B), human platelet-derived growth factor-C (PDGF-C), and human platelet-derived growth factor-D (PDGF-D), wherein each of said growth factors binds and stimulates phosphorylation of at least one receptor tyrosine kinase; (b) screening molecule(s) identified in (a) to identify at least one molecule that binds to a second growth factor selected from said group; (c) screening molecule(s) identified in step (b) to identify at least one molecule that inhibits the first and second growth factors to which it binds from stimulating phosphorylation of said receptor tyrosine kinases, wherein the antibody substance comprises a molecule identified in step (C).

A multivalent antibody may be internalized (and/or catabolized) faster than a bivalent antibody by a cell expressing an antigen to which the antibodies bind. Antibodies that may be used in the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. A preferred dimerization domain comprises an Fc region or a hinge region. In this scenario, the antibody will comprise an Fc region and three or more antigen binding sites amino-terminal to the Fc region. A preferred multivalent antibody comprises three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X_1)_n$-VD2-$(X_2)_n$-Fc, wherein VD1 is a first variable domain, VD2 is a second variable domain, Fc is one polypeptide chain of an Fc region, $X_1$ and $X_2$ represent an amino acid or polypeptide, and n is 0 or 1. For instance, the polypeptide chain(s) may comprise: $V_H$—$C_H$1-flexible linker-$V_H$—$C_H$1-Fc region chain; or $V_H$—$C_H$1-$V_H$-$C_H$1-Fc region chain. A multivalent antibody preferably further comprises at least two (and preferably four) light chain variable domain polypeptides. A multivalent antibody may, for instance, comprise from about two to about eight light chain variable domain polypeptides. The light chain variable domain polypeptides contemplated here comprise a light chain variable domain and, optionally, further comprise a CL domain.

Peptide and Peptide Mimetic Inhibitors

In another embodiment, the inhibitor of VEGF-D activity, VEGFR-3-mediated signaling or lymphangiogenesis is a peptide or peptide mimetic. The peptide or peptide mimetic may reduce receptor availability for native ligand binding.

As used herein, "peptide mimetic" and "peptidomimetic" are used interchangeably.

A peptide inhibitor is a peptide that binds specifically to a component of VEGF-C or VEGF-D activity, VEGFR-3-mediated signaling or lymphangiogenesis and inhibits or neutralizes the function of that component in the process of VEGF-C or VEGF-D activity, VEGFR-3-mediated signaling or lymphangiogenesis. Peptide inhibitors may be chemically synthesized using known peptide synthesis methodology or may be prepared and purified using recombinant technology. The preferred length of peptide inhibitors of VEGF-C or VEGF-D activity, VEGFR-3-mediated signaling or lymphangiogenesis is from about 6, 7, 8, 9 or 10 amino acid residues to about 100 amino acid residues. It is contemplated that longer peptides may prove useful. Peptide inhibitors may be identified without undue experimentation using well known techniques. In this regard, it is noted that techniques for screening peptide libraries for peptides that are capable of specifically binding to a polypeptide target are well known in the art.

For any of the foregoing peptides, one preferred variation involves peptides that have been modified to comprise an intramolecular bond between two non-adjacent amino acid residues of the primary sequence, thereby forming a cyclic peptide. For example, in one variation, the peptide comprises a pair of cysteine residues, such as amino- and carboxy-terminal cysteines, and the intramolecular bond comprises a disulfide bond between the cysteines. However, organic chemists and peptide chemists are capable of synthesizing intramolecular bonds between a wide variety of amino acids using conventional techniques.

Exemplary peptidomimetic inhibitors of the VEGF-C and/or VEGF-D signaling pathways suitable for practicing the invention include those described in U.S. Pat. No. 7,045,133 (May 16, 2006), incorporated herein by reference in its entirety. That patent describes, for example, monomeric monocyclic peptide inhibitors based on loop 1, 2 or 3 of VEGF-D. A preferred peptide interferes with at least the activity of VEGF-D and VEGF-C mediated by VEGF receptor-2 and VEGF receptor-3 (VEGFR-3). A particularly preferred peptide interferes with the activity of VEGF-D, VEGF-C and VEGF mediated by VEGFR-2 and the activity of VEGF-D and VEGF-C mediated by VEGFR-3. The patent also describes a dimeric bicyclic peptide inhibitor which comprises two monomeric monocyclic peptides, each individually based on loop 1, 2 or 3 of VEGF-D, linked together. Such dimeric bicyclic peptides may comprise two monomeric monocyclic peptides which are the same or different. (See, for example, Table 1-3 of the '133 patent.) Exemplary peptides in Table 1 are reproduced below:

TABLE 1

Sequence and predicted and actual molecular masses (determined by mass spectrometry) of peptides synthesized

| number | sequence | mass predicted | mass actual [M + H] |
|---|---|---|---|
| 1 | CASELGKSTNTFC (SEQ ID NO: 5) | 1358.52 | 1360 |
| 2 | CNEESLIC (SEQ ID NO: 6) | 908.02 | 909.5 |
| 3 | CISVPLTSVPC (SEQ ID NO: 7) | 1116.37 | 1117.6 |
| 4 | CASELGKSTNTFCKPPC (SEQ ID NO: 8)<br>CASELGKSTNTFCKPPC (SEQ ID NO: 8) | 2793.18 | 2793.9 |
| 5 | CASELGKSTNTFCKPPC (SEQ ID NO: 8)<br>(SEQ ID NO: 9)<br>CCNEESLIC | 3566.09 | 3567.1 |
| 6 | CCNEESLIC (SEQ ID NO: 9)<br>CCNEESLIC (SEQ ID NO: 9) | 2019.6 | 2020.8 |
| 7 | CSVPLTSVC (SEQ ID NO: 10) | 905.41 | 907 |
| 8 | CVPLTSC (SEQ ID NO: 11) | 719.32 | 720.5 |
| 9 | CVPLTC (SEQ ID NO: 12) | 632.28 | 633.6 |
| 10 | CISVPLSVPC (SEQ ID NO: 13) | 1014.5 | 1015.4 |
| 11 | CISVPLVPC (SEQ ID NO: 14) | 927.47 | 928.3 |

Additional peptide inhibitors useful for practicing this invention are described in U.S. Pat. No. 7,611,711 (Nov. 3, 2009), incorporated herein by reference in its entirety. This patent describes peptides that bind VEGFR-3 and inhibit VEGFR-3 ligands (VEGF-C and -D) from binding and stimulating the receptor. For example, in one embodiment, the invention provides an isolated peptide comprising the formula: $X_1X_2X_3X_4X_5X_6X_7X_8$ (SEQ ID NO: 1), wherein $X_1$ through $X_8$ are amino acid residues, wherein the peptide binds to VEGFR3, and wherein $X_1$ through $X_8$ are defined as follows: the amino acid residue at $X_1$ is a glycine residue or a conservative substitution thereof; the amino acid residue at $X_2$ is a tyrosine residue or a conservative substitution thereof; the amino acid residue at $X_3$ is a tryptophan residue or a conservative substitution thereof; the amino acid residue at $X_4$ is a leucine residue or a conservative substitution thereof; the amino acid residue at $X_5$ is a threonine residue or a conservative substitution thereof; the amino acid residue at $X_6$ is an isoleucine residue or a conservative substitution thereof; the amino acid residue at $X_7$ is a tryptophan residue or a conservative substitution thereof; and the amino acid residue at $X_8$ is a glycine residue or a conservative substitution thereof. Preferred peptides are from 6 to 100 amino acids in length, e.g., 6, 7, 8, 9, 10, 11, 12, . . . 97, 98, 99, or 100 amino acids in length. The peptides may be made cyclic by the formation of at least one bond between non-adjacent amino acids. For example, in one variation, the peptides are formed with terminal cysteines which can be made to form an intramolecular disulfide bond. Thus, in one preferred embodiment, the peptide further comprises amino- and carboxy-terminal cysteine residues. For example, the peptide may comprise the amino acid sequence: $CX_1X_2X_3X_4X_5X_6X_7X_8C$ (SEQ ID NO: 2), wherein $X_1X_2X_3X_4X_5X_6X_7X_8$ are defined as above, and C represents cysteine. In an alternative embodiment, additional residues are attached to $X_1$ or $X_8$, within the terminal cysteines.

Preferred conservative substitutions for these peptide molecules include any of the following, in any combination: the conservative substitution at position $X_1$ is selected from isoleucine, valine, leucine, alanine, cysteine, phenylalanine, proline, tryptophan, tyrosine, norleucine and methionine; the conservative substitution at position $X_2$ is selected from isoleucine, valine, leucine, alanine, cysteine, glycine, phenylalanine, proline, tryptophan, norleucine and methionine; the conservative substitution at position $X_3$ is selected from isoleucine, valine, leucine, alanine, cysteine, glycine, phenylalanine, proline, tyrosine, norleucine and methionine; the conservative substitution at position $X_4$ is selected from isoleucine, valine, alanine, cysteine, glycine, phenylalanine, proline, tryptophan, tyrosine, norleucine and methionine; the conservative substitution at position $X_5$ is selected from asparagine, glutamine, and serine; the conservative substitution at position $X_6$ is selected from valine, leucine, alanine, cysteine, glycine, phenylalanine, proline, tryptophan, tyrosine, norleucine or methionine; the conservative substitution at position $X_7$ is selected from isoleucine, valine, leucine, alanine, cysteine, glycine, phenylalanine, proline, tyrosine, norleucine and methionine; and the conservative substitution at position $X_8$ is selected from isoleucine, valine, leucine, alanine, cysteine, phenylalanine, proline, tryptophan, tyrosine, norleucine and methionine.

In on preferred embodiments, the invention provides an isolated peptide comprising the sequence $Y_1$GYWLTIWG$Y_2$ (SEQ ID NO: 3), wherein $Y_1$ are amino acids. In one variation, the peptide is made cyclic by a bond between $Y_1$ and $Y_2$. In a specific preferred embodiment, the peptide comprises the sequence CGYWLTIWGC (SEQ ID NO: 4). Other specific examples of peptides described in that patent include peptides that comprise any of the following sequences: SGYWWDTWF (SEQ ID NO: 15), SCYWRDTWF (SEQ ID NO: 16), KVGWSSPDW (SEQ ID NO: 17), FVGWTKVLG (SEQ ID NO: 18), YSSSMRWRH (SEQ ID NO: 19), RWRGNAYPG (SEQ ID NO: 20), SAVFRGRWL (SEQ ID NO: 21), WFSASLRFR (SEQ ID NO: 22), WQLGRNWI (SEQ ID NO: 23), VEVQITQE (SEQ ID NO: 24), AGKASSLW (SEQ ID NO: 25), RALDSALA (SEQ ID NO: 26), YGFEAAW (SEQ ID NO: 27), YGFLWGM (SEQ ID NO: 28), SRWRILG (SEQ ID NO: 29), HKWQKRQ (SEQ ID NO: 30), MDPWGGW (SEQ ID NO: 31), RKVWDIR (SEQ ID NO: 32), VWDHGV (SEQ ID NO: 33), CWQLGRNWIC (SEQ ID NO: 34), CVEVQITQEC (SEQ ID NO: 35), CAGKASSLWC (SEQ ID NO: 36), CRALDSALAC (SEQ ID NO: 37), CYGFEAAWC (SEQ ID NO: 38), CYGFLWGMC (SEQ ID NO: 39), CSRWRILGC (SEQ ID NO: 40), CHKWQKRQC (SEQ ID NO: 41), CMDPWGGWC (SEQ ID NO: 42), CRKVWDIRC (SEQ ID NO: 43), CVWDHGVC (SEQ ID NO: 44), and CGQMCTVWCSSGC (SEQ ID NO: 45), and conservative substitution-analogs thereof, wherein the peptide binds human VEGFR-3. Preferred peptides comprise these exact amino acid sequences, or sequences in which only one or only two conserved substitutions have been introduced. In another preferred variation, the peptides are preferred with amino- and carboxy-terminal cysteines, which permit formation of cyclic molecules and dimers and multimers.

Nucleic Acid Molecules

Antisense Molecules

In yet another embodiment, the inhibitor of VEGF-C or VEGF-D activity, VEGFR-3-mediated signaling or lymphangiogenesis is an antisense molecule that reduces transcription and/or translation of a component of VEGF-C or VEGF-D activity, VEGFR-3-mediated signaling or lymphangiogenesis, thereby reducing VEGF-C or VEGF-D activity, VEGFR-3-mediated signaling or lymphangiogenesis.

The antisense molecule comprises RNA or DNA prepared using antisense technology, where, for example, an antisense RNA or DNA molecule acts to block directly the translation of mRNA by hybridizing to targeted mRNA and preventing protein translation. Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to reduce or block expression of a component of VEGF-C or VEGF-D activity, VEGFR-3-mediated signaling or lymphangiogenesis, and thus VEGF-C or VEGF-D activity, VEGFR-3-mediated signaling or lymphangiogenesis. Such oligonucleotides can also be delivered to cells such that the antisense RNA or DNA may be expressed in vivo to inhibit production of components of VEGF-C or VEGF-D activity, VEGFR-3-mediated signaling or lymphangiogenesis.

Inhibitors of VEGF-C or VEGF-D activity or signaling mediated by VEGFR-3, or lymphangiogenesis include antisense or sense oligonucleotides comprising a single-stranded nucleic acid sequence (either RNA or DNA) capable of binding to target mRNA (sense) or DNA (antisense) sequences. Such a fragment generally comprises about 10 to 40 nucleotides in length, preferably at least about 14 nucleotides, preferably from about 14 to 30 nucleotides.

Antisense or sense oligonucleotides further comprise oligonucleotides having modified sugar-phosphodiester backbones that are resistant to endogenous nucleases, or are covalently linked to other moieties that increases affinity of the oligonucleotide for a target nucleic acid sequence, or intercalating agents to modify binding specificities of the antisense or sense oligonucleotide for the target nucleotide sequence.

Antisense materials and methods are further described below, e.g., in the context of VEGFR-2 inhibitors. This discussion below also is applicable to antisense materials and methods for other targets, including VEGFR-3, VEGF-C, and VEGF-D.

Small Interfering RNA (siRNA)

In one embodiment, it is envisaged that siRNA will inhibit VEGF-C or VEGF-D activity, VEGFR-3-mediated signaling or lymphangiogenesis. "siRNA" or "RNAi" are double-stranded RNA molecules, typically about 21 nucleotides in length, that are homologous to a gene or polynucleotide that encodes the target gene and interfere with the target gene's expression. Interfering RNA materials and methods are further described below, e.g., in the context of VEGFR-2 inhibitors. This discussion below also is applicable to interfering RNA directed to other targets, including VEGFR-3, VEGF-C, and VEGF-D.

Nucleic Acid Molecules in Triple-Helix Formation

In another embodiment, the inhibitor of VEGF-C or VEGF-D activity, VEGFR-3-mediated signaling or lymphangiogenesis comprises nucleic acid molecules in triple-helix formation. Nucleic acid molecules in triple-helix formation used to inhibit transcription should be single-stranded and composed of deoxynucleotides. A DNA oligonucleotide is designed to be complementary to a region of the gene involved in transcription. The base composition of these oligonucleotides is designed such that it promotes triple-helix formation via Hoogsteen base-pairing rules, which generally require sizeable stretches of purines or pyrimidines on one strand of a duplex.

Ribozymes

In a related embodiment, the inhibitor of VEGF-C or VEGF-D activity, VEGFR-3-mediated signaling or lymphangiogenesis is a ribozyme that reduces transcription of a component of VEGF-C or VEGF-D activity or signaling mediated by VEGFR-3, or a lymphangiogenic component.

A "ribozyme" is an enzymatic RNA molecule capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques.

Small Molecule Inhibitors

In a further embodiment, the inhibitor of VEGF-C or VEGF-D activity, VEGFR-3-mediated signaling or lymphangiogenesis is a small molecule.

A "small molecule" is defined herein to have a molecular weight below about 2000 daltons, and preferably below about 500 Daltons. Potential inhibitors of VEGF-C or VEGF-D activity, VEGFR-3-mediated signaling or lymphangiogenesis include small molecules that bind to the active site, the receptor binding site, or growth factor or other relevant binding site of components of VEGF-C or VEGF-D activity or VEGFR-3-mediated signaling, or lymphangiogenesis, thereby blocking the normal biological activity of VEGF-C or VEGF-D, VEGFR-3-mediated signaling or lymphangiogenesis. Examples of small molecules include, but are not limited to, synthetic non-peptidyl organic or inorganic compounds.

Small molecule inhibitors of VEGF-C or VEGF-D activity, VEGFR-3-mediated signaling or lymphangiogenesis may be identified without undue experimentation using known techniques and chemically synthesized using known methodology. In this regard, it is noted that techniques for screening organic molecule libraries for molecules that are capable of binding to a polypeptide target are known in the art.

Inhibition of Receptor Availability for Ligand Binding Antibody Inhibitors

In one embodiment, the inhibitor of VEGF-C or VEGF-D activity, VEGFR-3-mediated signaling or lymphangiogenesis is an antibody. In a preferred embodiment, the inhibitor of VEGF-C or VEGF-D activity, VEGFR-3-mediated signaling or lymphangiogenesis is an anti-VEGFR-3 antibody that reduces VEGFR-3 availability for ligand binding.

Suitable antibodies for use in the methods of the invention and means for their production are disclosed in WO2000/021560 and WO1995/021868 and include a polyclonal or a monoclonal antibody that binds specifically to VEGFR-3 and blocks its signaling, a fragment of such an antibody, a chimeric antibody, a humanized antibody, and a bispecific antibody that binds specifically to VEGFR-3 and blocks its signaling and also binds to another antigen.

In a preferred embodiment, the antibody inhibitor is a humanized antibody. In another embodiment, the antibody inhibitor of VEGF-C or VEGF-D activity, VEGFR-3-mediated signaling or lymphangiogenesis comprises a Fab, Fab', or F(ab')$_2$ fragment, or a single chain Fv (scFv) fragment.

Persons skilled in the art will appreciate that in particular embodiments, the monoclonal antibody may comprise antibody 9D9F9, disclosed in WO2000/021560 or 2E11D11 disclosed in WO2003/006104. Alternatively monoclonal antibodies that specifically bind to VEGFR-3 and may be used according to the invention include antibodies MM0003-7G63, RM0003-5F63, C28G5, KLT9, ZMD.251, mF4-31C1 and hF4-3C5. A particularly preferred monoclonal antibody is hF4-3C5, a fully-humanized antagonist antibody to human VEGFR-3.

In an alternative embodiment, the inhibitor may comprise a bispecific antibody, particularly a diabody, that binds specifically to and neutralizes each of VEGFR-3 and a second target. One example of such a diabody is that derived from antibodies hF4-3C5 and IMC-1121, which binds specifically to and neutralizes each of VEGFR-3 and VEGFR-2.

An inhibitor of VEGF-C or VEGF-D activity, VEGFR-3-mediated signaling or lymphangiogenesis according to the present invention also includes in one embodiment an antibody, as described above, that inhibits or neutralizes the receptor tyrosine kinase activity of VEGFR-3.

Peptide and Peptide Mimetic Inhibitors

The person skilled in the art will appreciate that particular inhibitors of VEGF-C or VEGF-D activity, VEGFR-3-mediated signaling or lymphangiogenesis that can be employed in a particular embodiment of the present invention are disclosed in WO2000/021560, WO2001/052875, and WO2002/057299, which are incorporated herein by reference. In one embodiment, the inhibitor of VEGF-C or VEGF-D activity, VEGFR-3-mediated signaling or lymphangiogenesis comprises a peptide. Such a peptide to be used as an inhibitor of VEFC-C or VEGF-D activity, VEGFR-3-mediated signaling or lymphangiogenesis can be generated by random peptide synthesis, by recombinant means from random oligonucleotides, or a peptide may be selected from a phage display library, according to the disclosure of WO2002/057299 and WO2000/021560 and methods standard in the art. Such a peptide can be identified with the aid of the VEGFR-3 extracellular domain.

In a particular embodiment, the peptide inhibitor of VEGF-C or VEGF-D activity, VEGFR-3-mediated signaling or lymphangiogenesis comprises the amino acid sequence GYWX₁X₂X₃W (SEQ ID NO: 46), wherein X₁, X₂, and X₃ comprise amino acids and wherein the peptide binds VEGFR-3, according to WO2002/057299. In a related embodiment, the peptide inhibitor comprises the amino acid sequence GYWX₁X₂X₃WX₄ (SEQ ID NO: 47), wherein X₄ comprises an amino acid. In another embodiment, either of the preceding peptides may further comprise an amino- and carboxy-terminus cysteine residue. In a particular embodiment, the peptide comprises a cyclic peptide. In an alternative embodiment, the peptide comprises a peptide dimer that binds to VEGFR-3, and in a preferred form, the peptides comprising the dimer are the same, according to WO2002/057299.

In one embodiment, the peptidomimetic inhibitor is a monomeric monocyclic peptide inhibitor or dimeric bicyclic peptide inhibitor. Preferably, such peptidomimetic inhibitors are based on the peptide sequence of exposed loops of growth factor proteins, for example, loops 1, 2, and 3 of VEGF-D. In a preferred embodiment, the peptidomimetic inhibitor comprises any one of: CASELGKSTNTFC (SEQ ID NO 5); CNEESLIC (SEQ ID NO: 6); or CISVPLTSVPC (SEQ ID NO: 7).

In one embodiment, the peptide mimetic inhibitor is prepared by the methods disclosed in WO2001/052875 and WO2002/057299. Peptides that may be used as inhibitors of VEGF-D activity, VEGFR-3-mediated signaling or lymphangiogenesis are disclosed in WO2000/021560. Such peptides include a polypeptide comprising a fragment or analog of a vertebrate VEGF-C polypeptide, wherein the polypeptide and fragment or analog are capable of binding to VEGFR-3, but do not activate signaling, and a polypeptide comprising a fragment or analog of a vertebrate VEGF-C or VEGF-D polypeptide, wherein the polypeptide and fragment or analog are capable of binding to VEGFR-3, but do not activate signaling.

The person skilled in the art will appreciate that inhibitors of VEGF-D activity, VEGFR-3-mediated signaling or lymphangiogenesis inhibitors according to WO2002/057299 include peptides comprising the sequence Y₁GYWLTIWGY₂ (SEQ ID NO: 3), wherein Y₁ and Y₂ are amino acids. In one variation, the peptide is made cyclic by a bond between Y₁ and Y₂. In a specific preferred embodiment, the peptide comprises the sequence CGYWLTIWGC (SEQ ID NO: 4). Other peptide inhibitors comprise any of the following amino acid sequences: SGYWWDTWF (SEQ ID NO: 15), SCYWRDTWF (SEQ ID NO: 16), KVGWSSPDW (SEQ ID NO: 17), FVGWTKVLG (SEQ ID NO: 18), YSSSMRWRH (SEQ ID NO: 19), RWRGNAYPG (SEQ ID NO: 20), SAVFRGRWL (SEQ ID NO: 21), WFSASLRFR (SEQ ID NO: 22), WQLGRNWI (SEQ ID NO: 23), VEVQITQE (SEQ ID NO: 24), AGKASSLW (SEQ ID NO: 25), RALDSALA (SEQ ID NO: 26), YGFEAAW (SEQ ID NO: 27), YGFLWGM (SEQ ID NO: 28), SRWRILG (SEQ ID NO: 29), HKWQKRQ (SEQ ID NO: 30), MDPWGGW (SEQ ID NO: 31), RKVWDIR (SEQ ID NO: 32), VWDHGV (SEQ ID NO: 33), CWQLGRNWIC (SEQ ID NO: 34), CVEVQITQEC (SEQ ID NO: 35), CAGKASSLWC (SEQ ID NO: 36), CRALDSALAC (SEQ ID NO: 37), CYGFEAAWC (SEQ ID NO: 38), CYGFLWGMC (SEQ ID NO: 39), CSRWRILGC (SEQ ID NO: 40), CHKWQKRQC (SEQ ID NO: 41), CMDPWGGWC (SEQ ID NO: 42), CRKVWDIRC (SEQ ID NO: 43), CVWDHGVC (SEQ ID NO: 44), CGQMCTVWCSSGC (SEQ ID NO: 45), or conservative substitutions-variants thereof. Preferred peptides comprise these exact amino acid sequences, or sequences in which only one or only two conserved substitutions have been introduced. In another preferred variation, the peptides comprise amino- and carboxy-terminal cysteines, which permit formation of cyclic molecules and dimers and multimers. In yet another variation, peptide inhibitors include the amino acid sequence GYWX₁X₂X₃W (SEQ ID NO: 46), wherein X, X₂, and X₃ comprise amino acids, the amino acid sequence GYWX₁XZX₃WX₄ (SEQ ID NO: 47), wherein X₄ comprises an amino acid. In still another variation, these peptides further comprise amino- and carboxy-terminal cysteine residues.

Nucleic Acid Inhibitors

In a preferred embodiment, the invention envisages use of a VEGFR-3 antisense RNA, as disclosed in WO2000/021560, to inhibit the translation of VEGFR-3-encoding mRNA to eliminate or downregulate levels of VEGFR-3. Similarly, siRNA or nucleic acids in triple helix formation could be used to reduce VEGFR-3 availability for ligand binding.

Small Molecule Inhibitors

In a preferred embodiment, the small molecule is a small molecule inhibitor of receptor tyrosine kinase activity. In a more preferred embodiment, the small molecule comprises PTK787/ZK22854, AZP2171, ZK991, KRN633, MAZ51, sorafenib, sunitinib (SU11248), axitinib (AG013736), vandetanib (ZD6474), or 3-(indole-3-yl)-4-(3,4,5-trimethoxyphenyl)-1H-pyrrole-2,5-dione.

Inhibition of Ligand Availability for Receptor Binding

Antibody Inhibitors

According to one embodiment, inhibition of VEGF-C or VEGF-D activity, VEGFR-3-mediated signaling or lymphangiogenesis can be achieved using antibodies that specifically bind and neutralize ligands for VEGFR-3, that is, VEGF-C and/or VEGF-D. Antibodies similar to anti-VEGFR-3 antibodies described above are contemplated. Suitable antibodies and their means for production are disclosed in WO2000/021560. The person skilled in the art will appreciate that antibodies that bind specifically to VEGF-D and may be used according to the invention include monoclonal antibodies 2F8, 4A5 (also known as VD1), 4E10, 5F12, 4H4 and 3C10 disclosed in WO2000/037025. A particularly preferred antibody is 4A5, and in particular, a humanized version thereof. In another embodiment, the chimeric or humanized antibody comprises SEQ ID NO: 56 and SEQ ID NO: 57, or the antibody comprises any one of SEQ ID NOs: 58 to 60 and any one of SEQ ID NOs: 61 to 63, as disclosed in WO2005/087177. Alternatively monoclonal antibodies that may be used according to the invention include 28AT743.288.48, MM0007-7E79, RM0007-8C35, 78902, 78923, 78939, and 90409.

Similarly, monoclonal antibodies that bind VEGF-C may be employed. The anti-VEGF-C antibodies will specifically bind to human VEGF-C or a biologically active fragment thereof, e.g. the mature fully-processed form. Such binding will partially or fully block, neutralize, reduce or antagonize VEGF-C activity. Suitable examples of such antibodies include antibodies 103, MM0006-2E65 and 193208. Further examples of such antibodies are found in U.S. Pat. No. 7,208,582 and U.S. Pat. No. 7,109,308.

One example of an anti-VEGF-C antibody is a monoclonal antibody that competitively inhibits the binding to VEGF-C of monoclonal anti-VEGF-C antibody 69D09 produced by hybridoma ATCC PTA-4095 or having the heavy and light chain amino acid sequences as follows:

```
                                                        SEQ ID NO: 48
EVRLLESGGG   LVQPGGSLRL   SCAASGFTFR   PRAMAWVRQA   PGKGLEWVSS
        10           20           30           40           50

ISAQGASAYY   ADSVKGRFTI   SRDNSKNTLY   LQMNSLRAED   TAVYYCARDL
        60           70           80           90          100

SVSGFGPWGR   GTMVTVSSAS   TKGPSVFPLA   PSSKSTSGGT   AALGCLVKDY
       110          120          130          140          150

FPEPVTVSWN   SGALTSGVHT   FPAVLQSSGL   YSLSSVVTVP   SSSLGTQTYI
       160          170          180          190          200

CNVNHKPSNT   KVDKRVEPKS   CDKTHTCPPC   PAPELLGGPS   VFLFPPKPKD
       210          220          230          240          250

TLMISRTPEV   TCVVVDVSHE   DPEVKFNWYV   DGVEVHNAKT   KPREEQYNST
       260          270          280          290          300

YRVVSVLTVL   HQDWLNGKEY   KCKVSNKALP   APIEKTISKA   KGQPREPQVY
       310          320          330          340          350

TLPPSREEMT   KNQVSLTCLV   KGFYPSDIAV   EWESNGQPEN   NYKTTPPVLD
       360          370          380          390          400

SDGSFFLYSK   LTVDKSRWQQ   GNVFSCSVMH   EALHNHYTQK   SLSLSPGK
       410          420          430          440          448
```

Sequence of Anti-VEGF-C Antibody Heavy Chain

```
                                                        SEQ ID NO: 49
SYELTQPPSS   SGTPGQRVTI   SCSGSSSNIG   RHTVSWYQQV   PGTAPKLLIY
        10           20           30           40           50

SDDHRPSGVP   DRFSASKSGT   SASLTITGLQ   SEDEADYYCA   AWDDSLNGPW
        60           70           80           90          100

VFGGGTKLTV   LGQPKAAPSV   TLFPPSSEEL   QANKATLVCL   ISDFYPGAVT
       110          120          130          140          150

VAWKADSSPV   KAGVETTTPS   KQSNNKYAAS   SYLSLTPEQW   KSHRSYSCQV
       160          170          180          190          200

THEGSTVEKT   VAPTECS
       210       217
```

Sequence of Anti-VEGF-C Antibody Light Chain

Another example of an anti-VEGF-C antibody is a monoclonal antibody that binds to the same epitope as the monoclonal anti-VEGF-C antibody 69D09 produced by hybridoma ATCC PTA-4095 or a monoclonal antibody having the heavy and light chain amino acid sequences shown above. In one embodiment, the anti-VEGF-C antibody is a fully-human anti-VEGF-C monoclonal antibody, including but not limited to 69D09 antibody or fragment thereof. The anti-VEGF-C antibody may be a humanized antibody.

Preferably, the anti-VEGF-C antibody is a human antibody produced by deposited hybridoma ATC PTA-4095 (also referred to herein as "VGX-100") or having the heavy and light chain amino acid sequences shown above.

Alternatively, antibodies may bind proprotein convertases, enzymes responsible for processing VEGF-C and VEGF-D from their prepro-forms to their activated forms, and reduce, inhibit or neutralize such activity thereby limiting the amount of proteolytically processed ligand available for binding to VEGFR-3. Again, antibodies corresponding with anti-VEGFR-3 antibodies described above are envisaged. Such antibodies are disclosed in WO05/112971 and include neutralizing antibodies to inhibit the biological action of proprotein convertases.

Peptide Inhibitors

Inhibitors of VEGF-C or VEGF-D activity, VEGFR-3-mediated signaling or lymphangiogenesis as used in the present invention include inhibitors of proprotein convertases. As noted, one class of inhibitor of proprotein convertases comprises antibodies. Another class of inhibitor of proprotein convertases includes peptide inhibitors.

Peptide inhibitors of proprotein convertases are disclosed in WO05/112971 and include prosegments of proprotein convertases, inhibitory variants of anti-trypsin and peptidyl haloalkylketone inhibitors.

Representative inhibitory prosegments of proprotein convertases include the inhibitory prosegments of PC5A (also known as PC6A), PC5B (also known as PC6B), PACE4, PC1 (also known as PC3), PC2, PC4, PC7 and Furin. A representative inhibitory variant of anti-trypsin is α-1 antitrypsin Portland, an engineered variant of naturally occurring antitrypsin that inhibits multiple proprotein convertases. Representative peptidyl halomethyl ketone inhibitors include decanoyl-Arg-Val-Lys-Arg-chloromethylketone (Dec-RVKR-CMK), decanoyl-Phe-Ala-Lys-Arg-chloromethylketone (Dec-FAKR-CMK), decanoyl-Arg-Glu-Ile-Arg-chloromethylketone (Dec-REIR-CMK), and decanoyl-Arg-Glu-Lys-Arg-chloromethylketone (Dec-REKR-CMK). These inhibitors of proprotein convertases, such as Dec-RVKR-CMK or the inhibitory prosegments of proprotein convertases, can be used to block the activation of VEGF-C and VEGF-D and thereby inhibit VEGF-C or VEGF-D activity, VEGFR-3-mediated signaling or lymphangiogenesis induced by partially processed or fully processed VEGF-C or VEGF-D.

Soluble Receptors

According to another embodiment, VEGF-C or VEGF-D activity, VEGFR-3-mediated signaling or lymphangiogenesis can be inhibited using soluble receptors that bind VEGFR-3 ligands. Soluble receptors capable of binding VEGF-C and VEGF-D, thereby inhibiting VEGF-C or VEGF-D activity or signaling via VEGFR-3, are disclosed in WO2000/023565, WO2000/021560, WO2002/060950 and WO2005/087808. Such inhibitors of VEGF-D activity, VEGFR-3-mediated signaling or lymphangiogenesis inhibitors include soluble VEGFR-2, VEGFR-3, NRP-1, and NRP-2.

According to one embodiment, soluble receptor constructs useful for practicing the present invention are described in International Patent Application No. PCT/US02/01784, filed Jan. 22, 2002 (WO 2002/060950, published Aug. 8, 2002), incorporated here by reference in its entirety, and in International Patent Application No. PCT/US2005/007741, filed Mar. 7, 2005 (WO 2005/087808, published Sep. 22, 2005), incorporated here by reference in its entirety. As described therein, the receptor tyrosine kinases that bind the VEGF or PDGF family of ligands include an extracellular domain, a hydrophobic transmembrane domain, and an intracellular domain. The extracellular domain can be used as a ligand trap by formulating it as a soluble formulation, optionally fused with an additional component, such as polyethylene glycol or an antibody constant region to improve serum half-life.

The complete ECD of PDGFRs and VEGFRs is not required for ligand (growth factor) binding. The ECD of VEGFR-1 (R-1) and VEGFR-2 (R-2) consists of seven Ig-like domains and the ECD of VEGFR-3 (R-3) has six intact Ig-like domains—D5 of R-3 is cleaved post-translationally into disulfide linked subunits leaving VEGFR-3. Veikkola, T., et al., Cancer Res. 60:203-212 (2000). In general, receptor fragments of at least the first three Ig-like domains for this family are sufficient to bind ligand. The PDGFRs have five Ig-like domains.

TABLE 1A

Immunoglobulin-like domains for VEGFR-2 and VEGFR-3

|    | R-2 SEQ ID NO: 50 positions | R-2 SEQ ID NO: 51 positions | R-3 SEQ ID NO: 54 positions | R-3 SEQ ID NO: 55 positions |
| --- | --- | --- | --- | --- |
| D1 | 145-316 | 48-105 | 158-364 | 47-115 |
| D2 | 436-610 | 145-203 | 479-649 | 154-210 |
| D3 | 724-931 | 241-310 | 761-961 | 248-314 |
| D4 | 1039-1204 | 346-401 | 1070-1228 | 351-403 |
| D5 | 1321-1600 | 440-533 | 1340-1633 | 441-538 |
| D6 | 1699-1936 | 566-645 | 1739-1990 | 574-657 |
| D7 | 2050-2221 | 683-740 | 2102-2275 | 695-752 |

Soluble receptor constructs for use as a ligand trap for VEGF-C or -D preferably comprise at least one Ig-like domain of a VEGFR as described in Table 2, to as many as seven. The construct optionally will include sequence before the most N-terminally positioned Ig-like domain, optionally will include sequence beyond the most C-terminally Ig-like domain, and optionally will include sequence between the Ig-domains as well. Variants, e.g., with one or more amino acid substitutions, additions, or deletions of an amino acid residue, are also contemplated. Likewise, chimeras, e.g., combinations of Ig-like domains from different receptors, are contemplated. In some embodiments, the soluble receptor comprises a receptor fragment comprising at least the first three Ig-like domains of a receptor tyrosine kinase.

In one embodiment, referring specifically to the VEGFR-3 sequence, soluble receptors are contemplated in which the soluble receptor polypeptide comprises a portion of a mammalian, preferably human, VEGFR-3 extracellular domain (EC) wherein the portion binds to at least one VEGFR-3 ligand and comprises at least the first, second and third Ig-like domains of the VEGRF-3-EC, and wherein the polypeptide lacks VEGFR-3 Ig-like domains 4-7 and preferably any transmembrane domain.

In another embodiments, referring specifically to the VEGFR-3 sequence, soluble receptors are contemplated in which the soluble receptor polypeptide comprises an amino acid sequence at least 90, 91, 92, 93, 94, or 95% identical to a VEGFR-3 fragment, wherein the VEGFR-3 fragment comprises an amino acid sequence consisting of a portion of SEQ ID NO: 53, wherein the carboxy-terminal residue of the fragment is selected from the group consisting of positions 211 to 247 of SEQ ID NO: 53, and wherein the fragment and the polypeptide bind VEGF-C or VEGF-D. In some variations, the fragment has an amino terminal amino acid selected from the group consisting of positions of 1 to 47 of SEQ ID NO: 53. In some variations, the VEGFR-3 fragment used to make the soluble receptor has an amino terminal residue selected from the group consisting of positions 1 to 47 of SEQ ID NO: 53, and a carboxy-terminal residue selected from the group consisting of positions 226 to 775 of SEQ ID NO: 53, wherein VEGFR-3 fragment binds at least one of VEGF-C and VEGF-D. Specific peptides include a fragment of R-3 defined by positions 1-226, positions 1-229, and positions 1-329, positions 47-224, positions 47-225, positions 47-226, positions 47-227, positions 47-228, positions 47-229, positions 47-230, positions 47-231, positions 47-232, positions 47-236, positions 47-240, positions 47-245, positions 47-314, positions 47-210, and positions 47-247.

Soluble receptors that bind VEGF-C and -D can also be constructed from a VEGFR-2 amino acid sequence. Referring to the human VEGFR-2 sequence (SEQ ID NO: 51), exemplary R2 fragments for use in a soluble receptor have an amino terminal residue selected from the group consisting of positions 1 to 118 of SEQ ID NO: 51, and a carboxy-terminal residue selected from the group consisting of positions 326 to 764 of SEQ ID NO: 51, wherein VEGFR-2 fragment binds at least one of VEGF-C and VEGF-D (and may also bind VEGF-A or other VEGF's). In some variations, the amino terminal residue from the VEGFR-2 sequence is selected from the group consisting of positions 1 to 192 of SEQ ID NO: 51, and the carboxy terminal residue is selected from the group consisting of positions 393 to 764 of SEQ ID NO: 51. In still other variations, the amino-terminal residue is selected from the group consisting of positions 1 to 48 of SEQ ID NO: 51, and a carboxy terminal residue selected from the group consisting of positions 214 to 764 of SEQ ID NO: 51. In some embodiments, the soluble receptor based on VEGFR-2 comprises a VEGFR-2 sequence selected from positions 24-326, positions 118-326, positions 118-220, positions 118-226, and positions 118-232, positions 106-240, positions 112-234, positions 114-220, positions 115-220, positions 116-222, positions 117-220, positions 118-221, positions 118-

222, positions 118-223, positions 118-224, positions 118-228, positions 48-203, positions 145-310 and positions 48-310.

As described in WO 2005/087808, these or other exemplary soluble receptor constructs can be combined to make multivalent binding constructs. The receptor fragments, binding constructs, and other peptide molecules may be fused to heterologous peptides to confer various properties, e.g., increased solubility, modulation of clearance, targeting to particular cell or tissue types. In some embodiments, the receptor fragment is linked to a Fc domain of IgG or other immunoglobulin. In some embodiments, a receptor fragment is fused to alkaline phosphatase (AP). Methods for making Fc or AP fusion constructs are found in WO 02/060950.

Nucleic Acid Inhibitors

In another embodiment of the invention, antisense oligonucleotides are used as inhibitors of proprotein convertases. The antisense oligonucleotides preferably inhibit expression of proprotein convertases by inhibiting transcription or translation of proprotein convertases. In a further embodiment, the antagonizing agent is small interfering RNAs (siRNA, also known as RNAi, RNA interference nucleic acids). Also contemplated are methods of inhibiting the target gene expression or target protein function utilizing ribozymes and triplex-forming nucleic acid molecules.

Similarly, in a related embodiment, antisense, siRNA and ribozyme inhibitors directed to VEGF-C and/or VEGF-D are included as inhibitors of VEGF-C or VEGF-D activity, VEGFR-3-mediated signaling or lymphangiogenesis exerting their effects by reducing transcription and/or translation of VEGF-C and VEGF-D.

Peptide and Peptide Mimetic Inhibitors

According to one embodiment, the inhibitor to be used in the invention comprises a peptide that reduces the availability of ligand to bind to VEGFR-3. Such a peptide can be generated by random peptide synthesis, by recombinant means from random oligonucleotides, or a peptide may be selected from a phage display library by methods standard in the art. In a particular embodiment, the peptide will be derived from VEGFR-3 or VEGFR-2 and will bind specifically to VEGF-C or VEGF-D such that the ligand available for binding to native VEGFR-3 is reduced. Such a peptide may be identified with the aid of the VEGF-C or VEGF-D.

Small Molecule Inhibitors

In one embodiment, the small molecule inhibitor is a small molecule inhibitor of a proprotein convertase. In a particular embodiment, the proprotein convertase is furin and the small molecule comprises B3 (CCG8294, naphthofluorescein disodium) or a derivative of 2,5-dideoxystreptamine.

Tyrosine Kinase Inhibitors

In another embodiments, the anti-lymphangiogenic agent is a tyrosine kinase inhibitor that inhibits VEGFR-3 activity, which means an inhibitor of receptor tyrosine kinase activity that selectively or non-selectively reduces the tyrosine kinase activity of a VEGFR-3 receptor. Such an inhibitor generally reduces VEGFR-3 tyrosine kinase activity without significantly effecting the expression of VEGFR-3 and without effecting other VEGFR-3 activities such as ligand-binding capacity. A VEGFR-3 kinase inhibitor can be a molecule that directly binds the VEGFR-3 catalytic domain, for example, an ATP analog. A VEGFR-3 kinase inhibitor can bind the VEGFR-3 catalytic domain through one or more hydrogen bonds similar to those anchoring the adenine moiety of ATP to VEGFR-3 (Engh et al., J. Biol. Chem. 271:26157-26164 (1996); Tong et al., Nature Struc. Biol. 4:311-316 (1997); and Wilson et al., Chem. Biol. 4:423-431 (1997)). A VEGFR-3 kinase inhibitor also can bind the hydrophobic pocket adjacent to the adenine binding site (Mohamedi et al., EMBO J. 17:5896-5904 (1998); Tong et al., supra, 1997; and Wilson et al., supra, 1997).

VEGFR-3 kinase inhibitors useful in the invention include specific VEGFR-3 kinase inhibitors such as indolinones that differentially block VEGF-C and VEGF-D induced VEGFR-3 kinase activity compared to that of VEGFR-2. Such specific VEGFR-3 kinase inhibitors, for example, MAE106 and MAZ51 can be prepared as described in Kirkin et al., Eur. J. Biochem. 268:5530-5540 (2001). Additional VEGFR-3 kinase inhibitors, including specific, selective and non-selective inhibitors, are known in the art or can be identified using one of a number of well known methods for assaying for receptor tyrosine kinase inhibition.

As an example, a VEGFR-3 kinase inhibitor can be identified using a well known ELISA assay to analyze production of phosphorylated tyrosine as described, for example in Hennequin et al., J. Med. Chem. 42:5369-5389 (1999) and Wedge et al., Cancer Res. 60:970-975 (2000). Such an assay can be used to screen for molecules that inhibit VEGFR-3 in preference to other vascular endothelial growth factor receptors such as VEGFR-1 and in preference to unrelated tyrosine kinases such as fibroblast growth factor receptor1 (FGFR1). Briefly, molecules to be screened can be incubated for 20 minutes at room temperature with a cytoplasmic receptor domain in a HEPES (pH 7.5) buffered solution containing 10 mM $MnCl_2$ and 2 µM ATP in 96-well plates coated with a poly(Glu, Ala, Tyr) 6:3:1 random copolymer substrate (SIGMA; St. Louis, Mo.). Phosphorylated tyrosine can be detected by sequential incubation with mouse IgG anti-phosphotyrosine antibody (Upstate Biotechnology; Lake Placid, N.Y.), a horseradish peroxidase-linked sheep anti-mouse immunoglobulin antibody (Amersham; Piscataway, N.J.), and 2,2'azino-bis (3-ethylbenzthiazoline-6-sulfonic acid) (Roche Molecular Biochemicals, Indianapolis, Ind.). In such an in vitro kinase assay, the source of VEGFR-3 can be, for example, a lysate prepared from an insect cell infected with recombinant baculovirus containing a cytoplasmic receptor domain, for example, encoding residues 798 to 1363 of human VEGFR-3.

The term VEGFR-3 kinase inhibitor, as used herein, encompasses specific, selective and non-selective inhibitors of VEGFR-3. A specific VEGFR-3 kinase inhibitor reduces the tyrosine kinase activity of VEGFR-3 in preference to the activity of most or all unrelated receptor tyrosine kinases such as FGFR1 and in preference to the activity of the vascular endothelial growth factor receptors, VEGFR-1 and VEGFR-2. A selective VEGFR-3 kinase inhibitor reduces the tyrosine kinase activity of VEGFR-3 in preference to most or all unrelated receptor tyrosine kinases such as FGFR1. Such a selective VEGFR-3 inhibitor can have an $IC_{50}$ for inhibition of an isolated VEGFR-3 cytoplasmic domain that is, for example, at least 10-fold less than the $IC_{50}$ for both VEGFR-1 and VEGFR-2. In particular embodiments, the invention provides a selective VEGFR-3 kinase inhibitor having an $IC_{50}$ for inhibition of an isolated VEGFR-3 cytoplasmic domain that is at least 20-fold, 30-fold, 40-fold, 50-fold, 100-fold, 200-fold, 300-fold, 400-fold or 500-fold less than the $IC_{50}$ for both VEGFR-1 and VEGFR-2. In contrast, a non-selective VEGFR-3 kinase inhibitor reduces the tyrosine kinase activity of VEGFR-1 or VEGFR-2 or both to a similar extent as VEGFR-3.

Antibody Inhibitors Affecting Ligand—Receptor Complex

In one embodiment, the invention includes use of bispecific antibodies, as described above, as inhibitors of VEGF-C or VEGF-D activity, VEGFR-3-mediated signaling or lymphangiogenesis, specifically inhibiting ligand-receptor complexes.

Suitable antibodies and their means for production are disclosed in WO2000/021560 and include a bispecific antibody that binds specifically to an epitope or epitopes derived from a VEGFR-3-(VEGFR-3 ligand) complex (receptor-ligand complex) and blocks VEGFR-3 signaling.

Inhibition of Co-Receptor Interaction

Antibody Inhibitors Affecting Co-Receptors of VEGFR-3

In a further embodiment, inhibitors of VEGF-C or VEGF-D activity, VEGFR-3-mediated signaling or lymphangiogenesis include antibodies, as described above, that bind specifically to and reduce, inhibit or neutralize co-receptor binding to VEGFR-3. Such antibodies may be directed to a co-receptor, a ligand-co-receptor binary complex, a co-receptor-receptor binary complex, or a ligand-co-receptor-receptor ternary complex. Co-receptors include NRP-1 and NRP-2. The person skilled in the art will understand that monoclonal antibodies that specifically bind NRP-1 or NRP-2 and may be used according to the invention include antibodies 1B3, 3G6-2C5, AD5-17F6, 446915, 446921, 130603, 130604, 96009, 3B8, 54, 257103, 257107, A-12, and C-9. Alternatively, a bispecific antibody which specifically binds to NRP-2 receptor and a VEGF-C polypeptide, as disclosed in WO2003/029814, may be used according to the invention.

Peptide Inhibitors Affecting Co-Receptors of VEGFR-3

In another embodiment, a peptide inhibitor comprising a peptide dimer may target one or more receptors and/or co-receptors. Co-receptors include NRP-1 and NRP-2. As disclosed in WO2002/057299, in a particular embodiment, the peptide dimer comprises one peptide that binds VEGFR-3 and a second peptide that binds to any one of VEGFR-1, VEGFR-2, NRP-1, or NRP-2.

Small Molecule and Nucleic Acid Inhibitors Affecting Co-Receptors of VEGFR-3

According to the present invention, it is also envisaged that small molecules, antisense molecules, siRNA and ribozymes, as described above, can be utilized as inhibitors of VEGF-D activity, VEGFR-3-mediated signaling or lymphangiogenesis by targeting co-receptors that interact with VEGFR-3. Such co-receptors include NRP-1 and NRP-2.

Inhibition of Downstream Signaling

Alternatively, an inhibitor of VEGF-C or VEGF-D activity, VEGFR-3-mediated signaling or lymphangiogenesis according to any of the foregoing descriptions may disrupt downstream intracellular VEGFR-3 signaling, as disclosed in WO2000/021560.

Therapeutic Uses of the Anti-Lymphangiogenic Agents

In yet another embodiment, the invention provides numerous methods of using the anti-lymphangiogenic agents described herein. Generally speaking, the anti-lymphangiogenic agents described herein are useful for inhibiting cellular processes that are mediated through signal transduction through VEGFR-2 or VEGFR-3 for prophylaxis or therapy of dry eye disease.

Thus, in one variation, described herein is a method of prophylaxis or therapy for dry eye disease comprising administering to a subject in need of prophylaxis or therapy for dry eye disease a composition comprising an anti-lymphangiogenic agent. Preferably, the amount of the anti-lymphangiogenic agent employed is effective to inhibit the binding of VEGF-C and/or VEGF-D ligand to VEGFR-3 or the stimulatory effect of VEGF-C and/or VEGF-D on VEGFR-3.

Dose response studies permit accurate determination of a proper quantity of anti-lymphangiogenic agent to employ. Effective quantities can be estimated, for example, from measurements of the binding affinity of a polypeptide for a target receptor, of the quantity of receptor present on target cells, of the expected dilution volume (e.g., patient weight and blood volume for in vivo embodiments), and of polypeptide clearance rates. For example, existing literature regarding dosing of anti-VEGF-C antibodies known also provides guidance for dosing of the anti-lymphangiogenic agents described herein.

The anti-lymphangiogenic agent described herein can be administered purely as a prophylactic treatment to prevent dry eye disease in subjects at risk for developing dry eye disease, or as a therapeutic treatment to subjects afflicted with dry eye disease, for the purpose of inhibiting lymphangiogenesis in the eye of a subject in need thereof.

Subjects who are at risk for developing dry eye disease include subjects considering or who have already undergone refractive surgery; subjects over the age of sixty five; female subjects experiencing hormonal changes brought on by pregnancy, lactation, oral contraceptives, menstruation and post-menopause; subjects afflicted with rheumatoid arthritis, diabetes, thyroid abnormalities, asthma, cataracts, glaucoma or lupus; subjects taking medication(s) that decrease the body's ability to produce lubricating tears such as decongestants, antidepressants, antihistamines, blood pressure medication, oral contraceptives, diuretics, ulcer medication, tranquilizers and beta blockers; subjects that wear contact lenses; subjects exposed to environmental conditions that increase tear evaporation such as smoke, fluorescent light, air pollution, wind, heat, air conditioning and dry climates; and subjects that are heavy computer users (i.e., subjects that spend hours staring at computer displays that ignore their normal blinking process.

In one embodiment, described herein is a method of inhibiting dry eye disease in a subject at risk for developing dry eye disease comprising identifying a subject as being at risk for developing dry eye disease and administering an anti-lymphangiogenic agent to the subject. The amount of the anti-lymphangiogenic agent administered to the subject is preferably in an amount effective to inhibit the development of dry eye disease in the subject.

In another embodiment, described herein is a method of selecting a therapeutic regimen for a subject in need thereof comprising screening a subject for one or more symptoms of dry eye disease and prescribing for the subject administration of a composition comprising an anti-lymphangiogenic agent described herein. In another embodiment, described herein is a method of treating a subject affected with dry eye disease comprising identifying a subject as having one or more symptoms of dry eye disease and administering a composition comprising an anti-lymphangiogenic agent to the subject. Symptoms associated with dry eye disease include, but are not limited to, foreign body sensation, burning, itching, irritation, redness, eye pain, blurred vision, degraded vision, excessive tearing, dryness and a sandy-gritty eye irritation that gets worse as the day goes on.

In some embodiments, the methods described herein do not include administering an anti-lymphangiogenic agent as described herein to a subject that has undergone corneal transplant surgery.

In some embodiments, the methods described herein further comprise prescribing (or administering) a standard of care regimen for the treatment of dry eye disease. In the context of methods described herein, "standard of care" refers to a treatment that is generally accepted by clinicians for a certain type of patient diagnosed with a type of illness. For dry eye disease, for example, an aspect of the invention is to improve standard of care therapy with co-therapy with anti-lymphangiogenic agents described herein that inhibit lymphangiogenesis. Exemplary standard of care regimens for dry eye disease include, but are not limited to, eyelid hygiene, topical antibiotics (including, but not limited to erythromycin or bacitracin ointments), oral tetracyclines (tetracycline, doxycycline, or minocycline), anti-inflammatory compounds (including, but not limited to, cyclosporine) and corticosteroids.

Also contemplated are methods of treating a subject with dry eye disease that is hypo-responsive to a standard of care regimen for the treatment of dry eye disease comprising administering an anti-lymphangiogenic agent to the subject in an amount effective to treat dry eye disease.

In a preferred embodiment, the mammalian subject is a human subject. Practice of methods of the invention in other mammalian subjects, especially mammals that are conventionally used as models for demonstrating therapeutic efficacy in humans (e.g., primate, porcine, canine, or rabbit animals), is also contemplated.

Combination Therapy

Combination therapy embodiments of the invention include products and methods. Exemplary combination products include two or more agents formulated as a single composition or packaged together in separate compositions, e.g., as a unit dose package or kit. Exemplary combination methods include prescribing for administration, or administration of two or more agents simultaneously or in tandem.

A combination of an anti-lymphangiogenic agent with one or more additional therapeutic agents in the methods described herein may reduce the amount of either agent needed as a therapeutically effective dosage, and thereby reduce any negative side effects the agents may induce in vivo. Combination therapy preferably results in improved efficiency compared to either agent alone. Additional therapeutics or second agents contemplated for use in combination with an anti-lymphangiogenic agent described herein include a VEGFR-2 inhibitor product, a tyrosine kinase inhibitor that inhibits VEGFR-2 and/or VEGFR-3 signaling, an anti-inflammatory agent; an immunosuppressive agent (e.g., cyclosporine), an angiogenesis inhibitor, an antibiotic, and a standard of care regimen for the treatment of dry eye disease.

A. Standard of Care for Regimen for Treatment of Dry Eye Disease

In one embodiment, methods described herein optionally comprise administering a standard of care therapeutic to the subject. In some embodiments, the standard of care therapeutic and the anti-lymphangiogenic agent are co-administered in a single composition. In other embodiments, the standard of care therapeutic is administered as a separate composition from the anti-lymphangiogenic agent.

In the context of methods of the invention, "standard of care" refers to a treatment that is generally accepted by clinicians for a certain type of patient diagnosed with a type of illness. For dry eye disease, for example, an aspect of the invention is to improve standard of care therapy with co-therapy with anti-lymphangiogenic agents described herein that inhibit lymphangiogenesis. Exemplary standard of care regimens for dry eye disease include, but are not limited to, eyelid hygiene, topical antibiotics (including, but not limited to erythromycin or bacitracin ointments), oral tetracyclines (tetracycline, doxycycline, or minocycline), anti-inflammatory compounds (including, but not limited to, cyclosporine) and corticosteroids.

B. VEGFR-2 Inhibitor Product(s)

In one embodiment, methods described herein optionally comprise administering a VEGFR-2 inhibitor product to the subject. In some embodiments, the VEGFR-2 inhibitor product and the anti-lymphangiogensis agent are co-administered in a single composition. In other embodiments, the VEGFR-2 inhibitor product is administered as a separate composition from the anti-lymphangiogenesis agent. cDNA and amino acid sequences of human VEGFR-2 are set forth in SEQ ID NOs: 50 and 51, respectively. The "VEGFR-2 inhibitor product" can be any molecule that acts with specificity to reduce VEGF-C/VEGFR-2, VEGF-D/VEGFR-2 or VEGF/VEGFR-2 interactions, e.g., by blocking VEGF-C or VEGF-D binding to VEGFR-2, by blocking VEGF binding to VEGFR-2 or by reducing expression of VEGFR-2. In one embodiment, the VEGFR-2 inhibitor inhibits VEGF-C and VEGF-D binding to VEGFR-2. In another embodiment, the VEGFR-2 inhibitor inhibits binding of VEGF to VEGFR-2. The VEGFR-2 inhibitor can be a polypeptide comprising a soluble VEGFR-2 extracellular domain fragment (amino acids 20-764 of SEQ ID NO: 51) that binds VEGF or VEGF-C or VEGF-D; VEGFR-2 antisense polynucleotides or short-interfering RNA (siRNA); anti-VEGFR-2 antibodies; a VEGFR-2 inhibitor polypeptide comprising an antigen-binding fragment of an anti-VEGFR-2 antibody that inhibits binding between VEGFR-2 and VEGF or VEGF-C or VEGF-D; an aptamer that inhibits binding between VEGFR-2 and VEGF; an aptamer that inhibits binding between VEGFR-2 and VEGF-C; an aptamer that inhibits binding between VEGFR-2 and VEGF-D; or a fusion protein comprising the soluble VEGFR-2 polypeptide fragment fused to an immunoglobulin constant region fragment (Fc). In some embodiments, a VEGFR-2 polypeptide fragment is fused to alkaline phosphatase (AP). Methods for making Fc or AP fusion constructs are found in WO 02/060950, the disclosure of which is incorporated herein by reference in its entirety.

A number of VEGFR-2 antibodies have been described, see for example, U.S. Pat. No. 6,334,339 and U.S. Patent Publication Nos. 2002/0064528, 2005/0214860, and 2005/0234225 (all of which are incorporated herein by reference in their entireties). Antibodies are useful for modulating VEGFR-2/VEGF interactions due to the ability to easily generate antibodies with relative specificity, and due to the continued improvements in technologies for adopting antibodies to human therapy. Thus, the invention contemplates use of antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for VEGFR-2. Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86 95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779 783 (1992); Lonberg et al., Nature 368 856 859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13:65-93 (1995).

VEGFR-2 antibody fragments, including Fab, Fab', F(ab') 2, Fv, scFv, are also contemplated. The term "specific for," when used to describe antibodies of the invention, indicates that the variable regions of the antibodies of the invention recognize and bind the polypeptide of interest exclusively (i.e., able to distinguish the polypeptides of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies of the invention can be produced using any method well known and routinely practiced in the art.

In another embodiment, methods described herein optionally comprise administering an anti-sense VEGFR-2 nucleic acid molecule to the subject. Anti-sense VEGFR-2 nucleic acid molecules are useful therapeutically to inhibit the translation of VEGFR-2-encoding mRNAs where the therapeutic objective involves a desire to eliminate the presence of VEGFR-2 or to downregulate its levels. VEGFR-2 antisense RNA, for example, could be useful as a VEGFR-2 antagonizing agent in the treatment of diseases in which VEGFR-2 is involved as a causative agent, e.g, inflammatory diseases.

An antisense nucleic acid comprises a nucleotide sequence that is complementary to a "sense" nucleic acid encoding a protein (e.g., complementary to the coding strand of a double-stranded cDNA molecule or complementary to an mRNA sequence). (See, e.g., the VEGFR-3 cDNA sequence of SEQ ID NO: 9). Methods for designing and optimizing antisense nucleotides are described in Lima et al., (*J Biol Chem;* 272:626-38. 1997) and Kurreck et al., (*Nucleic Acids Res.;* 30:1911-8. 2002). In specific aspects, antisense nucleic acid molecules are provided that comprise a sequence complementary to at least about 10, 25, 50, 100, 250 or 500 nucleotides or an entire VEGFR-2 coding strand, or to only a portion thereof. Nucleic acid molecules encoding fragments, homologs, derivatives and analogs of a VEGFR-2 or antisense nucleic acids complementary to a VEGFR-2 nucleic acid sequence are also contemplated.

In one embodiment, an antisense nucleic acid molecule is antisense to a "coding region" of the coding strand of a nucleotide sequence encoding a VEGFR-2 protein. The term "coding region" refers to the region of the nucleotide sequence comprising codons which are translated into amino acid residues. In another embodiment, the antisense nucleic acid molecule is antisense to a "conceding region" of the coding strand of a nucleotide sequence encoding the VEGFR-2. The term "conceding region" refers to 5' and 3' sequences which flank the coding region that are not translated into amino acids (i.e., also referred to as 5' and 3' untranslated regions).

Antisense nucleic acids of the invention can be designed according to the rules of Watson and Crick or Hoogsteen base pairing. The antisense nucleic acid molecule can be complementary to the entire coding region of VEGFR-2 mRNA, but more preferably is an oligonucleotide that is antisense to only a portion of the coding or noncoding region of VEGFR-2 mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation.

The antisense nucleic acid molecules of the invention are typically administered to a subject or generated in situ such that they hybridize with or bind to cellular mRNA and/or genomic DNA encoding VEGFR-2 to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix.

In still another embodiment, VEGFR-2 RNA can be used for induction of RNA interference (RNAi), using double stranded (dsRNA) (Fire et al., *Nature* 391: 806-811. 1998) or short-interfering RNA (siRNA) sequences (Yu et al., *Proc Natl Acad Sci USA.* 99:6047-52. 2002). "RNAi" is the process by which dsRNA induces homology-dependent degradation of complimentary mRNA. In one embodiment, a nucleic acid molecule of the invention is hybridized by complementary base pairing with a "sense" ribonucleic acid of the invention to form the double stranded RNA. The dsRNA antisense and sense nucleic acid molecules are provided that correspond to at least about 20, 25, 50, 100, 250 or 500 nucleotides or an entire VEGFR-2 coding strand, or to only a portion thereof. In an alternative embodiment, the siRNAs are 30 nucleotides or less in length, and more preferably 21- to 23-nucleotides, with characteristic 2- to 3-nucleotide 3'-overhanging ends, which are generated by ribonuclease III cleavage from longer dsRNAs. See e.g. Tuschl T. (*Nat Biotechnol.* 20:446-48. 2002). Preparation and use of RNAi compounds is described in U.S. Patent Publication No. 2004/0023390, the disclosure of which is incorporated herein by reference in its entirety.

Intracellular transcription of small RNA molecules can be achieved by cloning the siRNA templates into RNA polymerase III (Pol III) transcription units, which normally encode the small nuclear RNA (snRNA) U6 or the human RNAse P RNA H1. Two approaches can be used to express siRNAs: in one embodiment, sense and antisense strands constituting the siRNA duplex are transcribed by individual promoters (Lee, et al. *Nat. Biotechnol.* 20, 500-505. 2002); in an alternative embodiment, siRNAs are expressed as stem-loop hairpin RNA structures that give rise to siRNAs after intracellular processing (Brummelkamp et al. *Science* 296:550-553. 2002) (incorporated herein by reference).

The dsRNA/siRNA is most commonly administered by annealing sense and antisense RNA strands in vitro before delivery to the organism. In an alternate embodiment, RNAi may be carried out by administering sense and antisense nucleic acids of the invention in the same solution without annealing prior to administration, and may even be performed by administering the nucleic acids in separate vehicles within a very close timeframe. Nucleic acid molecules encoding fragments, homologs, derivatives and analogs of a VEGFR-2 or antisense nucleic acids complementary to a mVEGFR-2 nucleic acid sequence are also contemplated.

Aptamers are another nucleic acid based method for interfering with the interaction of VEGFR-2 or VEGFR-3 and their respective ligands VEGF-A and/or VEGF-C and/or VEGF-D. Aptamers are DNA or RNA molecules that have been selected from random pools based on their ability to bind other molecules. Aptamers have been selected which bind nucleic acid, proteins, small organic compounds, and even entire organisms. Methods and compositions for identifying and making aptamers are known to those of skill in the art and are described e.g., in U.S. Pat. No. 5,840,867 and U.S. Pat. No. 5,582,981 each incorporated herein by reference.

Recent advances in the field of combinatorial sciences have identified short polymer sequences with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the present invention, molecular evolution techniques can be used to isolate binding constructs specific for ligands described herein. For more on aptamers, See generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

In some embodiments, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and re-screened, whereby a growth factor aptamer is be identified.

In yet another variation, the VEGFR-2 inhibitor product comprises a soluble extracellular domain fragment of VEGFR-1 that binds VEGF and inhibits VEGF binding to VEGFR-2. cDNA and amino acid sequences of VEGFR-1 are set forth in SEQ ID NOs: 18 and 19. Exemplary extracellular domain fragments of VEGFR-1 are described in U.S. Patent Publication No. 2006/0030000 and International Patent Publication No. WO 2005/087808, the disclosures of which are incorporated herein by reference in their entireties.

C. Anti-Inflammatory Agents

In another embodiment, the methods described herein optionally comprise administering one or more anti-inflammatory agents to the subject. In some embodiments, the anti-inflammatory agent and the anti-lymphangiogenic agent are co-administered in a single composition. In other embodiments, the anti-inflammatory agent is administered as a separate composition from the anti-lymphangiogenic agent. Combinations involving an anti-lymphangiogenic agent, a VEGFR-2 inhibitor, and an anti-inflammatory agent are specifically contemplated. As used herein, the term "anti-inflammatory agent" refers generally to any agent that reduces inflammation or swelling in a subject. A number of exemplary anti-inflammatory agents are recited herein, but it will be appreciated that there may be additional suitable anti-inflammatory agents not specifically recited herein, but which are encompassed by the present invention.

In one variation, the anti-inflammatory agent is a non-steroidal anti-inflammatory drug (NSAID). Exemplary NSAIDs include, but are not limited to: aspirin, Sulfasalazine™, Asacol™, Dipendtum™, Pentasa™, Anaprox™, Anaprox DS™ (naproxen sodium); Ansaid™ (flurbiprofen); Arthrotec™ (diclofenac sodium+ misoprostil); Cataflam™/ Voltaren™ (diclofenac potassium); Clinoril™ (sulindac); Daypro™ (oxaprozin); Disalcid™ (salsalate); Dolobid™ (diflunisal); EC Naprosyn™ (naproxen sodium); Feldene™ (piroxicam); Indocin™, Indocin SR™ (indomethacin); Lodine™, Lodine XL™ (etodolac); Motrin™ (ibuprofen); Naprelan™ (naproxen); Naprosyn™ (naproxen); Orudis™, (ketoprofen); Oruvail™ (ketoprofen); Relafen™ (nabumetone); Tolectin™, (tolmetin sodium); Trilisate (choline magnesium trisalicylate); Cox-1 inhibitors; Cox-2 Inhibitors such as Vioxx™ (rofecoxib); Arcoxia™ (etoricoxib), Celebrex™ (celecoxib); Mobi™ (meloxicam); Bextra™ (valdecoxib), Dynastat™ paracoxib sodium; Prexige™ (lumiracoxib), and nambumetone. Additional suitable NSAIDs, include, but are not limited to, the following: 5-aminosalicyclic acid (5-ASA, mesalamine, lesalazine), ε-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770.

In another variation, the anti-inflammatory agent can be a compound that inhibits the interaction of inflammatory cytokines with their receptors. Examples of cytokine inhibitors useful in combination with the specific binding agents of the invention include, for example, antagonists (such as antibodies) of TGF-α (e.g., Remicade), as well as antagonists (such as antibodies) directed against interleukins involved in inflammation. Such interleukins are described herein and preferably include, but are not limited to, IL-1, IL-2, IL-3, IL-4, IL-5, IL-6, IL-8, IL-9, IL-12, IL-13, IL-17, and IL-18. See Feghali, et al., *Frontiers in Biosci.*, 2:12-26 (1997).

In another variation, the anti-inflammatory agent is a corticosteroid. Exemplary corticosteroids include, but are not limited to, difloroasone diacetate, clobetasol propionate, halobetasol propionate, betamethasone, betamethasone dipropionate, budesonide, cortisone, dexamethasone, fluocinonide, halcinonide desoximethasone, triamcinolone, fluticasone propionate, fluocinolone acetonide, flurandrenolide, mometasone furoate, betamethosone, fluticasone propionate, fluocinolone acetonide, aclometasome dipropionate, methylprednisolone, prednisolone, prednisone, triamicinolone, desonide and hydrocortisone.

In another variation, the anti-inflammatory agent is cyclosporine.

D. Antibiotics

In another embodiment, the methods described herein optionally further comprise administering an antibiotic to the subject. In some embodiments, the antibiotic and the anti-lymphangiogenic agent are co-administered in a single composition. In other embodiments, the antibiotic is administered as a separate composition from the anti-lymphangiogenic agent. Exemplary antibiotics include, but are not limited to, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, and imidazole carboxamide.

D. Tyrosine Kinase Inhibitors

In another embodiment, the methods described herein optionally further comprise administering a tyrosine kinase inhibitor that inhibits VEGFR-2 and/or VEGFR-3 activity. It is contemplated that VEGFR-3 tyrosine kinase inhibitors would be useful in combination therapy embodiments where the anti-lymphangiogenic agent is not a VEGFR-3 tyrosine kinase inhibitor.

Exemplary tyrosine kinase inhibitors for use in the methods described herein include, but are not limited to, AEE788 (TKI, VEGFR-2, EGFR: Novartis); ZD6474 (TKI, VEGFR-1, -2, -3, EGFR: Zactima: AstraZeneca); AZD2171 (TKI, VEGFR-1, -2: AstraZeneca); SU 11248 (TKI, VEGFR-1, -2, PDGFR: Sunitinib: Pfizer); AG13925 (TKI, VEGFR-1, -2: Pfizer); AG013736 (TKI, VEGFR-1, -2: Pfizer); CEP-7055 (TKI, VEGFR-1, -2, -3: Cephalon); CP-547,632 (TKI, VEGFR-1, -2: Pfizer); GW7S6024 (TKL VEGFR-1, -2, -3: GlaxoSmithKline); GW786034 (TKI, VEGFR-1, -2, -3: GlaxoSmithKline); sorafenib (TKI, Bay 43-9006, VEGFR-1, -2, PDGFR: Bayer/Onyx); SU4312 (TKI, VEGFR-2, PDGFR: Pfizer); AMG706 (TKI, VEGFR-1, -2, -3: Amgen); XL647 (TKI, EGFR, HER2, VEGFR, ErbB4: Exelixis); XL999 (TK1, FGFR, VEGFR, PDGFR, F11-3: Exelixis); PKC412 (TKI, KIT, PDGFR, PKC, FLT3, VEGFR-2: Novartis); AEE788 (TKI, EGFR, VEGFR2, VEGFR-1: Novartis): OSI-030 (TKI, c-kil, VEGFR: OSI Pharmaceuticals); OS 1-817 (TKI c-kit, VEGFR: OSI Pharmaceuticals); DMPQ (TKI, ERGF, PDGFR, ErbB2. p56. pkA, pkC); MLN518 (TKI, F1t3, PDGFR, c-KIT (T53518: Millennium Pharmaceuticals); lestaurinib (TKI, FLT3, CEP-701, Cephalon); ZD 1839 (TKI, EGFR: gefitinib, Iressa: AstraZcneca); OSI-774 (TKI, EGFR: Erlotininb: Tarceva: OSI Pharmaceuticals); lapatinib (TKI, ErbB-2, EGFR, and GD-2016: Tykerb: GlaxoSmithKline).

In some embodiments, the methods described herein further comprise administering a tyrosine kinase inhibitor that inhibits angiogenesis to the subject. Exemplary anti-angiogeneic tyrosine kinase inhibits and their targets are provided below in Table 2.

TABLE 2

| Antiangiogenic tyrosine kinase receptor inhibitors and their targets | | | | | | |
|---|---|---|---|---|---|---|
| Agent | VEGFR-1 | VEGFR-2 | VEGFR-3 | PDGFR | EGFR | Other targets |
| Vandetanib |  | ● |  |  | ● | RET |
| Sunitinib | ● | ● | ● | ● |  | KIT, FLT3, RET |
| Axitinib | ● | ● | ● |  |  |  |
| Sorafenib | ● | ● | ● | ● |  | KIT, RAF, FLT3 |
| Vatalanib | ● | ● | ● | ● |  | KIT |
| Cediranib | ● | ● | ● | ● |  | KIT |

TABLE 2-continued

Antiangiogenic tyrosine kinase receptor inhibitors and their targets

| Agent | VEGFR-1 | VEGFR-2 | VEGFR-3 | PDGFR | EGFR | Other targets |
|---|---|---|---|---|---|---|
| Motesanib | ● | ● | ● | ● | | KIT, RET |
| Pazopanib | ● | ● | ● | ● | | KIT |
| BIBF 1120 | | ● | | ● | | FGFR |

Abbreviations:
FGFR, fibroblast-like growth factor receptor;
FLT3, FMS-like tyrosine kinase 3;
KIT, stem cell factor receptor;
RET, glial cell line-derived neurotrophic factor receptor;
VEGFR, vascular endothelial growth factor receptor.

E. Administration of the Combination Therapy

Combination therapy with one or more of the additional agents described herein may be achieved by administering to a subject a single composition or pharmacological formulation that includes the anti-lymphangiogenic agent and the one or more additional agents, or by administering to the subject two (or more) distinct compositions or formulations, at the same time, wherein one composition includes an anti-lymphangiogenic agent and the other includes a second agent.

Alternatively, the combination therapy employing an anti-lymphangiogenic agent described herein may precede or follow the second agent treatment by intervals ranging from minutes to weeks. In embodiments where the second agent and the anti-lymphangiogenic agent are administered separately, one would generally ensure that a significant period of time did not expire between the times of each delivery, such that the agent and the anti-lymphangiogenic agent would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated.

Formulations and Pharmaceutically Acceptable Carriers

Some exemplary ophthalmic viscosity enhancers that can be used in the present formulation include: carboxymethyl cellulose sodium; methylcellulose; hydroxypropyl cellulose; hydroxypropylmethyl cellulose; hydroxyethyl cellulose; polyethylene glycol 300; polyethylene glycol 400; polyvinyl alcohol; and providone.

Some natural products, such as veegum, alginates, xanthan gum, gelatin, acacia and tragacanth, may also be used to increase the viscosity of ophthalmic solutions.

A tonicity is important because hypotonic eye drops cause an edema of the cornea, and hypertonic eye drops cause deformation of the cornea. The ideal tonicity is approximately 300 mOsM. The tonicity can be achieved by methods described in Remington: The Science and Practice of Pharmacy, known to those versed in the art.

Suitable ophthalmic carriers are known to those skilled in the art and all such conventional carriers may be employed in the present invention. Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylannmonium bromide, polaxamers, spans, tweens, bile salts and lecithin), terpene (d-limonene, alphaterpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chiorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris.

In some embodiments, penetration enhancers are added to the ophthalmologic carrier.

Routes of Administration

The composition containing the anti-lymphangiogenic agent can be administered to a patient by a variety of means depending, in part, on the type of agent to be administered and the history, risk factors and symptoms of the patient. Routes of administration suitable for the methods of the invention include both systemic and local administration. Thus, in one embodiment, a method of treating dry eye disease is practiced by systemic administration of a pharmaceutical composition comprising the anti-lymphangiogenic agent. In another embodiment, a method of the invention is practiced by local administration of a pharmaceutical composition comprising the anti-lymphangiogenic agent. In further embodiments, a pharmaceutical composition comprising the anti-lymphangiogenic agent is administered topically, or by local injection, or is released from an intraocular or periocular implant.

As used herein, the term "systemic administration" means a mode of administration resulting in delivery of a pharmaceutical composition to essentially the whole body of the patient. Exemplary modes of systemic administration include, without limitation, intravenous injection and oral administration. The term "local administration," as used herein, means a mode of administration resulting in significantly more pharmaceutical composition being delivered to and about the eyes than to regions distal from the eyes.

Systemic and local routes of administration useful in the methods of the invention encompass, without limitation, oral gavage; intravenous injection; intraperitoneal injection; intramuscular injection; subcutaneous injection; transdermal diffusion and electrophoresis; topical eye drops and ointments; periocular and intraocular injection including subconjunctival injection; extended release delivery devices including locally implanted extended release devices; and intraocular and periocular implants including bioerodible and reservoir-based implants.

In some embodiments, an ophthalmic composition containing an anti-lymphangiogenic agent is administered topically to the eye. The ophthalmic composition can be for example, an ophthalmic solution (ocular drops). In other embodiments, the ophthalmic composition containing the anti-lymphangiogenic agent is injected directly into the eye. In a further embodiment, the ophthalmic composition containing the anti-lymphangiogenic agent is released from an intraocular or periocular implant such as a bioerodible or reservoir-based implant.

In some embodiments, the ophthalmic composition comprising an anti-lymphangiogenic agent is administered locally in an extended release formulation. For example, an ophthalmic composition containing an anti-lymphangiogenic agent can be administered via an intraocular or periocular implant, which can be, for example, bioerodible or reservoir-based. As used herein, the term "implant" refers to any material that does not significantly migrate from the insertion site following implantation. An implant can be biodegradable, non-biodegradable, or composed of both biodegradable and non-biodegradable materials; a non-biodegradable implant can include, if desired, a refillable reservoir. Implants useful in the methods of the invention include, for example, patches, particles, sheets, plaques, microcapsules and the like, and can be of any shape and size compatible with the selected site of insertion, which can be, without limitation, the posterior chamber, anterior chamber, suprachoroid or subconjunctiva. It is understood that an implant useful in the invention generally releases the implanted pharmaceutical composition at an effective dosage to the eye of the patient over an extended period of time. A variety of ocular implants and extended release formulations suitable for ocular release are well known in the art, as described, for example, in U.S. Pat. Nos. 5,869,079 and 5,443,505.

In instances where the anti-lymphangiogenic agent is a nucleic acid molecule, administration of a pharmaceutical composition containing the nucleic acid molecule can be carried out using one of numerous methods well known in the art of gene therapy. Such methods include, but are not limited to, lentiviral transformation, adenoviral transformation, cytomegaloviral transformation, microinjection and electroporation.

In some embodiments, the anti-lymphangiogenic agents are administered to the subject in a liquid or gel suspension in the form of drops, spray or gel. In yet another embodiment, the anti-lymphangiogenic agents are injected directly into the lacrimal tissues or onto the eye surface.

In other embodiments, the anti-lymphangiogenic agents are applied to the eye via liposomes. In still other embodiments, the anti-lymphangiogenic agents are infused into the tear film via a pump-catheter system. In still another embodiment, the anti-lymphangiogenic agents are contained within a continuous or selective-release device, for example, membranes such as, but not limited to, those employed in the Ocusert™ System (Alza Corp., Palo Alto, Calif.). As an additional embodiment, the anti-lymphangiogenic agents are contained within, carried by, or attached to contact lenses which are placed on the eye. In yet another embodiment, the anti-lymphangiogenic agents are contained within a swab or sponge which can be applied to the ocular surface. Another embodiment of the present invention involves the active compound contained within a liquid spray which can be applied to the ocular surface.

All publications and patents mentioned herein are hereby incorporated by reference in their entirety as if each individual publication or patent was specifically and individually indicated to be incorporated by reference. In case of conflict, the present application, including any definitions herein, will control.

EXAMPLES

Materials and Methods

Experimental Dry Eye Murine Model

Eight to ten week-old female C57BLI6 mice (Charles River Laboratory, Wilmington, Mass.) were used in accordance with the standards in the ARVO Statement for the Use of Animals in Ophthalmic and Vision Research. The research protocol was approved by the Schepens Eye Research Institute Animal Care and Use Committee. Dry eye was induced in murine eyes using a Controlled Environment Chamber (CEC) which exposes the mice to high-flow desiccated air. To achieve maximum ocular surface dryness, the conditions in CEC were supplemented with topical application of 1% atropine sulfate (Falcon Pharma, Fort Worth, Tex.) twice for the first 48 hours and subcutaneous injections of 0.1 ml of 5 mg/ml of scopolamine hydrobromide (Sigma-Aldrich, St. Louis, Mo.) three times a day, for the entire duration of the experiment.

RNA Isolation and Molecular Analysis Using Real Time Polymerase Chain Reaction

Five mice (10 eyes) were included in each group. Two corneas were pooled together to equal as one sample and stored at −80'C in Trizol (Invitrogen, Carlsbad, Calif.; catalog No. 15596026) until future use. Total RNA was isolated from these corneas using the RNeasy microkit (Qiagen, Valencia, Calif.; catalog No. 74004). Equal amounts of RNA were used to synthesize cDNA using SuperScript™ III Reverse Tranciptase (Invitrogen, Carlsbad, Calif.; catalog No. 18080) according to the manufacturer's recommendations. Real-Time PCR was performed using FAM-MGB dye labeled predesigned primers (Applied Biosystem, Foster City, Calif.) for GAPDH (assay ID.Mm999999 15_g1), VEGF-A (Mm00437304_m1), VEGF-C (Mrn00437313_m1), VEGF-D (Mm00438965_m1), VEGFR-2 (Mm00440099_m1), VEGFR-3 (Mm00433337_m1). 2.5 µl of cDNA was loaded in each well and assays were performed in duplicate. The GAPDH gene was used as the endogenous reference for each reaction. The results were normalized by the cycle threshold (CT) of GAPDH and the relative mRNA level in the normal mice was used as the normalized control.

Immunohistochemistry

The following primary antibodies were used for immunohistochemical staining: rat anti-mouse CD11b-FITC for monocytes/macrophages (BD Pharmingen, San Diego, Calif., 1:100), goat anti-mouse CD31 FITC as pan-endothelial marker (Santa Cruz Biotechnology, Santa Cruz, Calif., 1:100) and purified rabbit anti-mouse LYVE-1 as iymphatic endothelial marker (Abeam, Mass., USA, 1:400). Respective isotypes were used as negative controls. Rhodamine conjugated goat anti-rabbit (BD Pharmingen, San Diego, Calif., 1:100) was the secondary antibody used.

Freshly excised corneas were washed in PBS, fixed in acetone for 15 minutes and then double stained with CD31 and LYVE-1 as described previously. To analyze infiltration of CD11b$^+$/LYVE-1 cells, corneas from three mice from each group were taken and cells were counted in 5-6 areas in the periphery (0.5 µm area from the limbus) of each cornea in a masked fashion, using epifluorescence microscope (model E800; Nikon, Melville, N.Y.) at 40× magnification. The mean number of cells was obtained by averaging the total number of cells in all the areas studied and the result was expressed as the number of positive cells per mm$^2$.

Morphometry of Lymphangiogenesis in the Cornea

Morphology of lymphatics was analyzed using an automated image analysis program written with Matlab (The Mathworks, Inc., Natick, Mass.). Lymphatics were isolated from digitized images with this program using standard computer vision techniques for image segmentation, including background isolation and subtraction, edge detection, and k-means clustering. This segmentation process generated binary images in which lymphatic vessels are represented by is and all other image content is represented by Os. The resultant isolated lymphatic vessels were analyzed morphologically using two metrices, Lymphatic Area (LA) and Lymphatic Caliber (LC). LA represents the total surface area of the lymphatic vessels when projected into the plane of the image. LC is a summary measure of the diameters of the lymphatic vessels present. LC was measured using a computational technique that generates the largest diameter circle centered at each pixel inside a lymphatic vessel. The mean value across all pixels within lymphatic vessels was taken as an estimate of the mean LC for a given image.

Flow Cytometry

Draining LNs from DED (day 10) and normal mice were collected. Single cell suspension of LN cells was stained with the anti-CDI 1b-FITC and anti-lab (MHC-II)-PE. Stained LN cells were then analyzed on an EPICS XL flow cytometer (Beckman Coulter). All the antibodies with their matched isotype controls were purchased from eBioscience.

Studies involving inhibition of corneal neo-lymphangiogenesis using an anti-VEGF-C antibody (Example 5 onwards)

Anti-VEGF-C antibodies (VGX-100; Vegenics Limited, Australia) were administered intraperitonealy daily from day 1 to day 10 to DED mice. Mice were assessed clinically using corneal fluorescent staining. Tissues from cornea, conjunctiva and draining lymph nodes were examined for cellular and molecular pathological changes. In vivo blockade of VEGF-C suppresses corneallymphangiogenesis and ameliorates clinical signs of DED.

Statistical Analysis

A two-tailed Student's t-test was performed and P-values less than 0.05 were deemed statistically significant. Results are presented as the mean±SEM of at least three experiments.

Example 1: Demonstration and Quantification of Lymphatics in Dry Eye Corneas

Figure 2:
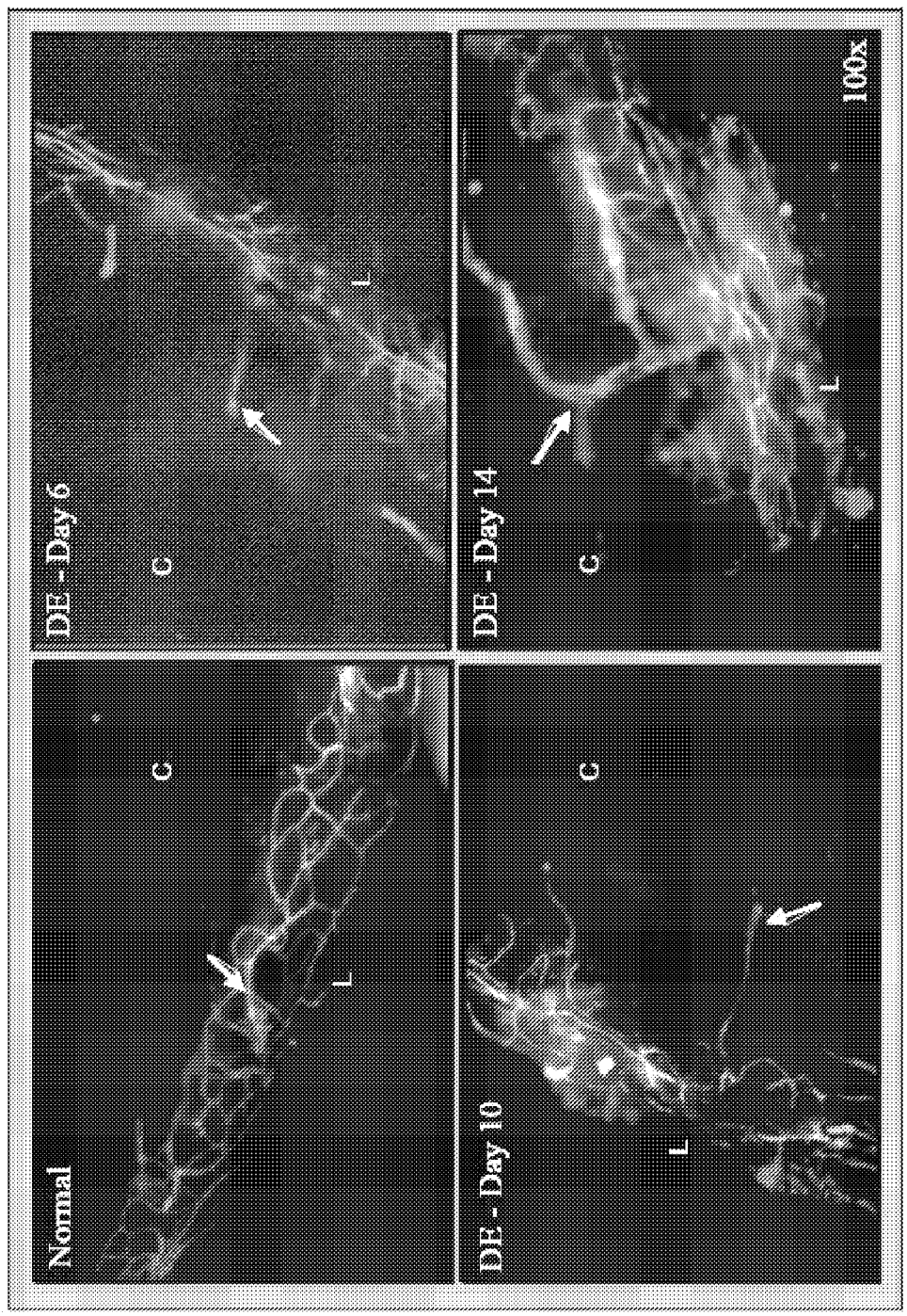
FIG. 2: Representative whole mount corneal immunofluorescence micrographs showing lymphatics (CD31$^{lo}$/LYVE-1$^{hi}$) in normal and dry eye (DE) at days 6, 10 and 14 (100× magnification).
Figure 3A:
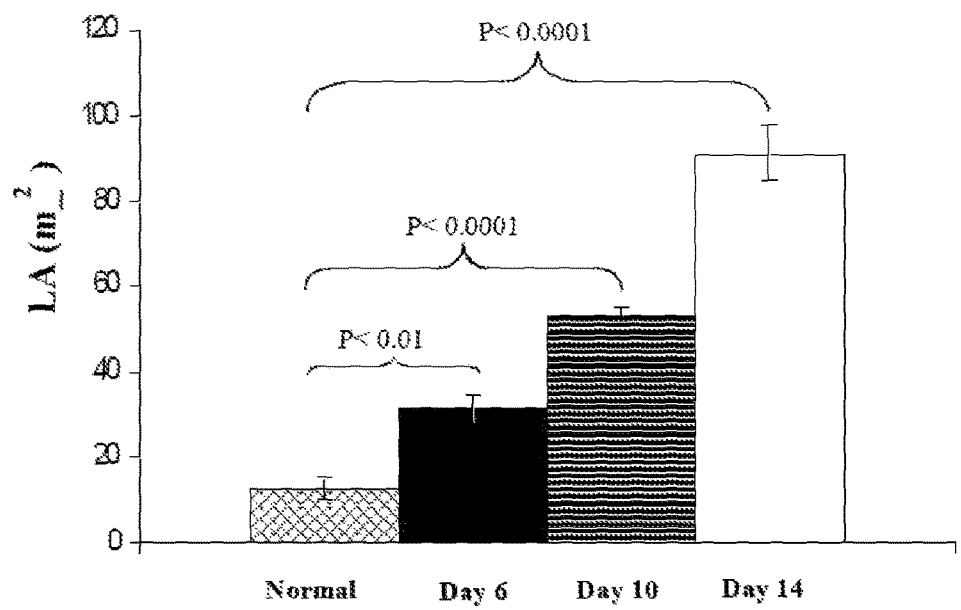
FIG. 3a and FIG. 3b: Quantification of lymphatics in dry eye (DE) corneas. Morphometric analysis of corneal lymphangiogenesis in normal and DE days 6, 10 and 14 (100× magnification). Morphometric evaluation showed significant increase in lymphatic area (LA) in dry eye compared to normal corneas (FIG. 3a). Significant increase in lymphatic caliber (LC) in dry eye compared to normal corneas was noticed only at day 14 (FIG. 3b). Data from a representative experiment of three performed is shown as mean±S.E.M and each group consists of four to five mice.
Figure 3B:
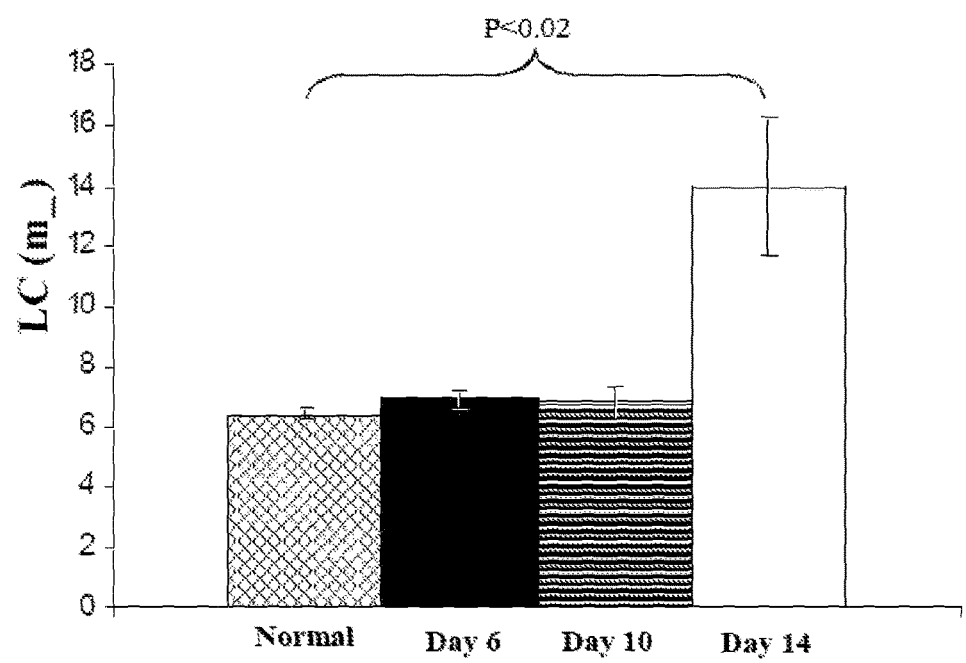

To determine whether DED induces growth of lymphatics into the cornea, and whether lymphatic growth is paralleled by growth of blood vessels, corneal whole mounts were double stained for CD31 (pan-endothelial marker) and LYVE-1 (lymphatic vascular endothelial marker) at days 0, 6, 10 and 14 and quantified for lymphangiogenesis. Blood vessels were identified as CD31$^{hi}$/LyvE-1$^-$ and lymph vessels were identified as CD31$^{lo}$/LYVE-1$^{hi}$. A significant increase in lymphatic area LA is seen in DED mice (FIG. 1b). Morphometric analysis revealed small buds of lymphatic vessels arising from the limbal vascular arcade at an early time point (day 6), which increased in caliber (LC) and area (LA), and advanced towards the center of the cornea with DED progression (FIGS. 1 and 2). A significant increase in LA (FIG. 3a) was seen as early as day 6 (P<0.01) which continued until day 14 (P<0.0001). However, LC (FIG. 3b) was significantly increased from the normal only by day 14 (P<0.02). Remarkably, these lymphatics were not accompanied by growth of blood vessels at any given time point.

Example 2: Expression Levels of Different VEGF's and VEGFR's in Dry Eye Corneas

Figure 4:
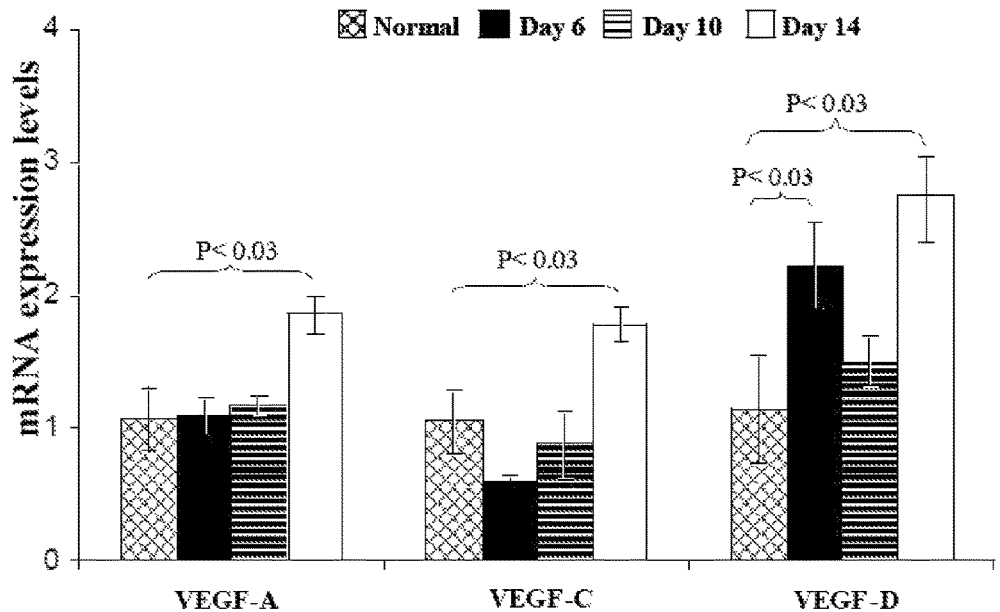
FIG. 4: Analysis of lymphangiogenic-specific growth factors. Real-time PCR analysis showing transcript levels of VEGF-A, VEGF-C and VEGF-D in the dry eye corneas at different time points. A significant increase in VEGF-D was seen at day 6 whereas VEGF-A and VEGF-C increased significantly only by day 14. Data from a representative experiment of three performed is shown as mean±S.E.M and each group consists of four to five mice.
Figure 5:
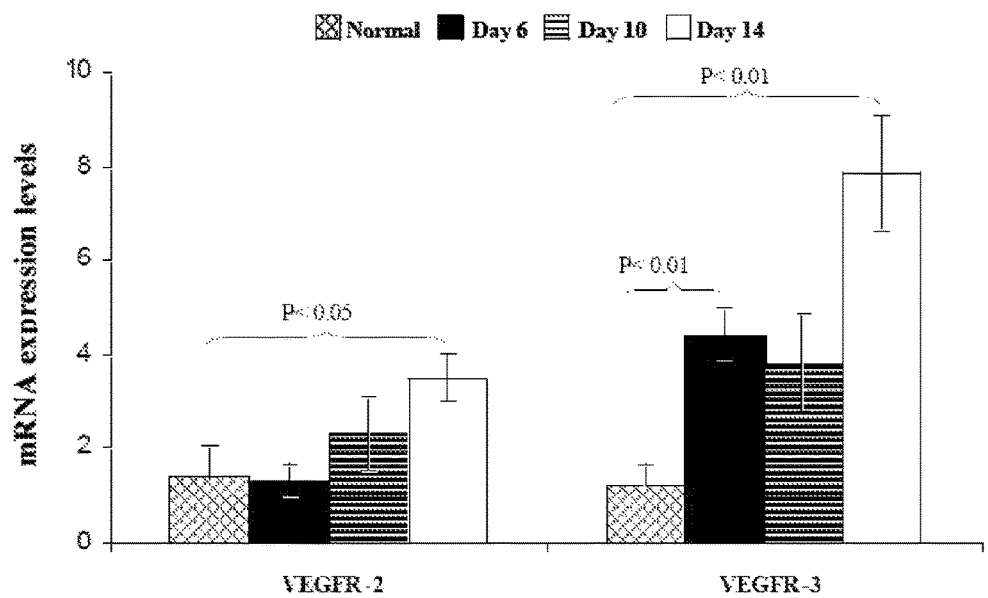
FIG. 5: Analysis of lymphangiogenic-specific growth factor receptors. Real-time PCR analysis showing transcript levels of VEGFR-2 and VEGFR-3 in the dry eye corneas at different time points. Significant increase in VEGFR-3 was seen earliest at day 6 but VEGFR-2 increased significantly later in disease at day 14. Data from a representative experiment of three performed is shown as mean±S.E.M and each group consists of four to five mice.

The development of lymphatic vessels is regulated by factors common to both hemangiogenesis and lymphangiogenesis. VEGF-C and VEGF-D are the classic lymphangiogenic factors and act by binding to their receptors VEGFR-2 and VEGFR-3, which are expressed on lymphatic endothelial cells. To determine the molecular mechanisms of lymphangiogenesis in DED, expression of different vascular endothelial growth factors and their receptors were quantified at indicated time points in the cornea using real time PCR. Amongst the VEGF species (FIG. 4), lymphangiogenic specific VEGF-D was not only the earliest to increase at day 6 (−2 folds; P<0.03) but also showed the maximum increase in expression at day 14 (−3 folds; P<0.03). Significant increased transcript expression of VEGF-A and VEGF-C was seen only by day 14 (P<0.03 for both). Similarly levels of lymphangiogenic specific VEGFR-3 were first to show a significant increase at day 6 (−4 folds; P<0.01) and continued to rise until day 14 (−8 folds; P<0.01). Though an overall trend toward increased expression was noticed with VEGFR-2 (primarily specific for blood vessel growth), significant increase (P<0.05) was appreciated only by day 14 (FIG. 5).

Example 3: Enumeration of CD11b/LYVE-1 Positive Cells in Dry Eye Corneas

Figure 6:
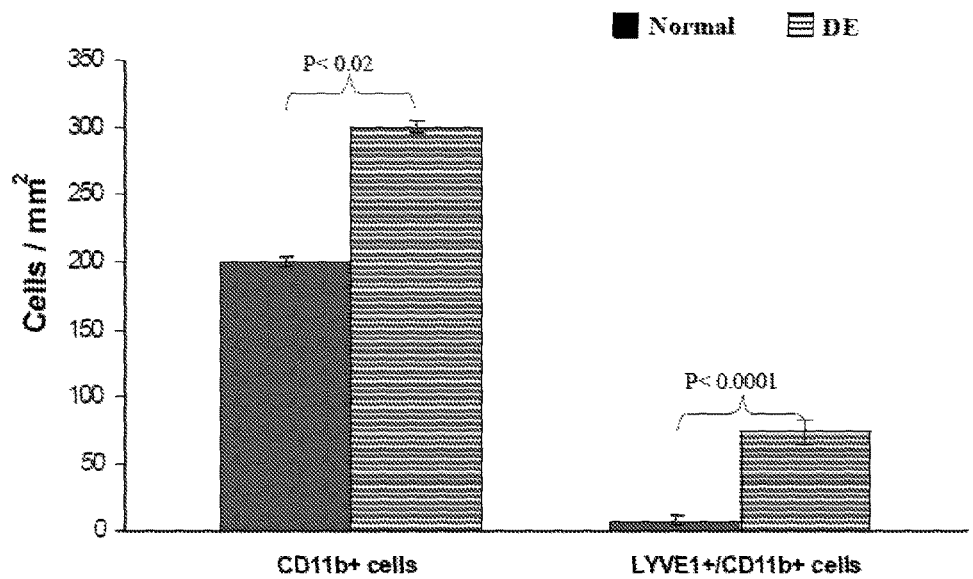
FIG. 6: Enumeration of corneal CD11b$^+$/LYVE-1$^+$ cells. A significant increase in the number of both CD11b$^+$ and double stained CD11$^{hi}$/LYVE-1$^+$ cells in the dry eye corneas as compared to normal. Data from a representative experiment of three performed is shown as mean±S.E.M and each group consists of four to five mice.

The normal cornea has a resident population of bone marrow-derived CD11b$^+$ monocyticmacrophage-lineage cells and the development of DED increases the number of CD11b$^+$ cells in the cornea. The role of macrophages in inflammatory lymphangiogenesis is well established. These CD11b$^+$ macrophages may also express various lymphatic endothelial markers, such as LYVE-1. To see what proportion of these CD11b+ cells had lymphangiogenic potential, whole mount corneal tissues were double stained with CD11b and LYVE-1 at day 14. There was a significant increase in the number of both CD11b+(P<0.02) and CD11b+/LYVE-1+ (P<0.0001) cells in dry eye as compared to normal corneas (FIG. 6). In DED, about 25% of the CD11b+ cells were positive for LYVE-1 where as only 4% of the CD11b+ cells were positive for LYVE-1 in the normal corneas.

Example 4: Role of APC Homing

Figure 7:
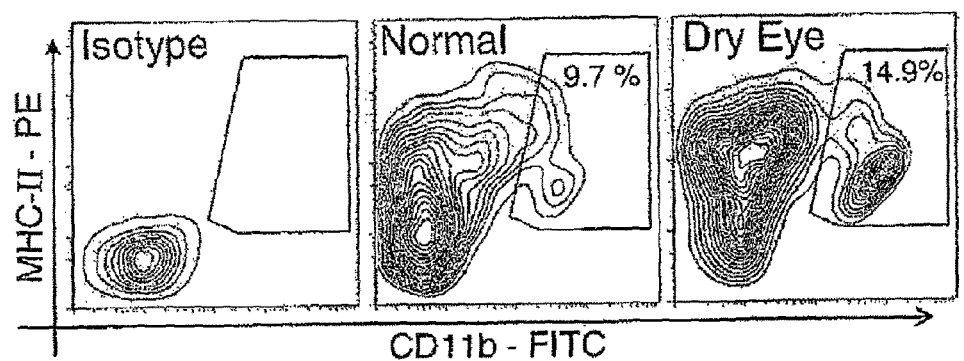
FIG. 7: Increased homing of mature MTIC-II+CD11b+ APC in the draining LN of DED mice. Flow cytometric analysis of draining lymph nodes showing significant increase in the frequencies of mature MHC-II$^+$ CD11b$^+$ APC in DED mice compared with normal mice. Data from a representative experiment of two performed is shown and each group consists of three mice.

It was next investigated whether corneal lymphangiogenesis in DED is associated with the increased homing of APC in the draining LN. Using flow cytometry, the frequencies of mature APC (MHC-II+CD11b+) in the draining LN of normal and DED mice were analysed (FIG. 7). Data showed a significant increase in the frequency of MHC-II+CD11b+ APC in the LN cells of DED mice compared to those in the LN of normal mice (Range: 14.9-19.5% vs. 10-13.5%, p<0.05).

Example 5: Effect of In Vivo Blockade of Pro-Lymphangiogenesic VEGF-C on Dry Eye Disease Dry eye was induced in murine eyes as described in the materials and methods.

Figure 8:
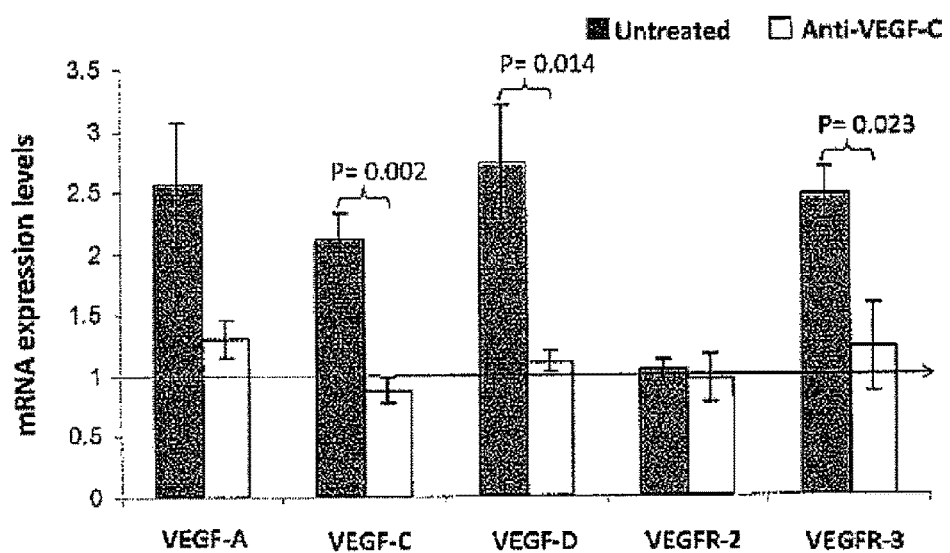
FIG. 8: Analysis of lymphangiogenic-specific growth factors and their receptors. Real-time PCR analysis showing transcript levels of VEGF-A, VEGF-C, VEGF-D, VEGFR-2 and VEGFR-3 in the dry eye corneas.
Figure 9:
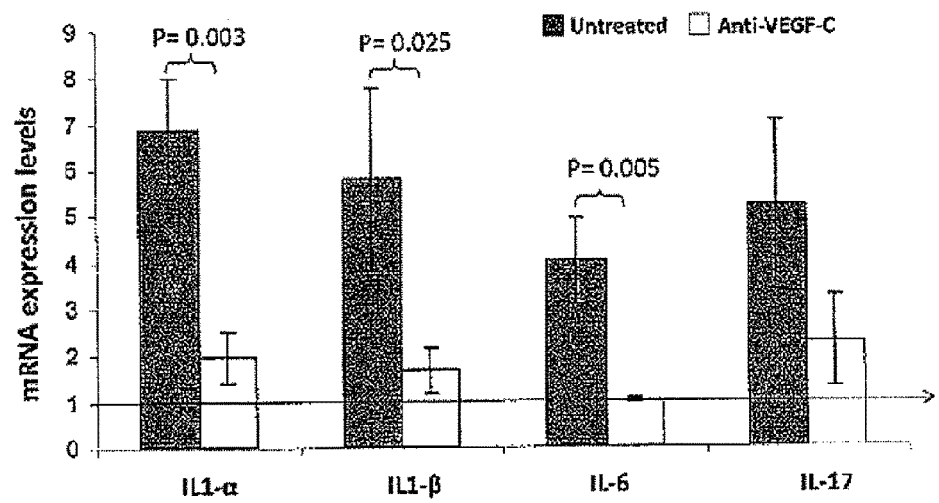
FIG. 9: Analysis of proinflammatory cytokines in conjunctiva. Real-time PCR analysis showing expression of cytokines IL-1α, IL-1β, IL-6, IL-17. The levels of all four cytokines in the conjunctiva showed significantly decreased expression in anti-VEGF-C treated DED mice as compared to those of untreated DED mice
Figure 10:
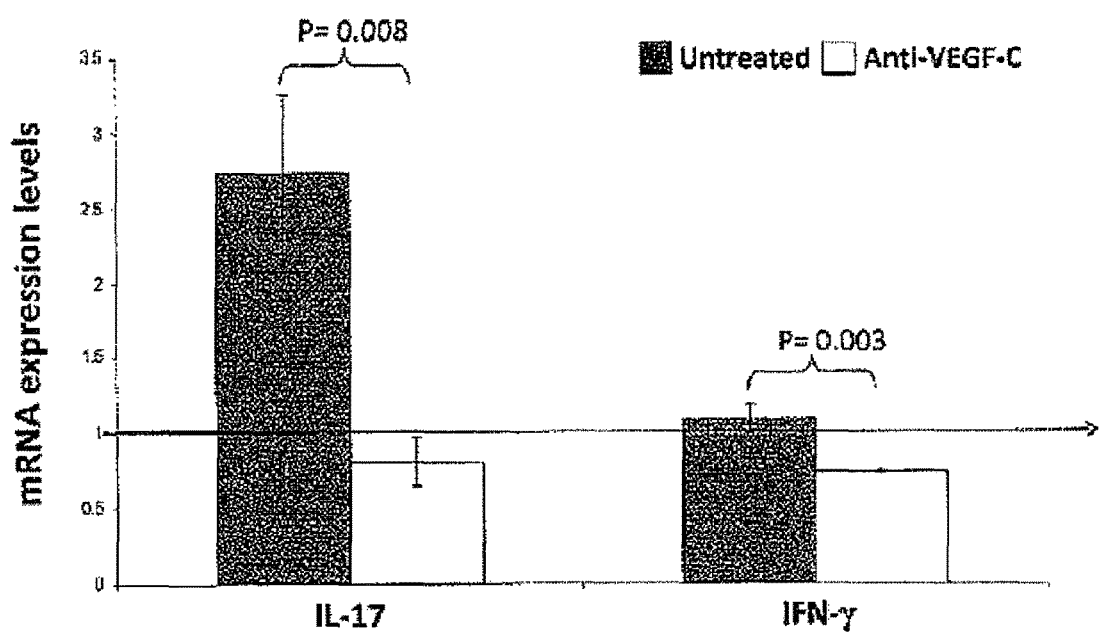
FIG. 10: Analysis of inflammatory cytokines in draining lymph nodes. Real-time PCR analysis for IL-17 (Th17 cells) and IFN-γ (Th1 cells). Draining lymph nodes of anti-VEGF-C treated DED mice showed significantly decreased induction of T-cell mediated autoimmune response compared untreated DED mice.

Real time PCR was performed to quantify expression of different VEGF growth factors (VEGF-A, VEGF-C, VEGF-D) and their receptors (VEGFR-2, VEGFR-3) in the cornea at days 6, 10 and 14 (FIG. 8) and to determine the levels of proinflammatory cytokines. IL-1α, IL-1β, IL-6, IL-17 in the conjunctiva showed significantly decreased expression in anti-VEGF-C treated DED mice as compared to those of untreated DED mice (FIG. 9). Draining lymph nodes of anti-VEGF-C treated DED mice showed significantly decreased induction of T-cell mediated autoimmune response compared untreated DED mice as determined by Real-time PCR analysis for IL-17 (Th17 cells) and IFN-γ (Th1 cells) (FIG. 10).

Figure 11:
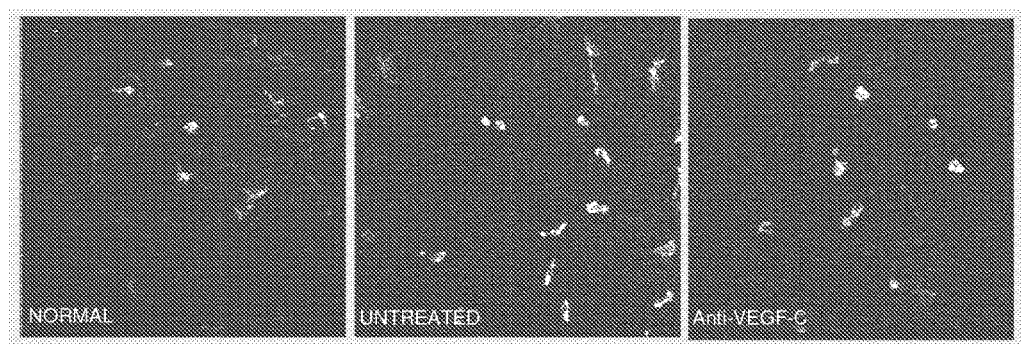
FIG. 11: Enumeration of CD11b$^+$ cells in DED corneas. Treatment with anti-VEGF-C antibodies significantly decreased infiltration of CD11b$^+$ cells (30%) in the DED corneas (day 14).
Figure 11:
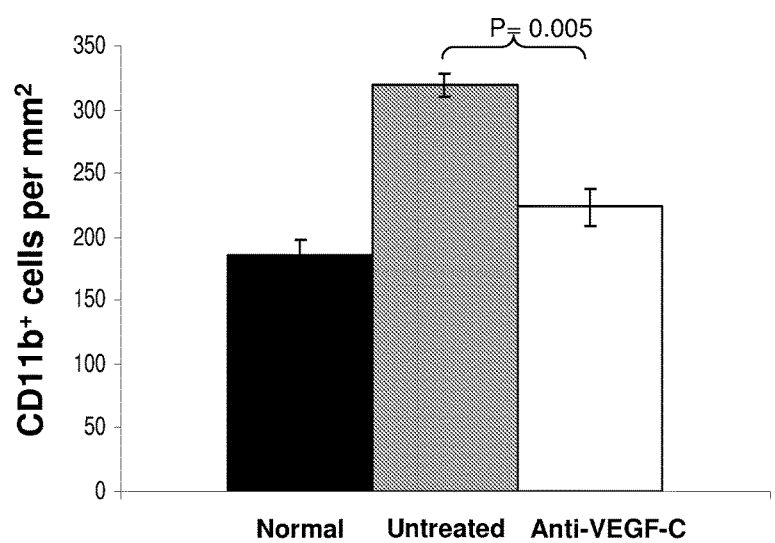

Enumeration of CD11b+/LYVE-1+ monocytic cells was done in the DED corneas at day 14 as described previously (FIG. 11). Treatment with anti-VEGF-C antibodies significantly decreased infiltration of CD11b+ cells (30%) in the DED corneas.

Figure 12:
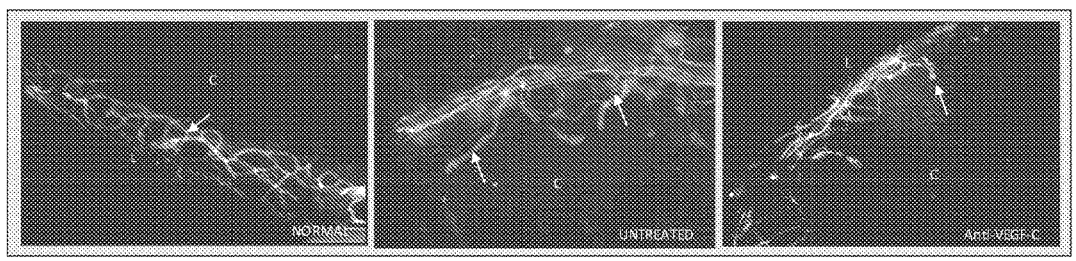
FIG. 12: Epifluorescent microscopic image of corneal wholemounts immunostained with CD31 and LYVE-1.
Figure 13:
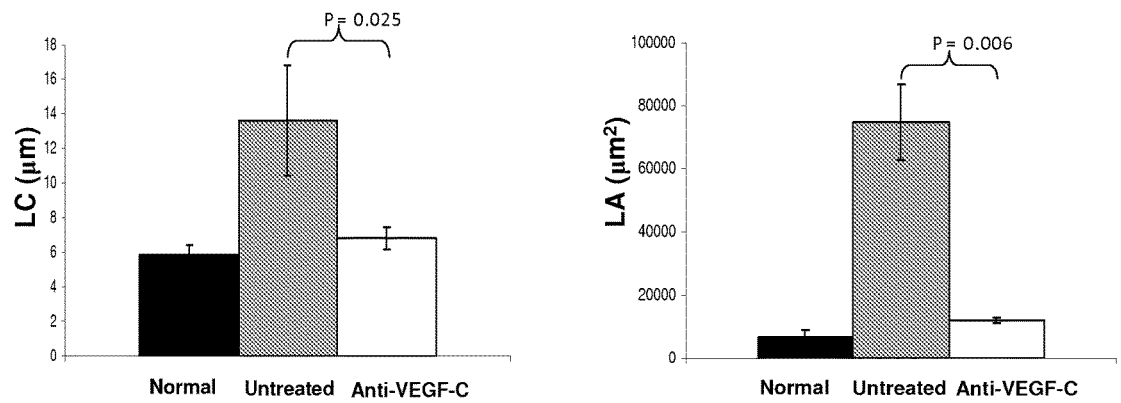
FIG. 13: Quantification of number of infiltrating CD11b+ cells per mm$^2$ of cornea.

To determine whether DED induces growth of lymphatics into the cornea, and whether lymphatic growth is paralleled by growth of blood vessels, corneal whole mounts were double stained for CD31 (pan-endothelial marker) and LYVE-1 (lymphatic vascular endothelial marker) at days 0, 6, 10 and 14 and quantified for lymphangiogenesis as described previously. Lymphatics were seen growing toward the center of DED corneas (FIG. 12). Morphometric analysis showed significant increase in both lymphatic area (P<0.0001) and lymphatic caliber (P<0.02) at day 14 of disease (FIG. 13). These lymphatics were not accompanied by any new blood vessels. Lymphangiogenic specific VEGF-D and VEGFR-3 were the earliest to increase at day 6 followed by increase in VEGF-C, VEGF-A and VEGFR-2. Increased recruitment of CD11b+/LYVE-1+ monocytic cells to the cornea was also seen with disease.

These results demonstrate that low-grade inflammation associated with dry eye is an inducer of lymphangiogenesis without accompanied hemangiogenesis.

Clinical Relevance: Demonstration of selective lymphatic growth into dry eye corneas provides an important mechanistic link to adaptive (T cell-meditated) immunity by delineating how corneal antigen trafficking can occur to the lymphoid tissues.

Dry eye disease (DED) once thought to be solely due to deficiency of tears, is increasingly being recognized as an immune-mediated disorder) DED affects many millions of people with a wide spectrum of seminal features ranging from mild ocular discomfort to sight-threatening corneal complications such as persistent epithelial defects and sterile stromal ulceration) In the United States alone, more than 3.2 million women and 1.6 million men above the age of 50 years are affected by this potentially disabling disease adversely impacting the vision-related quality of life.

Clinically significant DED is associated with ocular surface inflammation, although the precise immunopathogenesis is not known. There is strong evidence regarding T cell involvement in the pathogenesis of DED in both animal models and humans. Recently, we illustrated T cell activation in the regional lymph nodes of dry eye mice, coincident with acquisition of specific chemokine markers which help in the homing of T cells to the inflamed ocular surface. Further we demonstrated induction of autoimmunity in the draining lymph nodes of dry eye mice due to impaired Treg function and generation of pathogenic Th17 cells. These Th17 cells were found to be resistant to Treg mediated suppression, leading to unrestrained generation of pathogenic T cells and sustained ocular surface inflammation. Accordingly, much of the work to date has focused on understanding immunological phenomena occurring in the lymphoid compartment and the effector responses thereby generated, leaving unanswered the question as to how naive T cells in the draining lymph nodes get primed to the ocular surface antigen(s) that drive immunity in DED.

The draining lymph nodes are critical sites for induction of immunity and their role in generation of alloimmunity has been well established in corneal transplantation. The enhanced survival rate of corneal transplants in mice with excised cervical lymph nodes implicates the importance of functional flow of antigen presenting cells (APCs) from the ocular surface to the to the draining lymphoid tissue as a necessary component of alloimmunity and graft rejection. However, little is known about the pathway that allows trafficking of corneal APCs to the draining lymph nodes where they prime naive T cells to corneal antigens and generate autoimmune responses in dry eye.

Emphasis is now being given to the importance of pathological angiogenesis (hem- and lymphangiogenesis) in various corneal diseases such as different forms of keratitis, chemical burns, graft vs host disease etc., but to date there is no data regarding corneal angiogenesis in DED. A plausible reason could be that most of the above mentioned conditions except DED are accompanied by in-growth of clinically visible blood vessels into the cornea. Traditionally it has been thought that lymphatics and blood vessels which serve as afferent and efferent arms of the immune response respectively are always coexistent in pathological states. The present work provides the first evidence for selective lymphangiogenesis occurring in DED cornea using a murine model. Herein, we attempt to determine the growth of lymphatic vessels into the cornea with the progression of DED, discuss the pathophysiologic implications of corneal lymphangiogenesis in dry eye and the potential of antilymphangiogenic therapy for ameliorating DED.

Discussion

Lymphangiogenesis in the postnatal period is primarily a response to inflammation and is seen in various pathological states as diverse as tumor metastasis, wound healing and transplantation. Lymphatics play an important role in generating immuno-inflammatory responses by directing the antigen bearing immunocytes (e.g. dendritic cells) from the periphery to the draining lymph nodes where T cells are primed and expanded. The normal human cornea is avascular, thus suppressing the afferent lymphatic and efferent vascular arms of the immune cycle Inflammation however negates this "immune" and "angiogenic" privileged state of the cornea and gives it the potential to mount an immune response.

Angiogenesis in the cornea is now extensively being studied in various pathological models such as transplantation. Whereas corneal blood vessels have long been thought to be an important risk factor for immune rejection in corneal transplantation, it is only recently after unveiling of new lymphatic specific markers, that the significance of lymphangiogenesis in corneal alloimmunity has been characterized. Despite recognizing the role of inflammatory angiogenesis in the eye, little has hitherto been studied regarding angiogenic mechanisms in DED. Desiccating stress in DED initiates an immune-based inflammatory response that is sustained by the ongoing interplay between the ocular surface and various pathogenic immune cells, primarily the $CD4^+$ T cells in the conjunctiva and CDI 1b+ monocytic cells in the cornea. Desiccating stress induces secretion of inflammatory cytokines, especially interleukin (IL)-1, tumor necrosis factor-a, and IL-6 by ocular surface tissues, which facilitate the activation and migration of resident APCs toward the regional draining LN. Our data on frequencies of mature APC in the LN also suggest increased trafficking of mature APC in the LN of DED mice (FIG. 7). In the LN, these APCs stimulate naive T cells, leading to the expansion of IL-17 secreting Th17 cells and interferon (IFN)-y-secreting Th1 cells. Once these effectors are generated in the LN, they migrate to the ocular surface and secrete effector cytokines. Recent work has provided evidence for the induction of T cell mediated autoimmune responses in the regional lymph nodes of DED mice. But what has remained unanswered is how corneal APCs can traffic to the draining lymphoid compartment in order to initiate the immune cycle in DED.

Interestingly, to date there has been no published data on this important facet of immunity in DED. The data presented herein clearly demonstrates the development of lymphatic vessels in the setting of the dry eye state. These lymphatic vessels increase both in caliber and area while advancing toward the corneal center with progression of dry eye. Remarkably, these lymphatic vessels are not accompanied by growth of blood vessels. Various spatio-temporal studies examining relation between new blood and lymphatic vessels have led to the belief that a preexisting blood vascular bed is necessary to guide lymphangiogenesis. The current study refutes the general perception of wound healing models in skin where growth of lymphatic vessels follows that of blood vessels by several days. This is also in contrast to other robust models of corneal inflammation where there is either parallel outgrowth of blood and lymphatic vessels or the blood vessels are precedent over the lymphatics. This provides the first evidence of selective 'natural' (non pharmacologically induced) lymphangiogeneis in a disease model that is dissociated from hemangiogenesis.

Lymphangiogenesis is mediated primarily by the interaction of growth factors VEGF-C and VEGF-D on VEGFR-2 and VEGFR-3. VEGF-A also contributes, albeit indirectly, to lymphangiogenesis by recruiting VEGF-C and VEGF-D secreting macrophages. In the present study, dry eye induction led to the up-regulation of all the VEGF growth factors and their receptors. Though the rise in levels of VEGF-A, VEGF-C and VEGFR-2 occurred at later time points (day 14), it is noteworthy, that VEGF-D and VEGFR-3 (which are both largely specific to lymphangiogenesis) increased as early as day 6 of disease. The functional relevance of the early rise of VEGF-D is highlighted in a recent study where VEGF-D, via its action on VEGFR-3, was shown to be a critical modifier of VEGF-C driven early sprouting and migration of lymphatic endothelial cells. Macrophages also seem to play a crucial role in lymphangiogenesis. Under normal physiological conditions, all ocular tissues except the central cornea are rich in bone marrow derived $LYVE-1^+$ macrophages which may serve as precursor cells for de novo formation of lymphatics. In the present study, we noticed significantly increased number of $CD11b^+/LYVE-1^+$ cells in the peripheral corneas after exposure to desiccating stress, suggesting that either these cells infiltrate into or multiply from pre-existing CD1 113'7 LYVE-1+ cells in the cornea, and contribute to lymphangiogenesis. Alternatively, there is a possibility of upregulation of LYVE-1 in the previous $CD11b^+/LYVE-1^-$ cells.

In summary, presented herein is novel evidence for the selective growth of lymphatic (but not blood) vessels in dry eye disease providing new insights into the pathophysiology of the disease. The findings suggest that these newly formed corneal lymphatics may serve as potential conduits for migration of corneal APCs to lymphoid tissues where they generate autoreactive Th17 and Th1 cells in DED. This study not only provides a link between ocular surface inflammation and the generation of T cell mediated immunity in the lymphoid compartment, but also offers an example of how lymphangiogenesis and hemangiogenesis can be 'naturally' dissociated in a pathological state. The severing of the 'eye-lymphatic axis' in other immune-mediated conditions, such as transplant rejection, has been shown to hold promise as a strategy of suppressing alloimmunity without inhibiting needed innate host defense mechanisms. Similarly, a strategy targeting prolymphangiogenic factors such as VEGF-C or VEGF-D may prove effective in ameliorating dry eye disease.

Example 7: Blockade of Prolymphangiogenic VEGF-C Suppresses Dry Eye Disease

Effect of in vivo blockade of pro-lymphangiogenic VEGF-C on Dry Eye Disease Rationale: Dry eye disease (DED) is an immune-mediated disorder whose precise pathogenesis remains largely unknown. While it has been clearly established that in DED generation of pathogenic $CD4^+$ T cells (Th1/Th17) primarily occur in the draining lymph nodes, the mechanisms of trafficking of corneal antigen presenting cells (APC) to lymphoid tissues where they activate and expand pathogenic $CD4^+$ T cell subsets, were still not well understood prior to the invention described herein. The present invention provides evidence for the selective growth of lymphatic (but not blood) vessels in DED cornea. Data shows a significant increase in both caliber and extent of lymphatics in DED corneas which was also confirmed using real-time PCR by showing a highly significant over-expression of lymphangiogenic receptor VEGFR-3 (in contrast to a non-statistically significant increase in hemangiogenic receptor VEGFR-2 expression). This study not only provides a link between ocular surface inflammation and the generation of T-cell mediated immunity in the lymphoid compartment, but also offers an example of how lymphangiogenesis and hemangiogenesis can be 'naturally' dissociated in a pathological state. Data suggests that these corneal lymphatics may serve as conduits for migration of corneal APCs to lymphoid tissues where they activate autoreactive T cells in DED.

Immunopathogenesis of DED: The pathogenesis is not fully understood. Ocular surface inflammation sustained by ongoing activation and infiltration of pathogenic immune cells. Strong evidence of T cell involvement. Recent work draining lymphoid tissue primary site for activation and generation of auto reactive effector T cells in DED (Chauhan et al; Role of cTh17 cells in the immunopathogenesis of dry eye disease. Mucosal Immunol. 2009; 2(4):375-376.).

Expression levels of VEGF's and VEGFR's in DE corneas using RT PCR has demonstrated an increased transcript expression of VEGF-C, VEGF-D, and VEGFR-3. Thus, targeting pro-lymphangiogenic VEGF-C/D has therapeutic implications in DED.

Corneal lymphatics play an important role in mediating the corneal inflammation in dry eyes. Experiments: To validate this, inhibition of corneal neolymphangiogenesis was performed in a well characterized mouse model of DED described above. To see if inhibition of corneal neolymphangiogenesis could decrease ocular surface inflammation, anti-VEGF-C antibodies were administered i.p. daily from day −1 to day 10 to DED mice and assessed clinically using corneal fluorescein staining.

Methods (as described previously): Induction of Dry Eye Disease. Experimental Dry Eye Murine Model. Assessment of Corneal Surface: Corneal Fluorescein Staining. Immunohistochemistry: Monocyte/macrophage marker—CD11b; Pan-endothelial marker—CD31; Lymphatic endothelial marker—LYVE-1; Blood vessels: CD31$^{hi}$/LYVE-1; Lymph vessels: CD31$^{lo}$/LYVE-1$^{hi}$. Morphometry of Lymphangiogenesis: Automated image analysis program written using Mat lab. Lymphatic Area (LA)—total surface area of the lymphatic vessels when projected into the plane of the image. Lymphatic Caliber (LC)—measure of the diameters of the lymphatic vessels.

Anti-VEGF-C antibody and treatment regimen. Experimental design: Three groups: Normal, DE group treated with IP normal Saline (Untreated) and DE group treated with anti-VEGF-C antibody (VGX-100; a gift from Vegenics, Australia). Daily IP application of anti-VEGF-C antibody/ Normal saline from day −1 to day 13. Dose: 400 pg (20 mg/kg) in 100 pl of Normal Saline.

Figure 14:
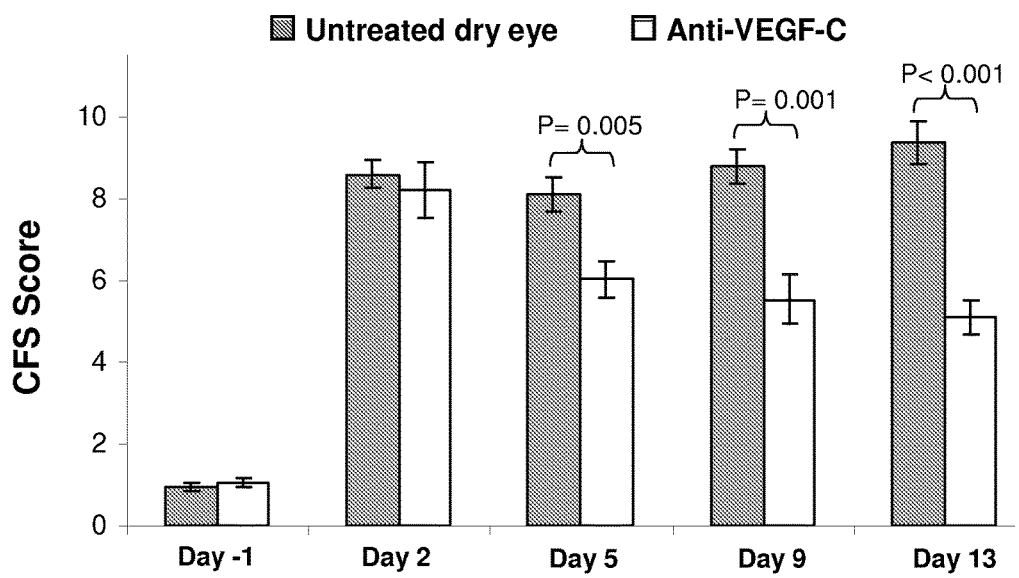
FIG. 14: In vivo blockade of VEGF-C ameliorates clinical signs of DED. Corneal fluorescein staining (CFS) score is used as readout for the clinical signs of dry eye inflammation, in anti-VEGF-C Ab-treated and untreated mice. CFS scores were significantly decreased in the group treated with anti-VEGF-C antibody at days 5, 9 and 13 vs the untreated group. Data shown as mean±S.E.M and each group consisted of 3-4 mice.

The results are presented in FIG. 14. Results: The data clearly shows a significant decrease in disease severity in anti-VEGF-C-treated group compared to the untreated group. In conclusion, suppression of lymphatic growth with VEGF-C blockade led to significant improvement in DED reflected by decrease in: corneal epitheliopathy; corneal infiltration of CD11b$^+$ cells; expression of pro-lymphangiogenic growth factors and receptors (VEGF-C, -D, R3) in DE corneas; and mRNA expression levels of proinflammatory cytokines in the conjunctiva.

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method of treating dry eye disease (DED) in a human comprising:
administering a composition comprising a tyrosine kinase inhibitor that inhibits the activity of VEGFR-3 and a pharmaceutically acceptable carrier to the human subject, in an amount effective to treat dry eye disease.

2. The method of claim 1, wherein the composition is administered to the eye of the human.

3. The method of claim 1, wherein the DED is an autoimmune DED or a DED associated with Sjogren's syndrome.

4. The method of claim 1, wherein the DED is DED due to excessively fast tear evaporation (evaporative dry eyes) or inadequate tear production.

5. The method of claim 1, wherein the dry eye disease is attributable to one or more causes selected from: aging, contact lens usage and medication usage.

6. The method of claim 1, wherein the dry eye disease is a complication of LASIK refractive surgery.

7. The method of claim 1, further comprising administering an anti-inflammatory agent to the subject.

8. The method of claim 7, further comprising administering cyclosporine to the subject.

9. The method of claim 1, wherein said composition further comprises a molecule that inhibits an activity of an inflammatory cytokine selected from the group consisting of IL-1, IL-7, IL23, IL-6 and TNF-α.

10. The method of claim 1, wherein the method further comprises administering an antibiotic to the human.

11. The method of claim 10, wherein the antibiotic is selected from the group consisting of amikacin, gentamicin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, clozacillin, dicloxacillin, flucoxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflaxacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline.

12. The method of claim 2, wherein the eye comprises a tissue or gland in or around the eye selected from the group consisting of ocular tissue, eyelids of the subject, ocular surface, meibomian gland and or lacrimal gland of the human.

13. The method of of claim 1, wherein said composition is administered topically to the eye of the human subject.

14. The method of claim 1, wherein the composition is formulated for topical administration.

15. The method of claim 1, wherein said composition is in the form of a solid, a paste, an ointment, a gel, a liquid, an aerosol, a mist, a polymer, a film, an emulsion, or a suspension.

16. The method of claim 1, wherein the composition further comprises a compound selected from the group consisting of physiological acceptable salt, poloxamer analogs with carbopol, carbopol/hydroxypropyl methyl cellulose (RP MC), carbopol-methyl cellulose, carboxymethylcellulose (CMC), hyaluronic acid, cyclodextrin, and petroleum.

* * * * *

UNITED STATES PATENT AND TRADEMARK OFFICE
CERTIFICATE OF CORRECTION

PATENT NO. : 10,179,160 B2
APPLICATION NO. : 15/083907
DATED : January 15, 2019
INVENTOR(S) : Reza Dana et al.

It is certified that error appears in the above-identified patent and that said Letters Patent is hereby corrected as shown below:

On the Title Page

In Column 1, below "Related U.S. Application Data", Line 1, "(60) filed" should be
-- (63) Continuation of application No. 13/579,170, filed --.

In Column 1, below "Related U.S. Application Data", Line 3, "Provisional application No. 13/579,170, provisional" should be -- Provisional --.

In the Claims

At Column 123, Line 47, "IL23," should be -- IL-23, --.

At Column 124, Lines 22-23, "clozacillin," should be -- cloxacillin, --.

At Column 124, Line 23, "flucoxacillin," should be -- flucloxacillin, --.

At Column 124, Line 26, "oflaxacin," should be -- ofloxacin, --.

At Column 124, Line 29, "soxycycline," should be -- doxycycline, --.

At Column 124, Line 36, "method of of" should be -- method of --.

At Column 124, Line 48, "(RP MC)," should be -- (HPMC), --.

Signed and Sealed this
Twentieth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 10,179,160 B2  
APPLICATION NO. : 15/083907  
DATED : January 15, 2019  
INVENTOR(S) : Reza Dana et al.

Page 1 of 2

It is certified that error appears in the above-identified patent and that said Letters Patent is hereby corrected as shown below:

In the Specification

At Column 1, Lines 7-9:
"This invention was made with Government support under Grant No EY-12963 awarded by the National Institute of Health. The Government has certain rights in the invention."
Should read:
-- This invention was made with Government support under Grant No EY012963 awarded by the National Institutes of Health. The Government has certain rights in the invention. --

At Column 2, Line 60: "clozacillin," should read -- cloxazillin, --

At Column 2, Line 60: "flucoxacillin," should read -- flucloxacillin, --

At Column 2, Line 64: "oflaxacin," should read -- ofloxacin, --

At Column 2, Line 66: "soxycycline," should read -- doxycycline, --

At Column 3, Line 11: "(RP MC)" should read -- (HPMC) --

At Column 6, Line 27: "IL23" should read -- IL-23, --

At Column 6, Line 39: "clarithromycin, clarithromycin" should read -- clarithromycin, --

At Column 6, Line 41: "clozacillin," should read -- cloxazillin, --

At Column 6, Line 41-42: "flucozacillin," should read -- flucloxacillin, --

At Column 6, Line 47: "soxycycline," should read -- doxycycline, --

At Column 6, Line 53: "and or" should read -- and/or --

Signed and Sealed this  
Twenty-eighth Day of July, 2020

Andrei Iancu  
*Director of the United States Patent and Trademark Office*

CERTIFICATE OF CORRECTION (continued)
U.S. Pat. No. 10,179,160 B2

At Column 7, Line 1: "(RP MC)" should read -- (HPMC) --

In the Claims

At Column 124, Line 34: "and or" should read -- and/or --